United States Patent
Howley et al.

(10) Patent No.: US 10,095,834 B2
(45) Date of Patent: Oct. 9, 2018

(54) INTEGRATION PLATFORM AND APPLICATION INTERFACES FOR REMOTE DATA MANAGEMENT AND SECURITY

(71) Applicant: YC Wellness, Inc., Middleboro, MA (US)

(72) Inventors: Joseph Howley, Middleboro, MA (US); Jonathan Ervin Creekmore, Apex, NC (US)

(73) Assignee: YC Wellness, Inc., Middleboro, MA (US)

( * ) Notice: Subject to any disclaimer, the term of this patent is extended or adjusted under 35 U.S.C. 154(b) by 271 days.

(21) Appl. No.: 15/148,452

(22) Filed: May 6, 2016

(65) Prior Publication Data
US 2016/0328577 A1 Nov. 10, 2016

Related U.S. Application Data

(60) Provisional application No. 62/308,314, filed on Mar. 15, 2016, provisional application No. 62/158,653, filed on May 8, 2015.

(51) Int. Cl.
*G06F 7/04* (2006.01)
*G06F 17/30* (2006.01)
(Continued)

(52) U.S. Cl.
CPC .......... *G06F 19/322* (2013.01); *G06F 3/0482* (2013.01); *G06F 3/0484* (2013.01);
(Continued)

(58) Field of Classification Search
CPC ............. G06F 19/322; G06F 17/30283; G06F 21/6245; G06F 3/0482; G06F 3/0484;
(Continued)

(56) References Cited

U.S. PATENT DOCUMENTS

| | | |
|---|---|---|
| 6,561,951 B2 | 5/2003 | Cannon et al. |
| 2002/0032583 A1 | 3/2002 | Joao |

(Continued)

OTHER PUBLICATIONS

Invitation to Pay Fees dated Dec. 29, 2016 in connection with International Application No. PCT/US2016/031165.
(Continued)

*Primary Examiner* — Aravind K Moorthy
(74) *Attorney, Agent, or Firm* — Wolf, Greenfield & Sacks, P.C.

(57) ABSTRACT

Various embodiments implement a multiplatform system architected to provide secure messaging between a plurality of disparate systems (e.g., mobile devices, secure cloud systems, remote locations, health monitoring devices, fitness centers, etc.), co-ordinate resources associated with each of the disparate systems, manage communication between proprietary applications via customized application programming interfaces (APIs) and manage reservation of resources of the disparate systems via the APIs. Further embodiments enable an extensible system architecture to incorporate additional systems. In some embodiments, the system includes a multi-layered database architecture to mediate information and access control (e.g., based on inheritable privileges, specific user classes are allowed or denied access to data in the database). In further embodiments, the data architecture is architected with access layers that ensure compliance with regulatory systems governing health data.

20 Claims, 26 Drawing Sheets

(51) Int. Cl.
  *H04L 29/06* (2006.01)
  *G06F 21/00* (2013.01)
  *G06K 9/00* (2006.01)
  *G06F 19/00* (2018.01)
  *G06F 21/62* (2013.01)
  *G06Q 10/10* (2012.01)
  *G06Q 40/08* (2012.01)
  *G06F 3/0484* (2013.01)
  *G06F 3/0482* (2013.01)
  *H04L 29/08* (2006.01)
  *G16H 10/60* (2018.01)

(52) U.S. Cl.
  CPC ..... *G06F 17/30283* (2013.01); *G06F 19/3475* (2013.01); *G06F 21/6245* (2013.01); *G06Q 10/1097* (2013.01); *G06Q 40/08* (2013.01); *G16H 10/60* (2018.01); *H04L 63/0861* (2013.01); *H04L 67/025* (2013.01); *H04L 67/04* (2013.01); *H04L 67/10* (2013.01); *H04L 67/12* (2013.01); *H04L 67/22* (2013.01); *H04L 67/306* (2013.01); *H04L 67/32* (2013.01); *H04L 63/0428* (2013.01)

(58) Field of Classification Search
  CPC ..... G06F 19/3475; G16H 10/60; H04L 67/22; H04L 67/10; H04L 67/32; H04L 67/12; H04L 67/04; H04L 67/025; H04L 67/306; H04L 63/0861; H04L 63/0428; G06Q 10/1097; G06Q 40/08

USPC ............. 726/26, 5; 713/165, 166, 182, 186; 382/115, 116, 124
  See application file for complete search history.

(56) References Cited

U.S. PATENT DOCUMENTS

| | | |
|---|---|---|
| 2006/0228681 A1 | 10/2006 | Clarke |
| 2007/0100595 A1 | 5/2007 | Earles et al. |
| 2010/0221695 A1 | 9/2010 | Desai et al. |
| 2010/0274578 A1 | 10/2010 | Firminger et al. |
| 2014/0191867 A1 | 7/2014 | Yuen et al. |
| 2014/0257047 A1 | 9/2014 | Sillay et al. |
| 2015/0066534 A1 | 3/2015 | Tanaka et al. |
| 2015/0186636 A1* | 7/2015 | Tharappel ............... G06F 21/32 726/8 |
| 2015/0278498 A1* | 10/2015 | Hong ..................... G06F 21/32 340/5.82 |
| 2016/0135046 A1* | 5/2016 | John Archibald .... H04W 12/06 455/411 |
| 2016/0275254 A1 | 9/2016 | Mahoney |
| 2017/0171741 A1* | 6/2017 | Hannon ................ H04W 8/245 |

OTHER PUBLICATIONS

International Search Report and Written Opinion dated Feb. 24, 2017 in connection with International Application No. PCT/US2016/031165.

Office Communication dated Aug. 7, 2018 for U.S. Appl. No. 15/148,377.

\* cited by examiner

CURRENT ASSOCIATED MEMBERS — 1501, 1502

| | NAME | EMAIL | STATUS |
|---|---|---|---|
| ☐ | Cirone, Don | gemguy56@hotmail.com | ProgramActive |
| ☐ | Devito, Mike | mdevito@ft.newyorklife.com | ProgramActive |
| ☐ | Giordani, Diane | fhrabbitry129@gmail.com | ProgramActive |
| ☐ | Mattson, Kristin | kirstren@yahoo.com | ProgramActive |
| ☐ | Hamilton, Christina | captainname903@netscape.net | ProgramActive |

1 2 3 4 5 6    Page 1 of 6, Items 1 to 5 of 26.

1502 — [ASSIGN MEMBERS] [REMOVE MEMBERS]

FIG. 15A

ASSIGN MEMBERS — 1505, 1506

Type Member Name 🔍

| | | 1508 |
|---|---|---|
| Ralph Frecnelle | → | Heather Dan |
| Peter Gothis | ← | Jill Devito |
| Judith Volpe | ⇥ | Chris Carey |
| Christine Melanson | ⇤ | Anthony Rossi |
| Marianna Sullivan | | Noreen McCarthy |
| Krystyna Lukasik | | |
| Ashley Shute | | |
| Ryder Talcott | | |
| David Alieko | | |

[ASSIGN]   [CANCEL]

FIG. 15B

INTEGRATION PLATFORM AND APPLICATION INTERFACES FOR REMOTE DATA MANAGEMENT AND SECURITY

RELATED APPLICATIONS

This application claims priority under 35 U.S.C. § 119(e) to U.S. Provisional Application Ser. No. 62/158,653 entitled "SCHEDULE MANAGEMENT SYSTEM," filed on May 8, 2015; and under 35 U.S.C. § 119(e) to U.S. Provisional Application Ser. No. 62/308,314 entitled "SCHEDULE MANAGEMENT SYSTEM," filed on Mar. 15, 2016, which applications are incorporated herein by reference in their entirety.

BACKGROUND

Aspects of the present application relate to database systems, schedule management, and information encryption and security.

SUMMARY

According to one aspect, a multiplatform system is architected to provide secure messaging between a plurality of disparate systems (e.g., mobile devices, secure cloud systems, remote locations, health monitoring devices, etc.), co-ordinate resources associated with each of the disparate systems, manage communication between proprietary applications via customized application programming interfaces (APIs) and manage reservation of resources via the APIs, while enabling an extensible system architecture. In further embodiments, the system includes a multi-layered database architecture to mediate information and access control (e.g., based on inheritable privileges, specific user classes are allowed or denied access to data in the database). In further embodiments, the data architecture is architected with access layers that ensure HIPAA (Health Insurance Portability and Accountability Act) compliance and/or compliance with the HITECH (Health Information Technology for Economic and Clinical Health) Act.

According to another aspect, integration of the platform with health monitoring devices enables improvements in authentication protocols and continued authentication verification. In one embodiment, an access control API is configured to poll or receive biometric data from user devices (e.g., mobile phones, smart phones, portable computing systems, etc.) and paired health monitoring devices (e.g., FITBIT, JABRA PULSE, SKULPT, etc.). If the biometric signal or biometric capture ceases an existing authentication session can be terminated.

In other embodiments, health data capture can be used to build a biometric profile for respective users (e.g., the biometric profile can include patterns of heart rate over time, blood pressure over time, movement over time, respiration over time), each biometric profile can include a plurality of biometric patterns that are also indexed by the system on known user activity (e.g., scheduled fitness session, bike ride, run, swim, training, etc.) or that incorporate prior biometric captures during the same or similar activity (e.g., spin class, taebo, boxing session, physical therapy, etc.). Determinations of user activity can automatically generated, for example, based on integrated fitness scheduling systems (e.g. the user has a scheduled appointment with a trainer, or a trainer has an appointment with a number of users including the current authenticated user). In other embodiments, the system can infer an activity from applications running on the user's device (e.g., run tracker app, bike tracker app, GPS tracking data can be used to derive speed and a likely activity, etc.). Thus, biometric patterns can be augmented to specifically address a user activity, an effect on health data received—enabling increased security with minimal computational overhead.

In further embodiments, APIs manage secure communication of health information as it is transmitted from monitoring devices to paired mobile devices, from mobile devices to central information collection, and is managed during collection of information from remote systems (e.g., calorie/nutrition planning systems, fitness scheduling and tracking system, physician integration systems, etc.). In other embodiments, integrated systems (e.g., physician systems) can access the system to view health information, fitness activity, and even schedule appointments with users or training sessions for users. The APIs coupled with the multi-layered database architecture ensures appropriate access to protected health information. Further the architecture of the database is configured to provide access to information based on platform and user privileges maintain HIPAA compliant storage and access to health information.

According to another aspect, health monitoring devices can be specially configured as the default interface for the multi-platform system. According to one embodiment, fitness devices paired with mobile computing devices are configured to accept verbal commands and provider audio prompts to end user, to allow the end users to navigate the functions and operations of the multi-platform system. According to one embodiment, voice command received by the a fitness device are communicated to a paired mobile device executing a secure application. In some embodiments, the fitness device can be augmented to include embedded processors and processing for interpreting verbal commands. In other embodiments, the fitness device passes the verbal input to the mobile device to control user connections and/or interactions with the system, and/or functions on the secure application or fitness device itself.

According to another aspect, the multi-platform system includes a plurality of APIs each tailored to connect and communicate with remote systems, and integrate the respective functionality of the remote systems. A first API is configured to co-ordinate scheduling operations between users, trainers, physicians, fitness centers and/or resources at the fitness centers. According to one embodiments, the first API can be configured to manage data access and scheduling such that any access preserves compliance on the this with health care regulation. For example, protected health information ("PHI") can be maintained on the multi-platform system and associated with access tiers or layers, scheduling and coordination operations are restricted from the PHI. For example, the first API can access data on a first user, availability, prior fitness activities, fitness classes, etc., but is prevented from access the underlying PHI associated with the first user.

A second API can be configured to connect and communicate with physician systems. The second API can manage access by respective physicians and/or physician groups. For example, a first user can "opt in" to allowing his or her physician to access biologic data collected during physical therapy, fitness activities, etc. The second API is configured to limit access to biologic data to user who have specifically opt in or express consent electronically on the system. The second API is further configured to manage associations between users and their physicians so that physicians can only access their own patient's data.

In further embodiments, additional integration can be achieved through one or more APIs. In another example, nutrition planning systems can be integrated into the multi-platform architecture. In one example, a third API can be configured to translate verbal command received at a first use device into operations performs on a nutrition planning system. In another example, the multi-platform system can incorporate inputs from any number of remote systems, and augment machine learning operations to build custom fitness routines for users. In some examples, planning APIs are specially configured to develop and implement custom fitness routines, and in some examples, incorporating data from the integrated systems (e.g., scheduling coordination, nutrition planning, physician review, etc.).

Further embodiments of the present application provide systems and methods for schedule management. More specifically, embodiments disclosed herein relate to an application for securely allowing a physician or fitness coach to work with clients in multiple fitness centers and manage his schedule with the different fitness centers. Embodiments also relate to securely communicating securely fitness regimens and matching a client with a trainer who is best fit to treat the client. Further embodiments implement database architectures configured to define associations between trainers, clients, and fitness centers and enable management efficiency across locations, specialties, and schedules while preserving compliance with health care regulation.

According to one aspect a database system for executing multi-tier data and multi-platform data access requests is provided. The system comprises at least one processor operatively connected to a memory, the at least one processor when executing configured to: receive biologic data (e.g., heart rate, pulse, respiration, blood pressure, ECG readings, central nervous system readings, etc.) from a first user device (e.g., Jabra pulse, Fitbit, step counter, sleep monitor, etc.) operatively paired with a second user device (e.g., mobile phone, smart phone, portable computing device, etc.) associated with a first user, wherein the first user device collects biologic data and the second user device communicates the biologic data; store biologic data from the first user in a database; associate the biologic data to a plurality of access tiers in the database, the plurality of access tiers including at least a first access tier including the first user, a second access tier including additional users granted electronic permission on the system to access the biologic data by a user associated with the biologic data, and an access tier for administrative functions executed by the system or components; and limit within the second access tier access by the additional users to only the data associated with respective users having given permission on the system; display an interface for the additional users to remotely access the system, request services for the first user, receive reports on the first user's biologic data, and access the biologic data for the first user within the interface.

In one embodiment, the system is configured to capture and store at least some biologic data as a time series (e.g., capture readings with time). In another embodiment, the database system can also be configured to indexed at least some of the biologic data with a known or inferred activity of the user (e.g., running, sleeping, working, biking, hiking, taebo class, fitness class, training session, spin class, yoga, etc.). In another embodiment, for any requested service by the additional user, the at least one processor is configured to: automatically identify physical resources and candidate personnel required for the request; coordinate between a plurality of locations and resource availability information associated with required resources and personnel, and wherein coordination includes executing at least a first API to capture resource availability information from one or more systems executing at at least one of the plurality of locations and wherein the first API is further configured to reserve the resources identified as required for the request and confirm the reservation of resources with the one or more systems.

According to one aspect, a database system for executing multi-tier data and multi-platform data access requests. The system comprises at least one processor operatively connected to a memory, the at least one processor when executing configured to: receive biologic data (e.g., heart rate, pulse, respiration, blood pressure, ECG readings, central nervous system readings, etc.) from a first user device (e.g., Jabra pulse, Fitbit, step counter, sleep monitor, etc.) operatively paired with a second user device (e.g., mobile phone, smart phone, portable computing device, etc.) associated with a first user, wherein the first user device collects biologic data and the second user device communicates the biologic data; store biologic data from the first user as a time series (e.g., capture readings and time) indexed with a known or inferred activity of the user (e.g., running, sleeping, working, biking, hiking, taebo class, fitness class, training session, spin class, yoga, etc.) in a database; associate the biologic data to a plurality of access tiers in the database, the plurality of access tiers including at least a first access tier including the first user, a second access tier including additional users granted electronic permission on the system to access the biologic data by a user associated with the biologic data, and an access tier for administrative functions executed by the system or components; limit within the second access tier access by the additional users to only the data associated with respective users having given permission on the system; display an interface for the additional users to remotely access the system, request services for the first user, receive reports on the first user's biologic data, and access the biologic data for the first user within the interface; wherein for any requested service by the additional user, the at least one processor is configured to: automatically identify physical resources and candidate personnel required for the request; coordinate between a plurality of locations and resource availability information associated with required resources and personnel, and wherein coordination includes executing at least a first API to capture resource availability information from one or more systems executing at at least one of the plurality of locations and wherein the first API is further configured to reserve the resources identified as required for the request and confirm the reservation of resources with the one or more systems.

Various embodiments of the above systems and embodiments are implemented with the following refinements and/or elements, which include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, nineteen selections, twenty selections, twenty one selections, twenty two selections, or twenty three selections from the following additional elements or refinements: wherein the at least one processor is further configured to receive sensor data from at least the first and second device and store the sensor data in records with associations to the first user; wherein the at least one processor is further configured to store the sensor data with associations to any biologic data received on the first user; wherein the at least one processor is further configured to: identify the second device as a registered user device through a unique registration number or digital fingerprint associated with the second user device during registration; identify the first user device as a registered user device through a unique registration number or digital fingerprint associated with the first user device during registration or issuance of the first device to the first user; wherein the at least one processor is configured to permit authentication of the user for access to the system responsive to identifying at least one of the first user device or the second user device and deny entry of authentication information in response to not identifying either of the first user device or the second user device; wherein the system is configured to: associate the first user with a first user device for collecting biologic data; associate a unique identifier for the first user device with a data record for the first user assigned to the administrative tier; and deliver the first user device to the first user; further comprising at least a second API executed by the at least one processor, the second API configured to determine an activity executed by the first user based on at least one of: scheduling information stored in the database, resource allocations associated with the first user, personnel allocations associated with the first user, or facility associations associated with the first user; further comprising at least a second API executed by the at least one processor, the second API configured to: request or receive execution data associated with the first user's second device, wherein the execution data includes information on currently executing applications on the second user device, and infer a current user activity responsive to analysis of the currently executing application information; further comprising at least a second API executed by the at least one processor, the second API configured to: request or receive telemetric data (e.g., motion, speed, position, elevation, etc.) associated with the first user's second device or first device, and infer a current user activity responsive to analyzing the telemetric data; wherein analyzing the telemetric data includes comparing received telemetric data, and, optionally, in conjunction with received biologic data, to historic activity and, optionally, the biologic data for the first user; wherein the at least one processor is further configured to: control data access to the plurality of access tiers and associated biologic information associated with the first user; and maintain compliance with regulatory requirements for protected health information; wherein the additional user is a trainer granted access by the first user accessing the system through a trainer portal to schedule a fitness activity for the first user; wherein the at least one processor is further configure to accept a request from the first user specifying a fitness activity; wherein the system is configured to accept specification by the first user of additional users able to schedule activities for the first user or view health and fitness data, wherein the system is further configure to accept specification of granular data access (e.g., summary information only, trainer detail access to trainer run sessions only, physician access to all health data, physician access or trainer access to activity information only (e.g., not biologic data capture), etc.); wherein one or more APIs are configured to enforce user specific access restrictions to the user's health information; wherein the at least one processor is further configured to query available resources across a plurality of systems to match available resources to parameters specified by the user in the request or matching parameters specified in the user's profile; wherein the at least one processor is further configured to establish a secure communication session to a trainer specified in the user request, and communicate biologic data captured during the execution of a trainer led activity; wherein the at least one processor is further configured to communicate over a secure connection the captured biologic data to a remote device associated with the trainer, and communicate over a secure connection the captured biologic data for storage on the system; wherein access to biologic data stored on the system by the trainer is limited to data captured during trainer led activities, responsive to access grant by the first user; wherein access to biologic data stored on the system by the physician is limited responsive to access grant by the first user; wherein the at least one processor is further configured to accept user request for fitness activity, and responsive to the user request query available resources (e.g., fitness center locations, fitness equipment, sensor equipment, video equipment, etc.) across a plurality of locations and personnel to determine matching resources for the user request; wherein the at least one processor is further configured to retrieve user profile preferences associated with the resources (e.g., default location, default trainer (e.g., trainer based on class or activity), etc.) to determine matching resources; wherein the at least one processor is further configured to present matching resources to the user to accept specification of the fitness activity; wherein the second device establishes a secure connection to the first device such that biologic data collection and communication is encrypted between the first device, the second user device, and a database for storing the biologic data; or wherein the second user device establishes a secure connection to the database through the secure application such that any data communicated is encrypted between the second device and the database system; wherein the multi-tier database includes an access tier for an insurance provider associated with the first user, wherein the system can accept a first user grant of access for the insurance provider, wherein the access permission are enforced with a minimum data access acceptable to prove an expense with the provider (e.g., summary information, activity, date, purpose, and value).

According to one aspect, a computer implemented method for executing multi-tier data and multi-platform data access requests is provided. The method comprises receiving, by at least one processor, biologic data (e.g., heart rate, pulse, respiration, blood pressure, ECG readings, central nervous system readings, etc.) from a first user device (e.g., Jabra pulse, Fitbit, step counter, sleep monitor, etc.) operatively paired with a second user device (e.g., mobile phone, smart phone, portable computing device, etc.) associated with a first user, wherein the first user device collects biologic data and the second user device communicates the biologic data; storing, by the at least one processor, biologic data from the first user in a database; associating, by the at least one processor, the biologic data to a plurality of access tiers in the database, the plurality of access tiers including at least a first access tier including the first user, a second access tier including additional users granted electronic permission on the system to access the biologic data by a user associated with the biologic data, and an access tier for administrative functions executed by the system or components; limiting, by the at least one processor, within the second access tier access by the additional users to only the data associated with respective users having given permission on the system; and displaying, by the at least one processor, an interface for the additional users to remotely access the system, request services for the first user, receive reports on the first user's biologic data, and access the biologic data for the first user within the interface.

In one embodiment, at least some of the biologic data is stored as a time series (e.g., capture readings and time). In another embodiment, at least some of the biologic data is also indexed with a known or inferred activity of the user (e.g., running, sleeping, working, biking, hiking, taebo class, fitness class, training session, spin class, yoga, etc.). In another embodiment, wherein for any act of requesting the service by the additional user, the act of requesting further comprises: automatically identifying physical resources and candidate personnel required for the request; coordinating between a plurality of locations and resource availability information associated with required resources and personnel; and wherein the act of coordinating includes executing at least a first API to capture resource availability information from one or more systems executing at at least one of the plurality of locations, reserving, by the first API, the resources identified as required for the request, and confirming the reservation of resources with the one or more systems.

According to one aspect, a computer implemented method for executing multi-tier data and multi-platform data access requests is provided. The method comprises receiving, by at least one processor, biologic data (e.g., heart rate, pulse, respiration, blood pressure, ECG readings, central nervous system readings, etc.) from a first user device (e.g., Jabra pulse, Fitbit, step counter, sleep monitor, etc.) operatively paired with a second user device (e.g., mobile phone, smart phone, portable computing device, etc.) associated with a first user, wherein the first user device collects biologic data and the second user device communicates the biologic data; storing, by the at least one processor, biologic data from the first user as a time series (e.g., capture readings and time) indexed with a known or inferred activity of the user (e.g., running, sleeping, working, biking, hiking, taebo class, fitness class, training session, spin class, yoga, etc.) in a database; associating, by the at least one processor, the biologic data to a plurality of access tiers in the database, the plurality of access tiers including at least a first access tier including the first user, a second access tier including additional users granted electronic permission on the system to access the biologic data by a user associated with the biologic data, and an access tier for administrative functions executed by the system or components; limiting, by the at least one processor, within the second access tier access by the additional users to only the data associated with respective users having given permission on the system; displaying, by the at least one processor, an interface for the additional users to remotely access the system, request services for the first user, receive reports on the first user's biologic data, and access the biologic data for the first user within the interface; wherein for any act of requesting the service by the additional user, the act further comprises: automatically identifying physical resources and candidate personnel required for the request; coordinating between a plurality of locations and resource availability information associated with required resources and personnel, and wherein the act of coordinating includes executing at least a first API to capture resource availability information from one or more systems executing at at least one of the plurality of locations, reserving, by the first API, the resources identified as required for the request, and confirming the reservation of resources with the one or more systems.

Various embodiments of the above methods and method embodiments are implemented with the following refinements and/or elements, which include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, nineteen selections, twenty selections, twenty one selections, twenty two selections, or twenty three selections from the following additional elements or refinements: wherein the method further comprises receiving sensor data from at least the first and second device and storing the sensor data in records with associations to the first user; wherein the method further comprises storing the sensor data with associations to any biologic data received on the first user; wherein the method further comprises: identifying the second device as a registered user device through a unique registration number or digital fingerprint associated with the second user device during registration, and identifying the first user device as a registered user device through a unique registration number or digital fingerprint associated with the first user device during registration or issuance of the first device to the first user; wherein the method further comprises permitting authentication of the user for access to the system responsive to identifying at least one of the first user device or the second user device and denying entry of authentication information in response to failure to identify; wherein the method further comprises: associating the first user with a first user device for collecting biologic data; associating a unique identifier for the first user device with a data record for the first user assigned to the administrative tier; and delivering the first user device to the first user; wherein the method further comprises determining, by at least a second API, an activity executed by the first user based on at least one of: scheduling information stored in the database, resource allocations associated with the first user, personnel allocations associated with the first user, or facility associations associated with the first user; wherein the method further comprises: requesting or receiving, by at least a second API, execution data associated with the first user's second device, wherein the execution data includes information on currently executing applications on the second user device; and inferring a current user activity responsive to analysis of the currently executing application information; wherein the method further comprises: requesting or receiving, by at least a second, telemetric data (e.g., motion, speed, position, elevation, etc.) associated with the first user's second device or first device; and inferring a current user activity responsive to analyzing the telemetric data; wherein analyzing the telemetric data includes comparing received telemetric data, and, optionally, in conjunction with received biologic data, to historic activity and, optionally, the biologic data for the first user; wherein the method further comprises: control data access to the plurality of access tiers and associated biologic information associated with the first user; and maintaining compliance with regulatory requirements for protected health information; wherein the additional user is a trainer granted access by the first user accessing the system through a trainer portal to schedule a fitness activity for the first user; wherein the method further comprises accepting a request from the first user specifying a fitness activity; wherein the method further comprises accepting specification by the first user of additional users able to schedule activities for the first user or view health and fitness data, wherein the method further comprises accepting specification of granular data access (e.g., summary information only, trainer detail access to trainer run sessions only, physician access to all health data, physician access or trainer access to activity information only (e.g., not biologic data capture), etc.); wherein the method further comprises enforcing, by one or more APIs, user specific access restrictions to the user's health information; wherein the method further comprises query available resources across a plurality of systems to match available resources to parameters specified by the user in the request or matching parameters specified in the user's profile; wherein the method further comprises establishing a secure communication session to a trainer specified in the user request, and communicating biologic data captured during the execution of a trainer led activity; wherein the method further comprises communicating over a secure connection the captured biologic data to a remote device associated with the trainer, and communicating over a secure connection the captured biologic data for storage on the system; wherein access to biologic data stored on the system by the trainer is limited to data captured during trainer led activities, responsive to access grant by the first user; wherein access to biologic data stored on the system by the physician is limited responsive to access grant by the first user; wherein the method further comprises accepting user request for fitness activity, and responsive to the user request query available resources (e.g., fitness center locations, fitness equipment, sensor equipment, video equipment, etc.) across a plurality of locations and personnel to determine matching resources for the user request; wherein the method further comprises retrieving user profile preferences associated with the resources (e.g., default location, default trainer (e.g., trainer based on class or activity), etc.) to determine matching resources; wherein the method further comprises presenting matching resources to the user to accept specification of the fitness activity; wherein the method further comprises establishing a secure connection to the first device such that biologic data collection and communication is encrypted between the first device, the second user device, and a database for storing the biologic data; wherein the method further comprises establishing a secure connection between second user device and the database through the secure application such that any data communicated is encrypted between the second device and the database system; and wherein the method further comprises defining an access tier for an insurance provider associated with the first user, wherein the system can accept a first user grant of access for the insurance provider, wherein the access permissions are enforced with a minimum data access acceptable to prove an expense with the provider (e.g., summary information, activity, date, purpose, and value).

According to another aspect, a non-transitory computer-readable medium having computer-readable signals stored thereon that define instructions that, as a result of being executed by a computer, instruct the computer to perform any of the methods, embodiments, or refinements above.

According to one aspect a database system for executing multi-tier data and multi-platform data access requests is provided. The system comprises at least one processor operatively connected to a memory, the at least one processor when executing configured to: integrate with a first user device operatively paired with a second user device associated with a first user, wherein the first user device is configured to receive verbal commands from the first user and communicate verbal commands to the second user device; receive verbal command data from the second user device via a secure application executing on the second user device; authenticate the first user responsive to authentication input received as verbal commands received by the first user device or as input at the second user device through the secure application; prevent acceptance of authentication information until identification of either one or both of the first or second user device as registered user devices, wherein identification is based, at least in part, on a unique registration number or digital fingerprint associated with the first and second user devices; and change execution parameters of the first device or the second device responsive to verbal command data received from the second user device via the secure application.

According to one embodiment, changing the execution parameters of the first device includes at least one of: activating one or more sensors on the first device, deactivating one or more sensors of the first device, changing a data capture rate for the one or more sensors, or changing a data communication rate associated with the one or more sensors. According to another embodiment, the at least one processor is configured to: access a database having an associated plurality of access tiers, the plurality of access tiers including at least a first access tier including the first user, a second access tier including additional users granted electronic permission by the first user on the system to access data associated with the first user, and an access tier for administrative functions executed by the system. According to another embodiment, the at least one processor is configured to: determine an activity executed by the first user based on at least one of scheduling information stored in the database, resource allocations associated with the first user, personnel allocations associated with the first user, or facility associations associated with the first user made accessible through the access tier for administrative functions. According to another embodiment, the at least one processor is configured to: tailor audio prompts to the first user responsive to the determined user activity (e.g., start data capture, start schedule training session, open video connection to trainer, execute fitness program on current resource (e.g., bike, treadmill, stepper, elliptical machine, stair machine, etc.)). Various embodiments, implement tailored audio prompts to the user/device to limit the volume of data required to be transmitted by system elements and to a user, thus preserving bandwidth during execution.

According to one aspect a database system for executing multi-tier data and multi-platform data access requests is provided. The system comprises at least one processor operatively connected to a memory, the at least one processor when executing configured to: integrate with a first user device operatively paired with a second user device associated with a first user, wherein the first user device is configured to receive verbal commands from the first user and communicate verbal commands to the second user device; receive verbal command data from the second user device via a secure application executing on the second user device; authenticate the first user responsive to authentication input received as verbal commands received by the first user device or as input at the second user device through the secure application; prevent acceptance of authentication information until identification of either one or both of the first or second user device as registered user devices, wherein identification is based, at least in part, on a unique registration number or digital fingerprint associated with the first and second user devices; change operational parameters of the first device or the second device responsive to verbal command data received from the second user device via the secure application; wherein changing the execution parameters of the first device includes at least one of: activating one or more sensors on the first device, deactivating one or more sensors of the first device, changing a data capture rate for the one or more sensors, or changing a data communication rate associated with the one or more sensors; access a database having an associated plurality of access tiers, the plurality of access tiers including at least a first access tier including the first user, a second access tier including additional users granted electronic permission by the first user on the system to access data associated with the first user, and an access tier for administrative functions executed by the system; determine an activity executed by the first user based on at least one of scheduling information stored in the database, resource allocations associated with the first user, personnel allocations associated with the first user, or facility associations associated with the first user made accessible through the access tier for administrative functions; and tailor audio prompts to the first user responsive to the determined user activity (e.g., start data capture, start schedule training session, open video connection to trainer, execute fitness program on current resource (e.g., bike, treadmill, stepper, elliptical machine, stair machine, etc.)).

Various embodiments of the above systems and embodiments are implemented with the following refinements and/or element and, include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, or nineteen selections, selections from the following additional system elements or system refinements: wherein the at least one processor is further configured to: interpret verbal command data responsive to the determined user activity to disambiguate the verbal command data (e.g., train—to start training sessions at a time close to a training session, train—connect a current resource video screen to a video training session; train—request a training program to be scheduled; etc.); and execute the interpreted verbal command data according to parameters of the interpreted command; wherein the at least one processor is further configured to tailor audio prompts to the first user responsive to resource allocations associated with the first user, personnel allocations associated with the first user, or facility associations associated with the first user; wherein a first API is configured to received verbal command data and translate the verbal command data into executable commands for a nutrition planning service; Wherein the first API is configured to translate requests for input or prompts for input into audio based requests communicated to either of the first user device or the second user device; Wherein the at least one processor is further configured to: match a current user activity to a set of sensors of at least the first and second user device; activate the set of matching sensors; or match a current user activity to set of sensors associated with at least one scheduled resource, the first device, or second device; and trigger activation of the set of sensors associated with at least one scheduled resource, the first device, or the second device responsive to a verbal command at the first user device; wherein the system further comprises at least a second API configured to access fitness regimen and translate a selected fitness regime into audio instructions for completing the fitness regimen; wherein the at least one processor is further configured to verbalize instructions from a virtual trainer instructing on a system generated fitness program; wherein the verbalized instructions from the virtual trainer are selected from sets of automatically generated fitness instructions, wherein selection is performed automatically by the system responsive to biologic data captured by the first user device; wherein the at least one processor is further configured to: require continued authentication from the first user device or second user device; monitor biologic data being received to permit continued authentication, and absent communication of biologic data terminate an authentication session; wherein the second device establishes a secure connection to the first device such that biologic data collection and communication is encrypted between the first device, the second user device, and a database for storing the biologic data; wherein the second user device establishes a secure connection to the database through the secure application such that any data communicated is encrypted between the second device and the database system; wherein the first user device collects biologic data and the second user device communicates the biologic data to the at least one processor; and the at least one processor is further configured to: store biologic data from the first user as a time series indexed with a known or inferred activity of the user; associate the biologic data to a plurality of access tiers including at least a first access tier with the first user, a second access tier for additional users granted electronic permission on the system to access the biologic data by a user associated with the biologic data, and an access tier from administrative functions executed by the system or components; limit within each access tier access by the additional users to only the data associated with respective users having given permission on the system; wherein the at least one processor is further configured to capture sensor data on the first user including biologic data and associate the biologic data to a plurality of access tiers in the database, the plurality of access tiers including at least a first access tier including the first user, a second access tier including additional users granted electronic permission on the system to access the biologic data by a user associated with the biologic data; wherein the at least one processor is further configured to: display an interface for the additional users to remotely access the system, request services for the first user, receive reports on the first user's biologic data, and access the biologic data associated with the first user within the interface; generate an interface for the first user to remotely access the system; and wherein the at least one processor is further configured to receive sensor data from at least the first and second device and store the sensor data in records associated with the first user; wherein the at least one processor is further configured to store the sensor data with associations to any biologic data received on the first user.

According to one aspect a database system for executing multi-tier data and multi-platform data access requests is provided. The system comprises at least one processor operatively connected to a memory, the at least one processor when executing configured to: integrate with a first user device operatively paired with a second user device associated with a first user, wherein the first user device is configured to receive verbal commands from the first user and communicate verbal commands to the second user device; receive verbal command data from the second user device via a secure application executing on the second user device; authenticate the first user responsive to authentication input received as verbal commands received by the first user device or as input at the second user device through the secure application; prevent acceptance of authentication information until identification of either one or both of the first or second user device as registered user devices, wherein identification is based, at least in part, on a unique registration number or digital fingerprint associated with the first and second user devices; change operational parameters of the first device or the second device responsive to verbal command data received from the second user device via the secure application; wherein changing the execution parameters of the first device includes at least one of: activating one or more sensors on the first device, deactivating one or more sensors of the first device, changing a data capture rate for the one or more sensors, or changing a data communication rate associated with the one or more sensors; access a database having an associated plurality of access tiers, the plurality of access tiers including at least a first access tier including the first user, a second access tier including additional users granted electronic permission by the first user on the system to access data associated with the first user, and an access tier for administrative functions executed by the system; determine an activity executed by the first user based on at least one of scheduling information stored in the database, resource allocations associated with the first user, personnel allocations associated with the first user, or facility associations associated with the first user made accessible through the access tier for administrative functions; interpret verbal command data responsive to the determined user activity to disambiguate the verbal command data (e.g., train—to start training sessions at a time close to a training session, train—connect a current resource video screen to a video training session; train—request a training program to be scheduled; etc.); and execute the interpreted verbal command data according to parameters of the interpreted command. According to various embodiment, interpreting verbal commands based on additional data on the system reduce errors in execution on the system, and further enables tailored execution based on determined context, thereby reducing data entry from the end user (end correspondingly data transmission from the end user) to accomplish the same execution on the system.

In one embodiment, the at least one processor is further configured to tailor audio prompts to the first user responsive to the determined user activity (e.g., start data capture, start schedule training session, open video connection to trainer, execute fitness program on current resource (e.g., bike, treadmill, stepper, elliptical machine, stair machine, etc.)). In another embodiment, the at least one processor is further configured to tailor audio prompts to the first user responsive to resource allocations associated with the first user, personnel allocations associated with the first user, or facility associations associated with the first user.

According to one aspect, a computer implemented method for executing multi-tier data and multi-platform data access requests is provided. The method comprises integrating a first user device operatively paired with a second user device associated with a first user, wherein the first user device is configured to receive verbal commands from the first user and communicate verbal commands to the second user device; receiving, by at least one processor, verbal command data from the second user device via a secure application executing on the second user device; authenticating, by the at least one processor, the first user responsive to authentication input received as verbal commands received by the first user device or as input at the second user device through the secure application; preventing, by the at least one processor, acceptance of authentication information until identification of either one or both of the first or second user device as registered user devices, wherein identification is based, at least in part, on a unique registration number or digital fingerprint associated with the first and second user devices; and changing, by the at least one processor, execution parameters of the first device or the second device responsive to verbal command data received from the second user device via the secure application.

In one embodiment, changing the execution parameters of the first device includes at least one of: activating one or more sensors on the first device, deactivating one or more sensors of the first device, changing a data capture rate for the one or more sensors, or changing a data communication rate associated with the one or more sensors. According to various embodiments, managing execution parameters of the end user devices and/or fitness devices and sensors dynamically, enables the system to reduce processor usage and sensor usage of the peripheral device, and further enables reduced power consumption, and in yet other examples limit communication of data from the peripherals thereby reducing bandwidth consumption by the system when executing. In another embodiment, accessing, by the at least one processor, a database having an associated plurality of access tiers, the plurality of access tiers including at least a first access tier including the first user, a second access tier including additional users granted electronic permission by the first user on the system to access data associated with the first user, and an access tier for administrative functions executed by the system. In some examples, the plurality of access tier improve security in the data and execution of access control.

In another embodiment, the method further comprises determining, by the at least one processor, an activity executed by the first user based on at least one of scheduling information stored in the database, resource allocations associated with the first user, personnel allocations associated with the first user, or facility associations associated with the first user made accessible through the access tier for administrative functions. In another embodiment, the method further comprises tailoring, by the at least one processor, audio prompts to the first user responsive to the determined user activity (e.g., start data capture, start schedule training session, open video connection to trainer, execute fitness program on current resource (e.g., bike, treadmill, stepper, elliptical machine, stair machine, etc.)).

According to one aspect, a computer implemented method for executing multi-tier data and multi-platform data access requests is provided. The method comprises integrating a first user device operatively paired with a second user device associated with a first user, wherein the first user device is configured to receive verbal commands from the first user and communicate verbal commands to the second user device; receiving, by at least one processor, verbal command data from the second user device via a secure application executing on the second user device; authenticating, by the at least one processor, the first user responsive to authentication input received as verbal commands received by the first user device or as input at the second user device through the secure application; preventing, by the at least one processor, acceptance of authentication information until identification of either one or both of the first or second user device as registered user devices, wherein identification is based, at least in part, on a unique registration number or digital fingerprint associated with the first and second user devices; changing, by the at least one processor, execution parameters of the first device or the second device responsive to verbal command data received from the second user device via the secure application; wherein changing the execution parameters of the first device includes at least one of: activating one or more sensors on the first device, deactivating one or more sensors of the first device, changing a data capture rate for the one or more sensors, or changing a data communication rate associated with the one or more sensors; accessing, by the at least one processor, a database having an associated plurality of access tiers, the plurality of access tiers including at least a first access tier including the first user, a second access tier including additional users granted electronic permission by the first user on the system to access data associated with the first user, and an access tier for administrative functions executed by the system; determining, by the at least one processor, an activity executed by the first user based on at least one of scheduling information stored in the database, resource allocations associated with the first user, personnel allocations associated with the first user, or facility associations associated with the first user made accessible through the access tier for administrative functions; and tailoring, by the at least one processor, audio prompts to the first user responsive to the determined user activity (e.g., start data capture, start schedule training session, open video connection to trainer, execute fitness program on current resource (e.g., bike, treadmill, stepper, elliptical machine, stair machine, etc.)).

Various embodiments of the above methods and method embodiments are implemented with the following refinements and/or elements, and include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, or nineteen selections from the following additional method elements or method refinements: wherein the method further comprises: interpreting verbal command data responsive to the determined user activity to disambiguate the verbal command data (e.g., train—to start training sessions at a time close to a training session, train—connect a current resource video screen to a video training session; train—request a training program to be scheduled; etc.); and executing the interpreted verbal command data according to parameters of the interpreted command; wherein the method further comprises: tailoring audio prompts to the first user responsive to resource allocations associated with the first user, personnel allocations associated with the first user, or facility associations associated with the first user; wherein the method further comprises receiving, by a first API, verbal command data and translating the verbal command data into executable commands for a nutrition planning service; wherein the method further comprises translating, by a first API, requests for input or prompts for input into audio based requests communicated to either of the first user device or the second user device; wherein the method further comprises: matching a current user activity to a set of sensors of at least the first and second user device; activating the set of matching sensors; or matching a current user activity to set of sensors associated with at least one scheduled resource, the first device, or second device; and triggering activation of the set of sensors associated with at least one scheduled resource, the first device, or the second device responsive to a verbal command at the first user device; wherein the method further comprises accessing, by at least a second API, fitness regimen and translating a selected fitness regime into audio instructions for completing the fitness regimen; wherein the method further comprises: verbalizing instructions from a virtual trainer instructing on a system generated fitness program; wherein the method further comprises selecting the verbalized instructions from the virtual trainer from sets of automatically generated fitness instructions, wherein the act of selecting is performed automatically by the system responsive to biologic data captured by the first user device; wherein the method further comprises: requiring continued authentication from the first user device or second user device; monitoring biologic data being received to permit continued authentication; and terminating an authentication session absent communication of biologic data; wherein method further comprises establishing a secure connection with the second device and the first device such that biologic data collection and communication is encrypted between the first device, the second user device, and a database for storing the biologic data; wherein method further comprises establishing a secure connection with the second device and the database through the secure application such that any data communicated is encrypted between the second device and the database system; wherein the first user device collects biologic data and the second user device communicates the biologic data to the at least one processor; and the method further comprises: storing biologic data from the first user as a time series indexed with a known or inferred activity of the user; associating the biologic data to a plurality of access tiers including at least a first access tier with the first user, a second access tier for additional users granted electronic permission on the system to access the biologic data by a user associated with the biologic data, and an access tier from administrative functions executed by the system or components; limiting within each access tier access by the additional users to only the data associated with respective users having given permission on the system; wherein the method further comprises: capturing sensor data on the first user including biologic data and associate the biologic data to a plurality of access tiers in the database, the plurality of access tiers including at least a first access tier including the first user, a second access tier including additional users granted electronic permission on the system to access the biologic data by a user associated with the biologic data; wherein the method further comprises: displaying an interface for the additional users to remotely access the system, request services for the first user, receive reports on the first user's biologic data, and access the biologic data for the first user within the interface; generating an interface for the first user to remotely access the system; wherein the method further comprises: receiving sensor data from at least the first and second device and store the sensor data in records associated with the first user; and wherein the method further comprises: storing the sensor data with associations to any biologic data received on the first user.

According to one aspect, a computer implemented method for executing multi-tier data and multi-platform data access requests is provided. The method comprises integrating with a first user device operatively paired with a second user device associated with a first user, wherein the first user device is configured to receive verbal commands from the first user and communicate verbal commands to the second user device; receiving, by at least one processor, verbal command data from the second user device via a secure application executing on the second user device; authenticating, by the at least one processor, the first user responsive to authentication input received as verbal commands received by the first user device or as input at the second user device through the secure application; preventing, by the at least one processor, acceptance of authentication information until identification of either one or both of the first or second user device as registered user devices, wherein identification is based, at least in part, on a unique registration number or digital fingerprint associated with the first and second user devices; changing, by the at least one processor, execution parameters of the first device or the second device responsive to verbal command data received from the second user device via the secure application; wherein changing the execution parameters of the first device includes at least one of: activating one or more sensors on the first device, deactivating one or more sensors of the first device, changing a data capture rate for the one or more sensors, or changing a data communication rate associated with the one or more sensors; accessing a database having an associated plurality of access tiers, the plurality of access tiers including at least a first access tier including the first user, a second access tier including additional users granted electronic permission by the first user on the system to access data associated with the first user, and an access tier for administrative functions executed by the system; determining, by the at least one processor, an activity executed by the first user based on at least one of scheduling information stored in the database, resource allocations associated with the first user, personnel allocations associated with the first user, or facility associations associated with the first user made accessible through the access tier for administrative functions; and interpreting, by the at least one processor, verbal command data responsive to the determined user activity to disambiguate the verbal command data (e.g., train—to start training sessions at a time close to a training session, train—connect a current resource video screen to a video training session; train—request a training program to be scheduled; etc.); and executing, by the at least one processor, the interpreted verbal command data according to parameters of the interpreted command.

According to one embodiment, the method further comprises: tailor audio prompts to the first user responsive to the determined user activity (e.g., start data capture, start schedule training session, open video connection to trainer, execute fitness program on current resource (e.g., bike, treadmill, stepper, elliptical machine, stair machine, etc.)). According to one embodiment, the method further comprises: tailoring audio prompts to the first user responsive to resource allocations associated with the first user, personnel allocations associated with the first user, or facility associations associated with the first user.

According to another aspect, a non-transitory computer-readable medium having computer-readable signals stored thereon that define instructions that, as a result of being executed by a computer, instruct the computer to perform any of the methods, embodiments, or refinements above.

According to one aspect a database system for executing multi-tier data and multi-platform data access requests is provided. The system comprises at least one processor operatively connected to a memory, the at least one processor when executing configured to: execute a first API configured to capture biologic data for a first user from at least one of: a first user device for monitoring health data, a second user device (e.g., mobile computing device) configured to pair with any one or more health monitoring devices, or a remote resource at a fitness center; execute a second API configured to integrate physician systems and provide an interface for physician access to the first user's biologic data, wherein the second API is configured to limit access responsive to the first user providing electronic confirmation of access privileges to the first user's biologic data for a specific physician or physician group; execute a third API configured to provide trainer access to the first user's data, wherein the third API is configured to limit trainer access to biologic data collected in real time during a training sessions or to historic biologic data collected during a training session conducted by a specific trainer or trainer group; execute a fourth API configured to access a plurality of fitness center systems to capture resource information and availability information associated with the resources, and reserve the resources responsive to a scheduling request; and a scheduling component, executed by the at least one processor, configured to interface with a plurality of APIs (e.g., first, second, third, and fourth) to coordinate scheduling between at least one or combination of: a user undertaking a fitness activity, a trainer or physician to guide the fitness activity, fitness resources necessary for the fitness activity, a fitness center and internal location in which to conduct the fitness activity; and wherein the scheduling component is further configured to trigger respective systems to allocate the respective resources and personnel to execute the fitness activity.

According to one aspect a database system for executing multi-tier data and multi-platform data access requests is provided. The system comprises at least one processor operatively connected to a memory, the at least one processor when executing configured to: execute at least a first API configured to: capture biologic data for a first user from at least one of: a first user device for monitoring health data, a second user device (e.g., mobile computing device) configured to pair with any one or more health monitoring devices, or a remote resource at a fitness center; execute at least a second API configured to: integrate physician systems and provide an interface for physician access to the first user's biologic data, wherein the second API is configured to limit access responsive to the first user providing electronic confirmation of access privileges to the first user's biologic data for a specific physician or physician group; manage trainer access to the first user's data, wherein the third API is configured to limit trainer access to biologic data collected in real time during a training sessions or to historic biologic data collected during a training session conducted by a specific trainer or trainer group; and access a plurality of fitness center systems to capture resource information and availability information associated with the resources, and reserve the resources responsive to a scheduling request; and a scheduling component, executed by the at least one processor, configured to interface with a plurality of APIs (e.g., first, second, third, and fourth) to coordinate scheduling between at least one or combination of: a user undertaking a fitness activity, a trainer or physician to guide the fitness activity, fitness resources necessary for the fitness activity, a fitness center and internal location in which to conduct the fitness activity; and wherein the scheduling component is further configured to trigger respective systems to allocate the respective resources and personnel to execute the fitness activity.

Various embodiments of the above systems and embodiments, are implemented with the following refinements and/or elements, which include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, or nineteen selections from the following additional system elements and/or system refinements: wherein the at least one processor is further configured to receive sensor data (e.g., heart rate, acceleration, GPS, motion, audio, video, etc.) from at least the first and second device and store the sensor data in records with associations to the first user; wherein the at least one processor is further configured to store the sensor data with associations to the first user, including any biologic data received on the first user; wherein the at least one processor is provisioned from a cloud compute resource providers (e.g., Amazon AWS, GOOGLE cloud, etc.); wherein the scheduling component is configured to generate a user interface configured to display a plurality of candidate schedules aligning the user, the trainer or physician, the fitness resources, including the fitness centers in a single display page or as audio based prompts communicated to a user device; wherein the system further comprises at least a third API configured to integrate at least data capture from the fitness resources scheduled for the fitness activity; wherein the system further comprises at least one mobile application executable on a remote device configured to provide access to the physician accessible portal; wherein the plurality of APIs further comprise a meal planning API configured to capture physician defined nutrition restrictions, and automatically trigger generation of a meal plan consistent with the physician defined restrictions; wherein the physician defined restriction includes a no vitamin K restriction, and the meal plan API is configured to trigger automatic execution of a meal planning program and capture of the generated meal plan, wherein the meal plan excludes food having vitamin K; wherein the system further comprises a health insurance API configured to integrate at least one health insurance provider by capturing coverage information for at least one client and automatically facilitating reimbursement; wherein the health insurance API manages automatic creation and submission of a reimbursement request to the user's health insurance provider; wherein the system manages a reimbursement request for fitness devices or medical devices that remotely monitor client health information; wherein the system further comprises at least a third API configured to: secure communication channels to communicate the users' health information (e.g., pulse rate, fitness activity, verbal commands) from the fitness devices or health monitoring devices; and receive from the fitness devices or the health monitoring devices at least biologic data; wherein the system further comprises a verbal command interface configured to control system function responsive to client verbal input; wherein the verbal command interface includes client monitoring sensors configured to capture health data on the client; wherein the system further comprises at least a third API configured to access fitness regimen and translate a selected fitness regimen into audio instructions for completing the fitness regimen; wherein at least the third API is further configured to verbalize instructions from a virtual trainer as audio cues instructing on a system generated fitness program; wherein the verbalized instructions from the virtual trainer are selected dynamically from sets of automatically generated fitness instructions, wherein selection is performed automatically by the system responsive to biologic data captured by the first user device; wherein the at least one processor is further configured to: display an interface for the additional users to remotely access the system, request services for the first user, receive reports on the first user's biologic data, and access the biologic data for the first user within the interface; and generate an interface for the first user to remotely access the system; wherein the first user device collects biologic data and the second user device communicates the biologic data to the at least one processor; and the at least one processor is further configured to: store biologic data from the first user as a time series indexed with a known or inferred activity of the user; associate the biologic data to a plurality of access tiers including at least a first access tier with the first user, a second access tier for additional users granted electronic permission on the system to access the biologic data by a user associated with the biologic data, and an access tier from administrative functions executed by the system or components; and limit within each access tier access by the additional users to only the data associated with respective users having given permission on the system; and wherein the at least one processor is further configured to: require continued authentication from the first user device or second user device; monitor biologic data being received to permit continued authentication, and absent communication of biologic data terminate an authentication session.

According to one aspect, a computer implemented method for executing multi-tier data and multi-platform data access requests is provided. The method comprises capturing, by a first API, biologic data for a first user from at least one of: a first user device for monitoring health data, a second user device (e.g., mobile computing device) configured to pair with any one or more health monitoring devices, or a remote resource at a fitness center; integrating, by a second API, physician systems and provide an interface for physician access to the first user's biologic data, including an act of limiting access responsive to the first user providing electronic confirmation of access privileges to the first user's biologic data for a specific physician or physician group; providing, by a third API, trainer access to the first user's data, including an act of limiting trainer access to biologic data collected in real time during a training sessions or to historic biologic data collected during a training session conducted by a specific trainer or trainer group; accessing, by a fourth API, a plurality of fitness center systems to capture resource information and availability information associated with the resources, and reserving the resources responsive to a scheduling request; and coordinating, by a scheduling component, between a plurality of APIs (e.g., first, second, third, and fourth) to schedule between at least one or combination of: a user undertaking a fitness activity, a trainer or physician to guide the fitness activity, fitness resources necessary for the fitness activity, a fitness center and internal location in which to conduct the fitness activity, and triggering, by the scheduling component, respective systems to allocate the respective resources and personnel to execute the fitness activity.

According to one aspect, a computer implemented method for executing multi-tier data and multi-platform data access requests is provided. The method comprises capturing, by at least a first API, biologic data for a first user from at least one of: a first user device for monitoring health data, a second user device (e.g., mobile computing device) configured to pair with any one or more health monitoring devices, or a remote resource at a fitness center; integrating, by at least a second API, physician systems and provide an interface for physician access to the first user's biologic data, including an act of limiting access responsive to the first user providing electronic confirmation of access privileges to the first user's biologic data for a specific physician or physician group; providing, by the at least the second API, trainer access to the first user's data, including an act of limiting trainer access to biologic data collected in real time during a training sessions or to historic biologic data collected during a training session conducted by a specific trainer or trainer group; accessing, by the at least the second API, a plurality of fitness center systems to capture resource information and availability information associated with the resources, and reserving the resources responsive to a scheduling request; and coordinating, by a scheduling component, between a plurality of APIs (e.g., first, second, third, and fourth) to schedule between at least one or combination of: a user undertaking a fitness activity, a trainer or physician to guide the fitness activity, fitness resources necessary for the fitness activity, a fitness center and internal location in which to conduct the fitness activity, and triggering, by the scheduling component, respective systems to allocate the respective resources and personnel to execute the fitness activity.

Various embodiments of the above methods and method embodiments, include any one selection, two selections, three selections, four selections, five selections, six selections, seven selections, eight selections, nine selections, ten selections, eleven selections, twelve selections, thirteen selections, fourteen selections, fifteen selections, sixteen selections, seventeen selections, eighteen selections, nineteen selections, twenty selections, twenty one selections, twenty two selections, or twenty three selections from the following additional method elements or method refinements: wherein the method further comprises receive sensor data (e.g., heart rate, acceleration, GPS, motion, audio, video, etc.) from at least the first and second device and store the sensor data in records with associations to the first user; wherein the method further comprises store the sensor data with associations to the first user, including any biologic data received on the first user; wherein the method further comprises an act of provisioning a plurality of APIs from a cloud compute resource providers (e.g., Amazon AWS, GOOGLE cloud, etc.); wherein the method further comprises generating, by the scheduling component, a user interface configured to display a plurality of candidate schedules aligning the user, the trainer or physician, the fitness resources, including the fitness centers in a single display page or as audio based prompts communicated to a user device; wherein the method further comprises integrating, by at least a third API, at least data capture from the fitness resources scheduled for the fitness activity; wherein the method further comprises providing access to the physician accessible portal via at least one mobile application on a remote device; wherein the method further comprises capturing physician defined nutrition restrictions via a meal planning API, and automatically triggering generation of a meal plan consistent with the physician defined restrictions; wherein the physician defined restriction includes a no vitamin K restriction, wherein the method further comprises triggering automatic execution of a meal planning program and capturing of the generated meal plan, wherein the meal plan excludes food having vitamin K; wherein the method further comprises: integrating, at least one health insurance provider with a health insurance API; capturing coverage information for at least one client; and automatically facilitating reimbursement; wherein the method further comprises managing, by the health insurance API, automatic creation and submission of a reimbursement request to the user's health insurance provider; wherein the method further comprises managing a reimbursement request for fitness devices or medical devices that remotely monitor client health information; wherein the method further comprises: securing, by at least a third API, communication channels to communicate the users' health information (e.g., pulse rate, fitness activity, verbal commands) from the fitness devices or health monitoring devices; and receiving from the fitness devices or the health monitoring devices at least biologic data; wherein the method further comprises controlling system function responsive to client verbal input by a verbal command interface; wherein the method further comprises capturing health data on the client via client monitoring sensors configured to capture health data on the client; wherein the method further comprises accessing, by at least a fourth API, a fitness regimen and translating a selected fitness regimen into audio instructions for completing the fitness regimen; wherein the method further comprises verbalizing instructions from a virtual trainer as audio cues instructing on a system generated fitness program; wherein the verbalized instructions from the virtual trainer are selected dynamically from sets of automatically generated fitness instructions, and wherein an act of selecting is performed automatically by the system responsive to biologic data captured by the first user device; wherein the method further comprises: displaying an interface for the additional users to remotely access the system, request services for the first user, receive reports on the first user's biologic data, and access the biologic data for the first user within the interface; generating an interface for the first user to remotely access the system; wherein the first user device collects biologic data and the second user device communicates the biologic data to the at least one processor; and the method further comprises: storing biologic data from the first user as a time series indexed with a known or inferred activity of the user; associating the biologic data to a plurality of access tiers including at least a first access tier with the first user, a second access tier for additional users granted electronic permission on the system to access the biologic data by a user associated with the biologic data, and an access tier from administrative functions executed by the system or components; and limiting within each access tier access by the additional users to only the data associated with respective users having given permission on the system; and wherein the method further comprises: requiring continued authentication from the first user device or second user device; monitoring biologic data being received to permit continued authentication, and terminating an authentication session absent communication of biologic data.

According to another aspect, a non-transitory computer-readable medium having computer-readable signals stored thereon that define instructions that, as a result of being executed by a computer, instruct the computer to perform any of the methods, embodiments, or refinements above.

According to one aspect a database system for executing multi-tier data and multi-platform data access requests is provided. The system comprises at least one processor operatively connected to a memory, the at least one processor when executing configured to: integrate with a first user device operatively paired with a second user device associated with a first user, wherein the first user device is configured to receive verbal commands from the first user and communicate with a secure application installed on the second device; receive interpreted verbal command data communicated from the second user device via a secure application executing on the second user device; authenticate the first user responsive to authentication input received as verbal commands received by the first user device or as input at the second user device through the secure application; prevent acceptance of authentication information until identification of either one or both of the first or second user device as registered user devices, wherein identification is based, at least in part, on a unique registration number or digital fingerprint associated with the first and second user devices; continue authentication of the first user responsive to receiving biologic data originating from the first user device, wherein the at least one processor is further configured to continue an authentication session in response to determining that the received biologic data matches a pattern of biologic data (e.g., pattern of heart rate, pattern on heart rate and respiration, pattern on CNS (central nervous system) date, pattern on CNS and heart rate, pattern on CNS, heart rate, and respiration, pattern on ECG data, pattern on ECG, heart rate, pattern on ECG, heart rate, and respiration, pattern on ECG heart rate CNS data, pattern on any combination of heart rate, respiration, CNS data, ECG data—and wherein the preceding patterns are generated over periods of time) stored for the first user over a threshold time period (e.g., 1 sec., 2 seconds, 3 seconds, 4 seconds, 5 seconds, etc.) and terminate an authentication session responsive to a failed match.

According to one aspect a database system for executing multi-tier data and multi-platform data access requests is provided. The system comprises at least one processor operatively connected to a memory, the at least one processor when executing configured to: Integrate with a first user device operatively paired with a second user device associated with a first user, wherein the first user device is configured to communicate with a secure application installed on the second device; receive verbal command data communicated from the first user device via an embedded processor component on the first user device, wherein the first user device is configured to receive and process verbal commands from an end user; authenticate the first user responsive to authentication input received as verbal commands received by the first user device or as input at the second user device through the secure application; prevent acceptance of authentication information until identification of either one or both of the first or second user device as registered user devices, wherein identification is based, at least in part, on a unique registration number or digital fingerprint associated with the first and second user devices; continue authentication of the first user responsive to receiving biologic data originating from the first user device, wherein the at least one processor is further configured to continue authentication in response to determining that the received biologic data matches a pattern of biologic data (e.g., pattern of heart rate, pattern on heart rate and respiration, pattern on CNS (central nervous system) date, pattern on CNS and heart rate, pattern on CNS, heart rate, and respiration, pattern on ECG data, pattern on ECG, heart rate, pattern on ECG, heart rate, and respiration, pattern on ECG heart rate CNS data, pattern on any combination of heart rate, respiration, CNS data, ECG data—and wherein the preceding patterns are generated over periods of time) stored for the first user over a threshold time period (e.g., 1 sec., 2 seconds, 3 seconds, 4 seconds, 5 seconds, etc.) and terminate an authentication session responsive to a failed match.

According to some embodiments of the preceding systems, the first communication server is instantiated at a cloud provider, and the at least one processor is further configured to integrate the first and second user device based on execution of a registration process that identifies communication protocols for reaching the cloud instantiated first communication server. According to some embodiments of the preceding systems, the first communication server is further configured to update the secure application installed on the second device with updated communication information responsive to configuration changes associated with resources provisioned at the cloud provider.

According to some embodiments of the preceding systems, the systems further comprise a database having an associated plurality of access tiers, the plurality of access tiers including at least a first access tier including the first user, a second access tier including additional users granted electronic permission by the first user on the system to access data associated with the first user, and an access tier for administrative functions executed by the system; wherein the at least one processors executes an authentication protocol having an administrative function access association. According to some embodiments of the preceding systems, responsive to determining the authentication protocol includes the administrative function access association, the authentication protocol is permitted to access stored biologic data associated with the first user to establish the biologic pattern for authentication.

According to some embodiments of the preceding systems, the systems further comprise a health insurer API configured to automatically build re-imbursement requests to a user's health insurer. According to some embodiments of the preceding systems, the health insurer API is further configured to automatically submit and track reimbursement requests. According to some embodiments of the preceding systems, the health insurer API is further configured to monitor progress on the health insurance provider's system via API integration. According to some embodiments of the preceding systems, the health insurer API is further configured to predict reimbursable requests. According to some embodiments of the preceding systems, the health insurer API is further configured to automatically prepare reimbursable request and communicate the request to physician system for submission to health insurance provider. According to some embodiments of the preceding systems, the health insurer API is further configured to automatically prepare reimbursable request and communicate the request to veteran administration systems.

According to one aspect a database system for executing multi-tier data and multi-platform data access requests is provided. The system comprises at least one processor operatively connected to a memory, the at least one processor when executing configured to: integrate with a first user device operatively paired with a second user device associated with a first user, wherein at least one of the first user device and second device is configured to capture biologic data on the first user; and authenticate the first user responsive to receiving biologic data originating from the first user device or second user device, wherein the at least one processor is further configured to authenticate the first user in response to determining that the received biologic data matches a pattern of biologic data (e.g., pattern of heart rate, pattern on heart rate and respiration, pattern on CNS (central nervous system) date, pattern on CNS and heart rate, pattern on CNS, heart rate, and respiration, pattern on ECG data, pattern on ECG, heart rate, pattern on ECG, heart rate, and respiration, pattern on ECG heart rate CNS data, pattern on any combination of heart rate, respiration, CNS data, ECG data—and wherein the preceding patterns are generated over periods of time) stored for the first user over a threshold time period (e.g., 1 sec., 2 seconds, 3 seconds, 4 seconds, 5 seconds, etc.) and deny authentication responsive to a failed match.

According to another aspect, computer implemented methods are provided to executed the preceding system functions, embodiments operations, or refinement procedures above. According to another aspect, a non-transitory computer-readable medium having computer-readable signals stored thereon that define instructions that, as a result of being executed by a computer, instruct the computer to perform any of the system functions, embodiments operations, or refinement procedures above. According to another aspect, a non-transitory computer-readable medium having computer-readable signals stored thereon that define instructions that, as a result of being executed by a computer, instruct the computer to perform any of the methods above.

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 15A is a screenshot image, according to one embodiment;

FIG. 15B is a screenshot image, according to one embodiment;

DETAILED DESCRIPTION

Various embodiments implement a multiplatform system architected to provide secure messaging between a plurality of disparate systems (e.g., mobile devices, secure cloud systems, remote locations, health monitoring devices, fitness centers, etc.), co-ordinate resources associated with each of the disparate systems, manage communication between proprietary applications via customized application programming interfaces (APIs) and manage reservation of resources of the disparate systems via the APIs. Further embodiments enable an extensible system architecture to incorporate additional systems.

In some embodiments, the system includes a multi-layered database architecture to mediate information and access control (e.g., based on inheritable privileges, specific user classes are allowed or denied access to data in the database). In further embodiments, the data architecture is architected with access layers that ensure HIPAA compliance and/or compliance with the HITECH Act and other regulatory schemes. Any sensor data (e.g., biologic, biometric, positional, tracking, etc.) can be captured by sensors on remote systems, correlated with users and stored securely as described herein, for example as described with respect to biologic data.

Examples of the methods, devices, and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 1A:
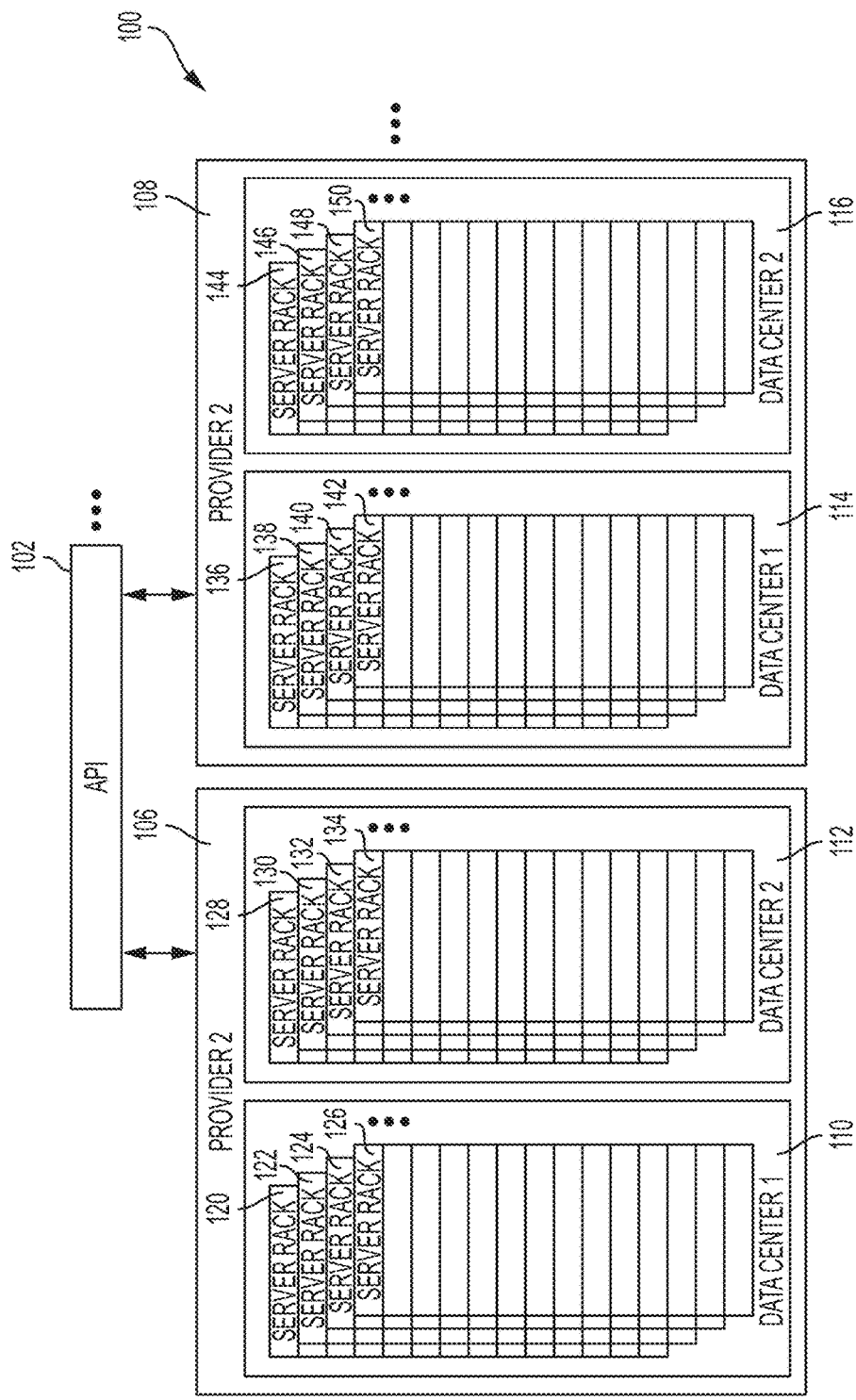
FIG. 1A is a block diagram of a cloud compute environment and central system API, according to one embodiment.

FIG. 1A is an example block diagram of a cloud compute environment 100. Shown on FIG. 1A are a plurality of cloud compute providers (e.g., 106 and 108). An application program interface (API) 102 (or, for example, a plurality of APIs) can be instantiated on the cloud compute environment 100. The API 102 can be configured, for example, to manage information capture from health monitoring devices, and manage registering and pairing of user mobile phone and respective health monitoring devices (and also data capture from the user device sensors). In further examples, the API 102 can be instantiated as part of a cloud compute platform, which can also include a scheduling system (e.g., 180, FIG. 1C—discussed below). In one example, API 102 can be configured to manage integration with a variety of remote systems and/or remote services. The API 102 can be configured to capture information on remote systems (e.g., fitness center systems, physician systems, nutrition planning systems, etc.) and translate requests from the scheduling system to the remote systems. Through the API 102 various resources (and respective scheduled) can be managed, integrated, and executed in coordination. In various embodiments, API 102 can be implemented a single API that performs the discussed functions or can be implemented as multiple APIs that each perform operations between pairs of systems and the multiple APIs collectively implement API 102.

In other embodiments, the API 102 and/or the scheduling system (e.g., 180, FIG. 1C—discussed below) can be executed within a private cloud or local computing resources. As shown in FIG. 1A, each of the plurality of providers (e.g., 106 and 108) host a plurality of resources and underlying servers/server racks (e.g., 120-150) that can be provisioned to service scheduling systems, remote systems (e.g., physician systems, fitness center systems, trainer systems/application, etc.), pairing with mobile devices and/or heath monitoring devices, manage remotely executed fitness activities (e.g., bridge video and/or sensor systems at fitness centers and/or on fitness devices into etc.

In some examples, each provider can host numerous servers/server racks at a plurality of organizational units (for convenience, referred to as "data centers", although some provider's physical data centers may encompass multiple units) (e.g., 110-116) and provision available resources from any such location.

In some embodiments, API 102 can also be provisioned from one or more of the plurality of providers. In further embodiments, API 102 can also be configured to operate as a network or web based interface for managing scheduling of resources, hosting a multi-tier database, capturing biologic data from users (or any sensor data), providing physician access to respective patients' health and fitness data, coordinate physical therapy session with trainers and fitness centers, coordinate fitness sessions with trainers, fitness centers, and/or fitness equipment.

Users, physicians, trainers, and/or fitness center technical administrators can access API 102 via a web portal or web API, and use API 102 to manage scheduling, privacy settings of health data (e.g., the system ensured HIPAA compliance). In other embodiments, the integration of the various systems through API 102 enables richer data sets, and improved automatic predictive capabilities of the system. For example, fitness planning tailored to a specific user can be automatically generated on the system and even executed automatically with the end user based on predictive fitness session planning.

Figure 1B:
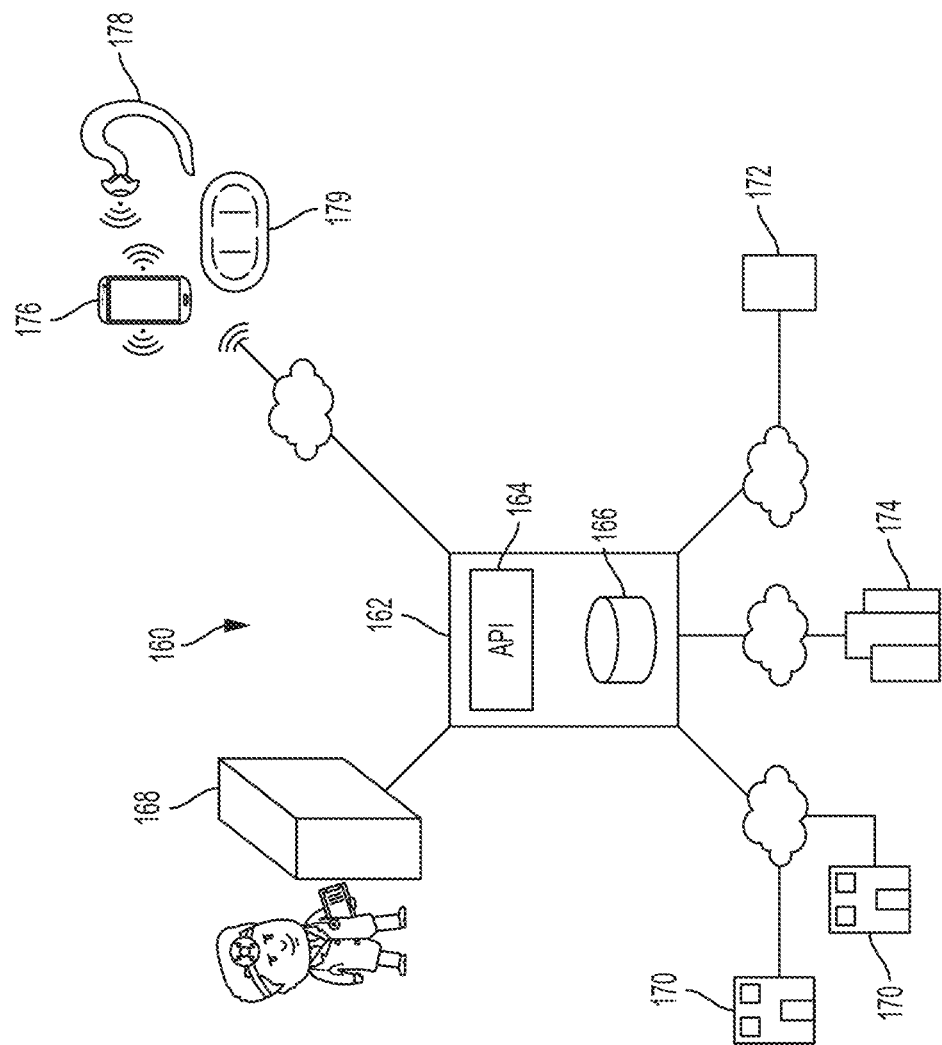
FIG. 1B is a block diagram of environment and integrated systems, according to one embodiment.

FIG. 1B is an example implementation environment 160 including a central scheduling system 162. The central scheduling system 162 can include one or more APIs (e.g., 164) that can collectively and/or individually communicate with various remote system to enable the central scheduling system 162 to manage schedules and resources across any connected system. Even in some example to provide for further extensibility and integration with new systems. The central scheduling system 162 can include a multi-tier database 166 configured to host medical and/or health information for respective users and manage review of the same information by physicians, trainers (e.g., portions of the health information), scheduling, and authentication processes while preserving privacy of the data in compliance with HIPAA and the HITECH Act governing protected health information.

According to one embodiment, the multi-tier database includes access layers or tiers organized to preserve privacy rights in protected health information. For example, the multi-tiered database can include at least a first tier associated with users and, for example, respective health information stored on the system. A second tier of the database can be associated with Primary Care Physicians ("PCP") or other health providers. The second tier of the database can be managed by the system to require permission from respective users in order for the physicians to be able to access health information associated with users. Once a user provides permission on the system the respective physician can access the user's health information (e.g., fitness activity, biologic sensor reading data, training program, fitness program, nutrition plan, nutrition restrictions, etc.). In other embodiments, the user can provide permission to physician practice groups or other health providers to access their health information.

Other access tiers can manage data access by trainers, for example, to fitness sessions with respective users. In some embodiments, trainers can be given access to biologic data collected during fitness activities that they conduct and/or direct. Trainer access privileges can be more limited that physician level access in terms of access to health data (e.g., limited to active training sessions- and summary information provided thereafter).

In further embodiments, trainer access privileges can be used with respect to specific fitness centers, fitness center resources (e.g., fitness equipment, training equipment, classrooms, etc.), so that a trainer can schedule classes and resources across a plurality of fitness centers. In one example, a trainer can access a central scheduling system to reserve fitness equipment for remote classes and have the central scheduling system handle video connections for each user and respective reserved equipment. Another access tier in the database, services data access requests by administrative processes (e.g., a scheduling and/or coordination process need access to remote systems, remote calendar information, definition of resources and availability at various fitness centers, etc.) and administrator of the overall system. According to one embodiment, at least two types of administrators (and respective defined access roles) are configured on the system with respective access rights to available data—local administrators of respective systems and associated data (e.g., fitness center administrators have access rights to define, manage, and change resources at the fitness center (e.g., add trainers, add equipment etc.))—and super administrators (e.g., system administrators and processes) have rights and access granted to system administrators and have administrative privileges on all aspects of the system and integrated systems (e.g., at least to the extent of integrated components and data access on the system).

As discussed above a plurality of users can participate on the system to track health information, have a central repository for sensor data and/or health data captured by user health monitoring devices, received the benefit of physician review of collected health data (and, for example, tailored to the level of access the user designates on the system for their physician to have (e.g., via physician portals and or integrated physician systems), include trainer expertise in review of their collected health data (e.g., even during collection of the health data or training session—where trainer access can also be tailored to the level the user designated on the system (e.g., review sessions run by trainer, or at a fitness center, summary information on other, fitness activity, etc.)) and trainer expertise in crafting exercise programs (e.g., via a trainer portal, secure application installed on the trainer's computing devices or via fitness center systems (e.g., 170), etc.). while maintaining health regulation compliance (e.g., via trainer's computing devices).

In further embodiments, each user can be provided predictive fitness regimens and/or fitness regimens created based on machine learning analysis of similar routines, similar users, matching fitness patterns, matching biologic data patterns, etc. In some embodiments, the system automatically generates a virtual trainer to take the user through the automatically created fitness program (e.g., virtualized audio instruction and tailored encouragement instructions during fitness sessions, etc.). The system can manage any number of virtual trainers across any number of users by instantiating, for example, additional cloud resources on demand. Further the system can manage connections to users devices and/or fitness equipment and separate physical locations (e.g., different fitness centers) to delivery virtualized video instruction and/or audio instruction based on the system generated fitness plan.

In further embodiments, fitness planning and management is further augmented by integrated nutrition planning systems (e.g., 172). In one embodiment, physicians can enter nutrition goals and/or restrictions, and an integrated meal planning system can develop meal plans for users incorporating physician directed restrictions. In further examples, the nutrition system can capture additional information on historic fitness performance (e.g., caloric burn during fitness activities, and/or average calorie consumption during workouts or fitness activity) to fine tune meal plans to specific users. In further embodiments, the nutrition system can analyze historic fitness activity and/or future scheduled activities to tailor meal plans specifically to expected physical activity and caloric use. According to some embodiments, physicians and/or trainers can review meal plans for respective users and adjust the meal plans or confirm the plan accordingly via the integrated nutrition planning system.

According to one embodiment, a user can register to participate with the system. The user can download a secure application from the system and use the secure application to register their device (e.g., 176). For example, the system can capture a digital fingerprint of the user's device to establish a unique identity of the device. Other unique information can be captured from the device to establish a unique identifier for the user's device (e.g., serial number, IMEI number, or other assigned identifier for the device). In other embodiments, a subscribing user can be issued a health monitoring device (e.g., 178)(e.g., JABRA PULSE, etc.) by the system. Where the system issues a health monitoring device, unique identifying information for the device can be captured and associated with the user at issuance. In further embodiments, other health monitoring devices (e.g., 179— SKULPT for measuring body fat, muscle quality, etc.) can be paired with a user's computing device via the secure application. The secure application can also be configured to capture identifying information for the other health monitoring device and register them for use on the system.

According to another aspect, the system can monitor user fitness activity and link fitness activity to health insurance programs and/or wellness programs. For example, purchase of a health monitoring device can be a reimbursable expense. The system can include integration with health insurance providers (e.g., 174), and the system can analyze specific activity against reimbursement rules managements for a plurality of health insurance providers. In some examples, the system can determine if an expense is reimbursable, generate a request for reimbursement, and communicate the request to the health insurance provider. In further examples, some fitness activity can be at the request of a user's physician and any such request can be automatically captured and included in the automatic submission for reimbursement. In other embodiments, the system can identify reimbursement opportunities associated with a user's health insurance provider and/or from the user's employer. In one example, the system identifies reimbursement opportunities and tailors a recommended fitness program or fitness activity to the user, and ensures compliance with reimbursement requirements. In still other examples, the system can generate a payment request to the health insurance provider and communicate the request to the user's physician for submission and/or payment.

In another approach, users can provide their health insurers access to fitness activity tailored to the user's permission grant (e.g., limited view to summary information or validation information confirming fitness activity). For example, users can grant permission to access information stored in the multi-tier database. In further example, users can refine their access grant to specific types of information (e.g., summary information, date and time of fitness activity, sensor readings, specific sensor types, etc.). The system can be configured to enable user selection of permitted entities (e.g., health insurance), types of data available to the entity, etc. For example, the system can generate user interfaces for display data types, reports, specific data instances, etc., and users can select within the user interface to enable or disable access. Underlying APIs executing on the system can be configured to manage data access control between the various integrated systems (e.g., an API can communicate and manage functions with a health insurance provider 174, another API can communicate and manage functions with a nutrition planning system 172, another API can communicate and manage functions with fitness centers 170, another API can communicate and manage functions with a physician's systems 168).

Some embodiments disclosed herein include systems and methods for securely allowing a trainer to schedule and communicate instructions and training regimens to clients in different fitness centers through the multi-platform architecture. As disclosed herein, trainers include fitness coaches, physicians, therapists, or any other experts in medicine or exercise. Additionally, systems and methods for connecting a client with a best fit trainer are provided. Further, a multilayered database with the ability to store users, payments, reports, fitness programs, contacts, new feeds, connections, referrals, and profiles is provided.

According to some embodiments, a user interface is provided. The user interface may receive input to register clients. The clients may be registered with the system and stored into a database with information such as, for example, a name, an email, a gender, a date of birth, a referral date, a status, biographical information, a medical group, a clinician, an employer, an assigned trainer, an address, a phone number, payment information and other information.

The clients may be added to a training program (e.g., stored in a multi-tier database). According to some embodiments, the system can manage association of a client to a trainer based on program selection and further manage execution of the program. In some examples, a program may be a training package that members may purchase. The program may include information such as an associated sales staff, a purchase date, a start date, a price, a down payment, a number of included sessions, a number of available sessions, a payment deadline, a method of payment, and a payment amount that has been paid so far. The program may be associated with a trainer. In some embodiments, a client may request a program and a trainer (e.g., fitness coaches and physicians) may sign up to lead it. For example, the system may receive a request for a shoulder therapy program with a monetary price range and requirements. In response, the system may forward the request to trainers and the system may find a match with an expert trained to help with the requested program.

In some embodiments, a trainer may not necessarily be in the same fitness center as the client. If there is a difference in location, the user interface may include a video stream that allows the trainer to interact with the client for a scheduled session. Each client may have a username, email, and password to login to the system, at their device, and/or at a fitness device in a fitness center. Different clients may have different access levels and privileges in the system. In some examples, users are identified when accessing a fitness machine with a display. In one embodiment, the system identifies the client and the machine and automatically routes a video stream from the trainer directly to the identified client and machine.

Clients may also be associated with clinicians, or health professionals connected to the clients. The clinicians may be associated with medical groups, each medical group comprising a group of clinicians. Clients may also be associated with employers, and employers (including all of the employers' associated clients) may be associated with fitness centers. A clinician may include the same information as a client, with additional information relating to the clinician's medical group and position.

Trainers may also be added to via the user interface. Trainer information may include similar information to clients, with additional information such as availability, associated fitness centers, associated programs, hourly rates, associated clients, historical information (e.g., past clients, success rates, etc.), and other information.

Fitness centers may also be added via the user interface. In some example, a fitness center may include multiple locations and each location may be associated with trainers and clients. The user interface may receive input for fitness center information including a name, an email, a website, an address, a phone number, notes, and other information. The fitness center may also include a username, password, name, and email for a manager of the fitness center to login and control information related to the fitness center. The fitness center may also be associated with open hours, and a payment destination for clients who want to pay for a membership. Fitness centers may each have sales staff associated with them who are in charge of advertising and selling programs in the fitness center.

The system may manage payment between clients, trainers, and fitness centers. A report may be generated, for example, and maintained by the system. The report includes payment information relating to each member. Further, reports can be generated for specific fitness centers or trainers and customized based on desired information. Reports can also be generated for a client, trainer, or fitness center for any range of time.

The user interface may also receive program information to create and assign clients to programs. A program may include a description, a price, a service type (e.g., private or group), a duration of the program, a frequency of program sessions, a number of sessions, sales staff who sell the program, a duration of each session, dates the program is active, trainers who supervise or lead the program, and associated clients enrolled in the program.

Figure 1C:
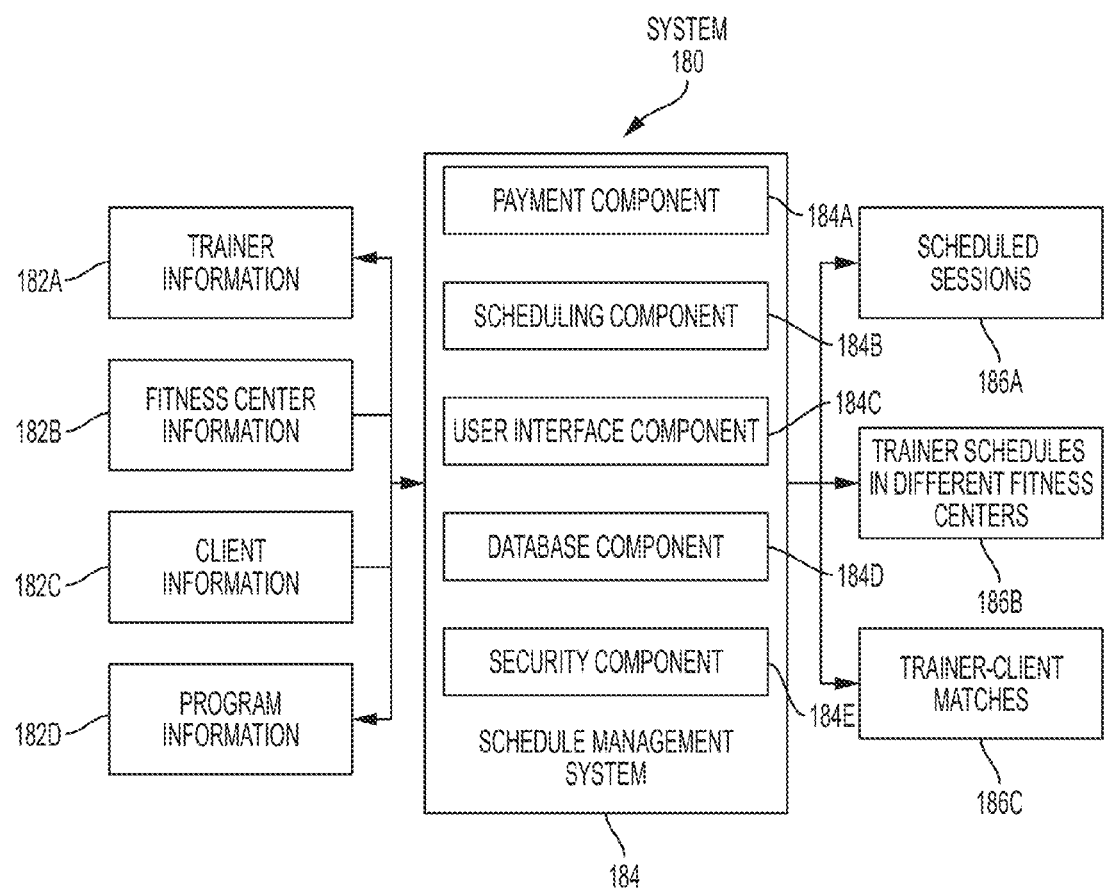
FIG. 1C illustrates an example schedule management system diagram, according to one embodiment.

FIG. 1C illustrates a system 180 for managing schedules for multiple trainers in multiple fitness centers. As illustrated, the schedule management system 184 receives trainer information 184A, fitness center information 184B, client information 184C, and program information 184D. The schedule management system 184 includes a payment component 184A, a scheduling component 184B, a user interface component 184C, a database component 184D, and a security component 184E. The schedule management system 184 outputs scheduled sessions 186A, trainer schedules in different fitness centers 186B, and trainer-client matches 186C.

As described above, the trainer information 182A, the fitness center information 182B, the client information 182C, and the program information 182D can be associated with each other. For example, the client information 182C may include an associated fitness center received from the fitness center information 182B, an associated trainer received from the trainer information 182A, and associated programs received from the program information 182D.

All of the information may be received via a user interface component 184C. The user interface component 184C can further display information from multiple trainers, clients, and programs within multiple different fitness centers. The user interface component 184C can receive information and transfer information related to credit cards and payment methods to the payment component 184A, information related to schedules and availability to the scheduling component 184B, information related to the associations between resources (e.g., clients, trainers, fitness centers, programs, etc.) to the database component 184D, and information related to user levels and accessibility to the security component 184E.

The database component 184D stores and retrieves any of the inputted information. The database component 184D can interface with the security component 184E to allow a user access to requested information based on the user's level. In some embodiments, user levels define access rights, and can be used by the system to control access to content. The level of a user may indicate what the user has access to. Additionally, the user level may be limited to a specific fitness center or group of fitness centers such that one user with a user level only has access to client information related to one fitness center and another user with the same user level only has access to client information related to another fitness center.

The security component 184E can control multiple user levels and manage and customize different resources in different locations. For example, owners of fitness centers may be given access to create and edit trainer information 182A, fitness center information 182B, client information 182C, and program information 182D associated with the fitness centers owned by the owners. Owners may only have access to their own fitness centers. Administrators may have access to edit any information relating to any user, program, or fitness center. Trainers may edit information relating to the trainer or programs the trainer is associated with.

The outputs of the schedule management system 184 include scheduled sessions 186A. The scheduling component 184B may work with the payment component 184A and the database component 184D to match client times with trainer times and generate trainer schedules based on the availability of clients and trainers. Alternatively, the scheduling component 184B may display trainer schedules to users to sign up for timeslots with trainers. The scheduling component 184B may schedule sessions and send reminders and notifications to trainers and clients to remind them of the session, including the location of the session. The scheduling component 184B may also schedule using rooms in fitness centers.

According to some embodiments, programs may also be created by a client. For example, if a client needs a specific therapy that is not available, the client may create a program and request for a trainer to join. The client may also enter specific information for the therapy (e.g., allergies, required max length of therapy, etc.) In some embodiments, the scheduling component 184B may access trainer information 182A in the database component 184D to find and notify trainers who have a match with the requested program. Once there is a match and a trainer signs up to lead a program, the scheduling component 184B can generate scheduled sessions 186A.

The scheduled sessions 186 include schedules for clients, trainers, and fitness centers. For example, the scheduling component 184B may display a schedule of a specific program, a specific trainer, specific rooms, etc.

Additionally, the schedule management system 184 outputs trainer schedules in different fitness centers 186B. The scheduling component 184B may generate a schedule for a trainer and in multiple different fitness centers. In some examples, the scheduling component 184B allows a trainer to remotely access a computer in a fitness center to instruct a client. The scheduling component 184B may interface with the user interface component 184C to allow a trainer to be in a live stream at a fitness center room for an allotted period of time to help a client.

According to some embodiments, the schedule management system 184 can also output trainer-client matches 186C. For example, if a user requests a shoulder therapy program, the scheduling component 184B may generate a list of relevant trainers who have prior experience with similar therapies from the database component 184D and display the list via the user interface component 184C. The scheduling component 184B may also display a success rate of each trainer and the duration of time the therapy took. The user interface component 184B may then select trainers who match their program's criteria and the scheduling component 184B may send trainers notifications of the request. If the user interface component 184B then receives a confirmation from a trainer, the scheduling component may schedule sessions for the program and display the trainer-client match 186C to both parties.

Figure 2A:
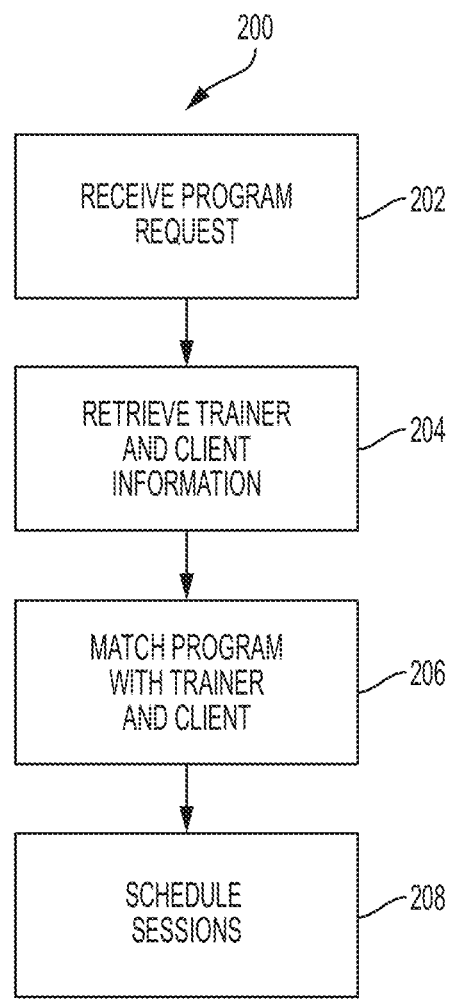
FIG. 2A illustrates an example process flow diagram, according to one embodiment.

FIG. 2A illustrates an example process 200 for scheduling sessions according to one embodiment. At act 202, the schedule management system receives a program request. The program request can be received from a trainer for a new program that the trainer wants to lead or from a client who wants to request a program. At act 204, the schedule management system retrieves client and trainer information. The schedule management system retrieves schedules for trainers and clients to determine a good time slot.

In some embodiments, if a client requests a program, the schedule management system may retrieve trainer histories to generate a list of recommended trainers. In other embodiments, the schedule management system may choose a best fit trainer. In other examples, if a trainer created the program, the schedule management system may retrieve client information and inform clients about the new program. The schedule management system may choose relevant clients and trainers based on their biographies and histories.

According to some embodiments, at act 206, the schedule management system matches the program with trainers and clients. The trainers and clients may receive a notification to confirm the match. Once a trainer and a threshold number of clients (e.g., 1 for an individual program or 3 for a group program) confirm the match, at act 208, the schedule management system schedules sessions for the program based on the availability of the trainers and clients.

Figure 2B:
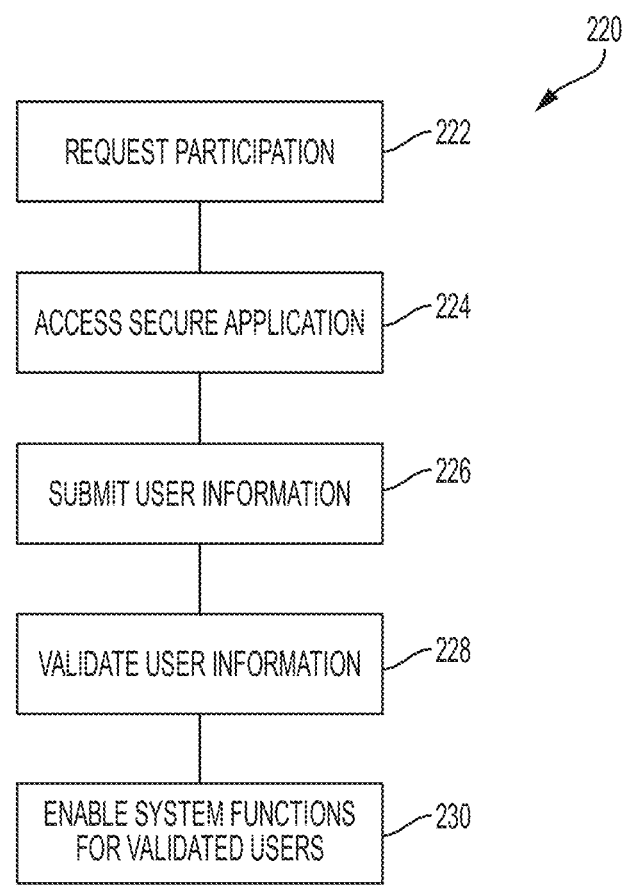
FIG. 2B is a process flow for registering a user device, according to one embodiment.

Various embodiments (e.g., systems 100, 160, 180, etc.) can implement a variety of processes to execute specific functions discussed herein. FIG. 2B shows an example process 220 for registering users to communicate with the central system via a secure messaging application. The process 220 beings at 222 with a request to participate on the central communication system and/or a request to install the secure application. In some examples, a user can be sent an invitation at 222 to participate with a link to download the secure application. In other examples, a request to participate can be processed via automatic administrative functions, and/or administrative personnel as a health monitoring device is issued to a user.

Upon validating the request (e.g., completing installation of the secure application, pairing the health monitoring device to a user device, obtaining a digital fingerprint of the user's device, obtaining user's information, etc.) the user can be requested to input any permissions to other users (e.g., primary care physician, trainer, etc.) to have access to their data. In further examples, registered users can invite their physicians or trainers to participate on the central system. In still further examples, once added the physicians are not permitted access user data until registered and explicitly granted access by a user specifying the specific data to be accessed.

At 224, the user can access a secure application to complete a registration, for example, using the information provided in an invitation or accessible in the downloaded secure application. In some embodiments, an invitation can specify user roles for the invited users (e.g., fitness participant, physician, trainer, etc.). For example, invitations can be extended to groups of physicians (e.g., a practice group). Thus, a user role can be a factor in the functions provided. For fitness users, process 220 can continue at 226, with submission of their information, contact number, biologic information (e.g., height, weight, sex, etc.), social, last four of their social, health provider information, health insurance information, etc. The provided registration information can be used to validate the user and/or any invited physician at 228. Only once the user is validated, system functions are enabled for the user, for example, at 230.

In further embodiments, once a user is registered, the user can trigger invitations to other entities that the user wished to have access, for example, the user's physician.

Figure 2C:
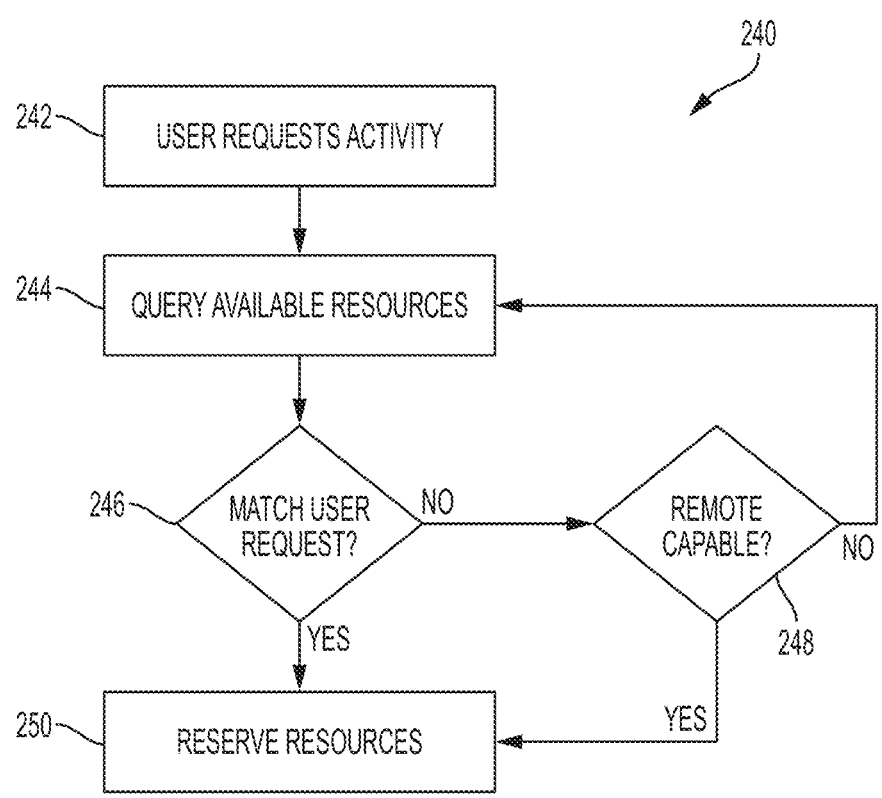
FIG. 2C is an example process flow for scheduling resources via the central system, according to one embodiment.

Shown in FIG. 2C is an example process for scheduling resources via the central system. Process 240 beings at 242 with a user requesting an activity on the system. In some embodiments, the system can be configured to supply information on resources (e.g., fitness equipment, trainer, fitness center, etc.) need for the requested activity. For example, the system can access a user profile to return a default fitness center and/or default equipment. In another embodiment, the user can specify detailed information on the requested activity in a user interface (e.g., selected fitness center, desired trainer, equipment, time, etc.). Responsive to the user's input and/or system identified parameters, a query is executed on available resources at 244. A variety of systems can be accessed, for via APIs to the respective systems, or current data can be collected and made available for query execution.

If resources are available that match the user's request 246 YES, then the resources can be reserved at 250. If not, 246 NO, any matching resources identified can be analyzed to determine if those resources are remote capable. If they are remote capable 248 YES the system can schedule a resource for the user at a user specified location or matching their profile, while scheduling remote resources (e.g., a trainer) available at another facility. If no one of the matching resources are remote capable, the system can expand selection criteria and repeat the query at 244, and repeat until a match occurs. If query criteria needs to be expanded to find a match, process 240 can include an optional step (not shown) of requesting approval from the user before reserving resources at 250.

Figure 2D:
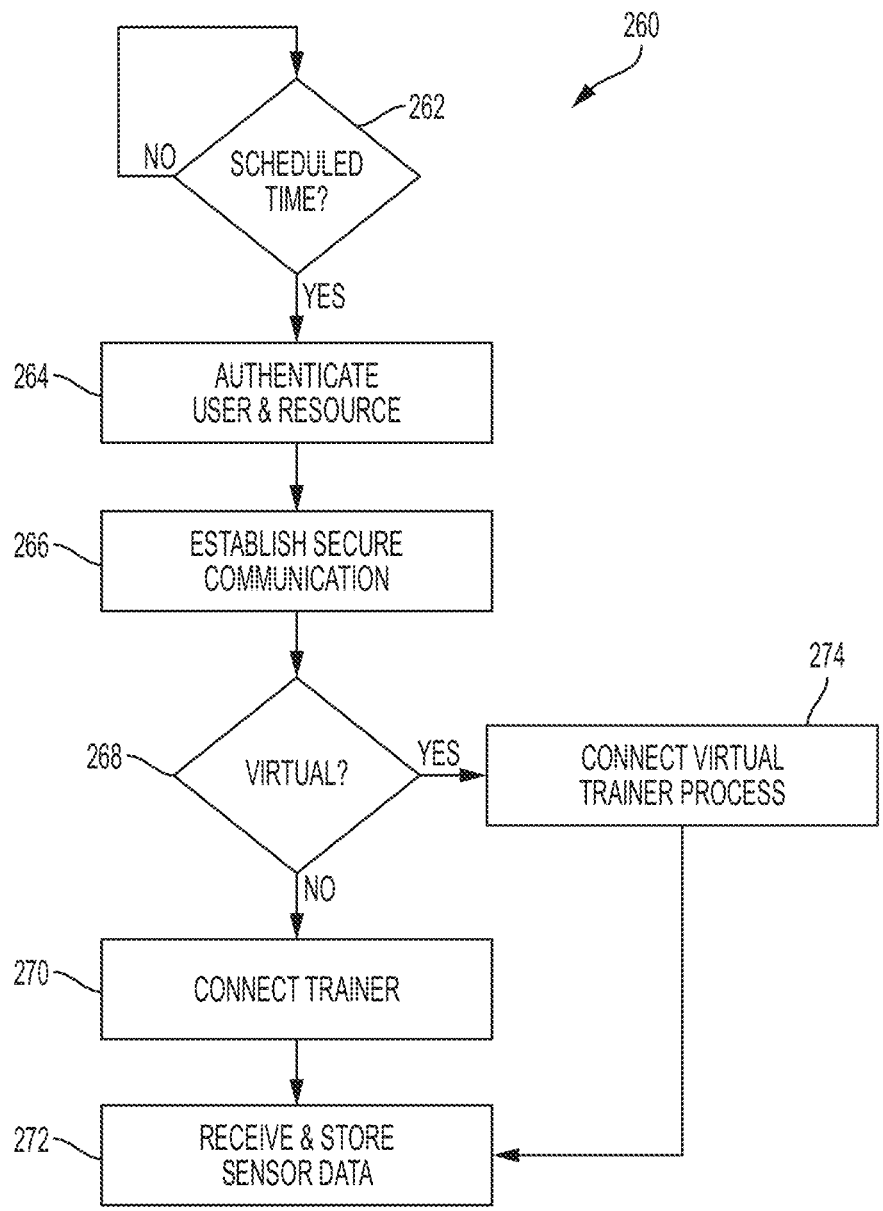
FIG. 2D is an example process flow for conducting a training session, according to one embodiment.

FIG. 2D is an example process for conducting a training session according to one embodiment. Process 260 beings at 262 with a check on the schedule time. If current time matches the schedule time 262 YES process continues with 264, and authentication information and resource information is checked at 264. Otherwise process 260 loops back to 262 via 262 NO. Once the user is authenticated and the assigned resource is confirm, a secure connection is established between the central system and the user's device. In some embodiments, a secure connection can be established between the resource (e.g., fitness equipment) being used, for example, where the resource includes biosensors or other sensor devices. If training session is virtual 268 YES, the central system connects the user to a virtual trainer process 274. The virtual trainer process can be configured to monitor sensor data and provider encouragement during a training session, analyze video signals received and recommend adjustments in posture, position, execution, etc.

If the session is not virtual 268 NO, a connection is established to the trainer running the fitness session at 270. Process 260 can continue with receipt and storage of sensor data from any sensor available to the system at 272. Including, for example, sensors on the user's device and any paired health monitoring devices. Although process 260 is illustrated with sensor capture occurring as step 272, sensor data can be captured any time the user's device is active and/or paired with health monitoring devices. In some examples, step 272 includes changing a data capture rate for the user's device and/or paired health monitoring device rather than a discrete step of receiving sensor data.

Figure 2E:
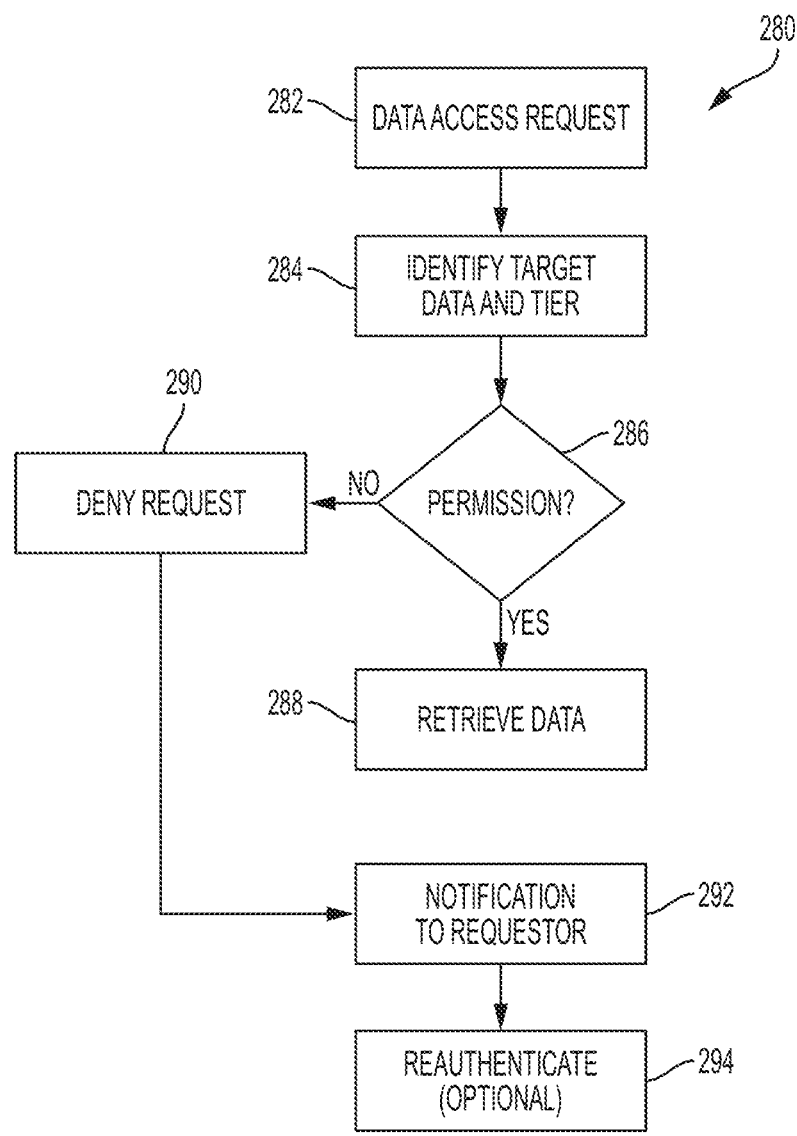
FIG. 2E is an example process flow for managing data requests, according to one embodiment.

FIG. 2E is an example process flow 280 for managing data requests. Process 280 beings at 282 with a request for access to data. The request can be initiated by a user, physician, trainer, fitness center system, or other integrated system. In some embodiments, an API can identify the requestor for the data based on an originating system, user name, etc. At 284, target data subject to the request is identified. At 286, the target data and associated access restrictions (e.g., data tier in the database) are evaluated against information on the requestor and/or process seeking access to the data. If the requestor have permission to access the data, for example, based on a permission tier the data is stored in, 286 YES, process continues at 288 with retrieval of the requested data. If the requestor does not have permission 286 NO, the request is denied at 290. The requestor and/or process is sent a notification regarding the failed request (e.g., "insufficient permission"). In some embodiment, a user associated with the target data can receive a notification identifying the requestor and of the attempt to access restricted data. In some examples, the user can determine whether to grant access to the requestor.

Other optional actions can be taken in response to a failed permission check. For example, at 294 the requestor may be required to re-authenticate in order to remain connected. Other optional actions include notifications to administrators and/or security personnel.

Example Implementation—Central Management Database System

According to one embodiment, users are issued JABRA PULSE health monitoring devices upon registering or subscribing to the system. The Pulse is a wearable electronic interface that can operate a remote control platform for the central system and functions. In other embodiment, difference health monitoring devices can be issued to users. Various embodiments, integrate the health monitoring device into a HIPAA compliant virtual patient center platform (e.g., the system). Other embodiments, can include machine learning algorithms to anticipate the needs and habits of the client (e.g., fitness routines, fitness requirements, needed/preferred fitness equipment, etc.).

In further embodiments, a secure application can be downloaded and installed on a user's mobile device or other computing platform, The secure application can be configured to relay data directly from the user's device to the central system, while preserving compliance with health regulation platform. In some implementations, users are given health monitoring devices via physician visits, trainer visits, or fitness center visits. The client can receive hands on instructions and direct assistance to simultaneously download the secure application while pairing/registering their user device and health monitoring device on the system.

In further embodiments, multiple devices can be paired with the user's device and/or secured application. In one example, the secure application can be configured to automatically pair to any additional health monitoring devices.

During registration the secure application can be configured to capture unique identity information associated with the users devices. The unique identifiers can be used to manage access requests and even to permit or deny access to entering in authentication information from the secure application or through the health monitoring device.

Analysis of user activity associated with the health monitoring device can be used to augment the health monitoring device functionality. In some embodiments, a JABRA PULSE device can be augmented to include embedded voice command processing enabling additional levels of communication security. Some examples of additional devices the secure application can pair with include Bluetooth devices that may be used concurrently or alternatively are speakers, gloves, infant ankle bracelets, other wearable devices and closed cellular network devices that are configured to capture information on a respective user.

Example Platform Integrations

According to one embodiment, the central system can be further integrates into a variety of services and/or applications providers to users. In one example, the central system is integrated with a nutrition planning system. The known VITABOT application is one example, of a nutrition planning technology that can be integrated and made available to users. The application is configured to generate balanced meal plans, nutrition and track dieting goals of the user. In further embodiments, physicians and/or trainers can access integrated programs on behalf of their patients (the users) and input dietary restrictions, nutrition targets, etc. with physician direction, the user obtains medically approved nutrition planning servers (e.g., which may lead to reimbursable expenses with health insurers).

According to other embodiments, the central system can include a training program generator (e.g., a workout generator) that executes machine learning algorithms to preemptively anticipate a next phase of user input or system generated workouts. In some examples, the central system provides the knowledge base of proprietary internal workouts developed over decades and with professional trainers, that are used as training data. By analyzing the training data, the system is able to build customized workouts tailored to specific individuals and/or classes of people. The training data can also include prior execution of the training programs indexed against the users who participated. In some examples, the machine learning algorithms are configured to learn properties associated with respective users and associate those properties to successful exercise routines (e.g., repeated attended, repeated executions, etc.) and/or elements of successfully routines. Information collected on the users can then be used by the machine learning algorithms to select fitness programs for similar users. In one example, biologic data collected on current users can be compared to biologic data collected on prior users and their training programs to identify similar users, and a respective training program to execute.

Further embodiments can enhance biologic data capture by integrating additional health monitoring devices. For example, the SKULPT device and application measures a user's fat percentage and muscle quality (MQ) of up to 12 individual muscle groups, on each side of your body (left/right). The 12 muscles are: biceps, triceps, shoulders, forearms, chest, abs, upper back, lower back, thighs, hamstrings, calves, and glutes. In some embodiments, biologic data captured using the SKULPT device can be integrated into training data for machine learning, matching similar users (e.g., users having similar fat percentage and/or muscle quality) and automatically identifying training programs, etc.

According to one embodiment, the PULSE health monitoring device is specially configured to enable voice commands that can be interpreted by the secure application and/or central system. In one example, verbal command can be interpreted by the system and/or secure application to enable nutrition and/or meal planning with third party service (e.g., the VITABOT application).

In other embodiments, verbal commands can be interpreted and cause the system and/or secure application to initiate a virtual training session and execute a system selected training program. In some examples, the central system and/or secure application can identify the fitness equipment the user is on, identify audio and/or video component associated with the equipment and stream virtual trainer audio to the equipment or stream virtual trainer video to the equipment during a session. In further examples, the central system and/or secure application can tailor selection menus for verbal commands where the tailored menus enable users to verbally schedule a medical, a fitness or a nutrition appointment, and have the result of any of the preceding associated with the user on the central system (e.g., for use by machine learning algorithms). A verbal command interpreter can also be configured to print a current or past health report, access training programs and enable modification of the accessed training program, design a personalized workout plan, and for example walk the user through a workout generator application to build a fitness plan. In other examples, the verbal command interpreter can be configured to enable the user to order a customized TrainerMD report and/or listen to live or prerecorded educational webinars.

According to another embodiment, a multiplatform central system is architected to provide extensibility and enable incorporations of a variety of systems (e.g., nutrition planning, health monitoring, physician, medical treatment, fitness training, etc.) and handle further integrations seamlessly. In some embodiments, the central system registers and communicates with mobile devices, capturing health information from the mobile device and any other sensor in communication with the mobile device. In further embodiments, integration of the mobile device and sensors include verbal command interpreters and user interfaces configured to solicit verbal commands.

According to one embodiment, medically rated sensors are paired with an end user's devices to provide the highest level of confidence in data collection and subsequent analysis (e.g., by physicians analyzing collected data, trainers reviewing exercise history, etc.). In some implementations, the central system is specially configured to manage such medical data in compliance with health information regulations (e.g., HIPAA, HITECH, etc.). For example, a multi-tier database manages data access by respective users, data access by respective processes, implementing a variety of data access tiers. In some examples, the end users can participate in assignment of specific users to respective tiers (e.g., granting their physician access to their health data). To ensure regulatory compliance various personnel who interact with the system may also require training. According to one embodiment, implementation of the multi-tier and multi-platform database ensure security protocol for the user's medical data, enhancing security over known approaches. In further examples, managing access to the data via APIs enforces compliance with defined access rights and privileges, while facilitating inter-system communication and operability. In another example, API configuration minimize the data required to be communicated between disparate system over conventional system, and improve communication efficiency (e.g., in terms of bandwidth).

According to one example, personnel operating and maintaining information systems are both information security and HIPAA certified, and may also have advanced training in physical security protection on HIPAA systems in addition to advanced security forensics to detect an unauthorized physical access to the area containing HIPAA protected information. The central system can also be configured to automatically audit data access and implement advanced security forensics to detect any unauthorized data and/or physical access to protected health information.

In some embodiments, the system's access control system incorporates user's biometric data to assist in authentication. In one example, an API's executing on the system can terminate a connection or authentication session if the user's health monitoring device stops transmitting information from the user for a set time period. Other embodiments implement software and/or hardware timeouts to prevent spoofing attempts. In yet others, web and mobile application implement advanced encryption algorithms while data is in transit (e.g., TLS 1.2 and Extended Validation SSL Certificates). Additional security features include hardware implemented advanced encryption algorithms to protect data at rest. In one example, Windows based system use Windows Bitlocker and a Trusted Platform Module (TPM), and LINUX based systems use a 2048 RSA Key with a TPM.

As discussed, access to protected health information (PHI) or (ePHI) includes multiple levels of access controls to allow different degrees of information access controlled by proprietary API's executing on the system. Physical areas that containing ePHI/PHI are automatically observed by the system, recorded continuously for access auditing and monitoring, and automated video analysis can be used to determine improper/proper access.

In some embodiments, health monitoring devices can be upgraded for increased security via epoxy on circuits boards, and/or other seals to prevent hardware hacking, tampering, or eavesdropping attacks. System monitored security locks are implemented on all outer and inner walls of all facilities containing protected health information in addition to the use of other complex physical security mechanisms on all containers and information systems containing protected health information. Which can include for example, advanced cable locks for mobile workstations with sensors, reinforced physically secure server enclosures with sensors, hardware locks on information systems with advanced security features to prevent tampering with or removing ePHI. In further embodiments, even executing source code can be encrypted, for example, at the physical layer to increase security.

According to another embodiment, the central system implements advanced system incident and event monitoring (SIEM) software suite configured to record all access events (e.g., data, processes, physical, etc.) to the system and protected health information as well as intrusion detections, prevention, backup and recovery, and more. The tacked events can be audited automatically to ensure security.

Various embodiments implement a variety of APIs, each configured to manage and communication with a respective system. Additionally APIs can also be executed to handle security accesses to data, monitor data access by integrated systems, etc. In some embodiments, the system implements a single API that can execute all of the operations discussed for respective APIs, and in others implement a number of APIs configured to handle multiple systems.

Further embodiments incorporate APIs at end user devices to facilitate communication with the central system, collection of data, interpretation of verbal commands, etc. In one example, APIs and/or the secure application at the end user's device is configured to monitor at least one of: sleep patterns and/or cycles, pulse and other biometric data, audio recording (e.g., voice stress level, respiration, etc.), GPS location, telemetry, nutrition intake (e.g., via nutrition applications), exercise activities, educational knowledge (e.g., via tracked applications), demographic data, etc. Each integration point may be managed by a specific API and/or by the secure application.

In some implementations, the secure application can implement a head up display (HUD) for the user on their mobile device. In one example, an embedded API can manage communication with existing HUD services, control incident detection (e.g., rapid deceleration, impact, accident, etc.) and facilitate responses (e.g., emergency response, e911, etc.). The central system can trigger any number of prompts to mobile device, including for example, out-of-band authentication, voice responses and activation, registration operations include pairing devices, sensors, and/or functions with a unique signature and/or security pin.

According to some embodiments, implementing intermediary API's facilitates cross-platform implementations, extensibility, and communication. Further, tailored APIS enable consistent input/output operations at each system, allowing various application and service to handle their own native communication format for workflow of data, while preserving integration with the central system. Other features of some embodiments, include predictive analytic operations configured to automate professional tasks for trainers/physicians (e.g., automatically build fitness programs, identify nutritional issues, health issues, etc.). Dynamic reporting can be customized by the user, for example, detailing what data specific other users/systems can access. In further embodiments, custom scheduling operations with multi-level administration capabilities (e.g., system based administrator, "super" administrator, etc.) support lattice models of operations.

In one example, "super" administrators have access rights that include the ability to view or access high-level APIs and system functions provided by the system (e.g., define integrated systems, integrated system capabilities, access rights of integrated systems, etc.). In another example, super-users can control and manage multiple resources and objects with a different relationship scheme than normal users or administrators. This is in contrast to existing systems that typically define standard primary class roles for super-users which does not allow for a super-user to function at multiple levels while still inheriting the traits of a standard user/administrator.

U.S. Provisional Application Ser. Nos. 62/158,653 and 62/308,314 incorporated by reference in their entirety describe example user guides illustrating and describing features of some embodiments, example technical documentation illustrating and describing features of some embodiments, various embodiments, elements, and respective configuration of various examples of an integrated health platform. The integrated health platform can be configured to leverage different health platforms, health applications, remote medical devices (e.g., Jabra health monitoring devices (e.g., Jabra Sports Pulse device)), mobile devices, mobile device sensors, etc. The integrated platform provides a vehicle to access such information in a HIPAA compliant setting, as well as other environments that enforce HITECH compliance and yet others that implement further restrictions to provide for any other medical information compliance regime.

Figure 4:
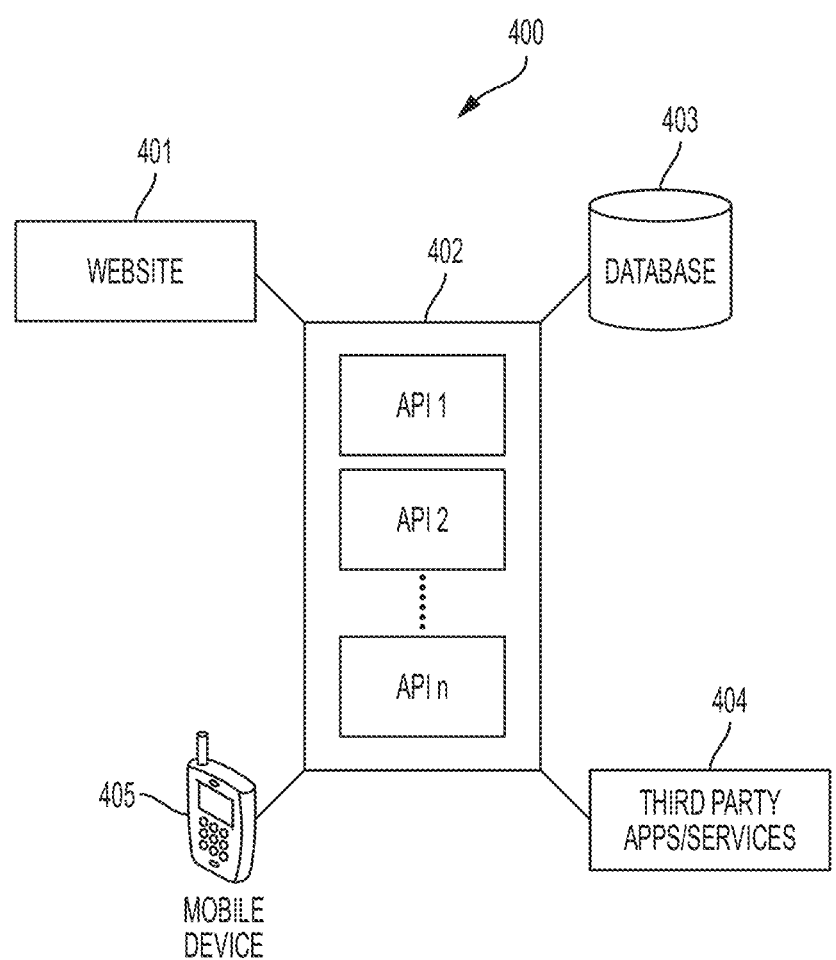
FIG. 4 is a schematic organizational diagram showing relations between components according to aspects of the present application.

FIG. 4 is a schematic organizational diagram of an example implementation of executing multi-tier data and multi-platform data access requests. The implementation comprised components hosted and executed on a Trainer MD environment 400 according to aspects of the present application. In FIG. 4, a website 401 is connected to a database 403 via one or more application programming interfaces (APIs) 402. In some embodiments, website 401 may comprise a front-end and a back-end component and the website 401 is responsible for allowing different type of users (members, trainers, fitness centers) to manage their schedules, see their reports and manage goals and vitals. In one example, website 401 allows super admin users to manage data in database 403.

In some embodiments, database 403 may contain diagrams and tables that hold the information, along with procedures that allow communication with website 401 and the one or more APIs 402. In one example, the database is implemented inside an SQL Server 2008 R2 instance. In some embodiments, the one or more APIs 402 may include a web service API that coordinates communication between the website 401 and the database 403. In one example, the web service API also coordinates an authentication process for accessing data in database 403.

In some embodiments, the one or more APIs 402 may include a Bizbot Windows application for managing the database structure in database 403, allowing the ability to create new users, manage programs and memberships, payments, contacts, newsfeeds and referrals.

In some embodiments, the one or more APIs 402 may optionally and additionally include a data utility layer to communicate between the website 401 and database 403. The data utility layer may be more secure and have higher levels of performance compared to methods that live inside the web service API. In some embodiments, the data utility layer may be adjusted over a period of time and be open for improvements. In some embodiments, the data utility layer may allow the product to have an independent way to provide a public API to third party solutions such as third party apps and/or services 404 as shown in the diagram in FIG. 4.

In some embodiments, one or more APIs may be provided to interface with mobile device 405 to communicate data from database to an operator of the mobile device 405 and/or to communicate commands/queries from the mobile device 405 to interact with elements in database 403 as well as one or more third party apps/services 404. The operator of mobile device 405 may be trainers, clients, and/or personnel at fitness centers and the mobile device 405 may be used to enable managing of schedules and other functionalities across different locations. Mobile device 405 may be smart phones, PDAs, wearable watches, smart glasses, or any other suitable electronic device for communicating remotely with the API.

In some embodiments, some components in the Trainer MD environment may be implemented in a cloud computing service that provides resizable compute capacity in the cloud. As a non-limiting example, some components may be based on the Amazon Elastic Compute Cloud (Amazon EC2) service. Such an implementation using Amazon EC2 may make webscale cloud computing easier for developers.

Figure 5:
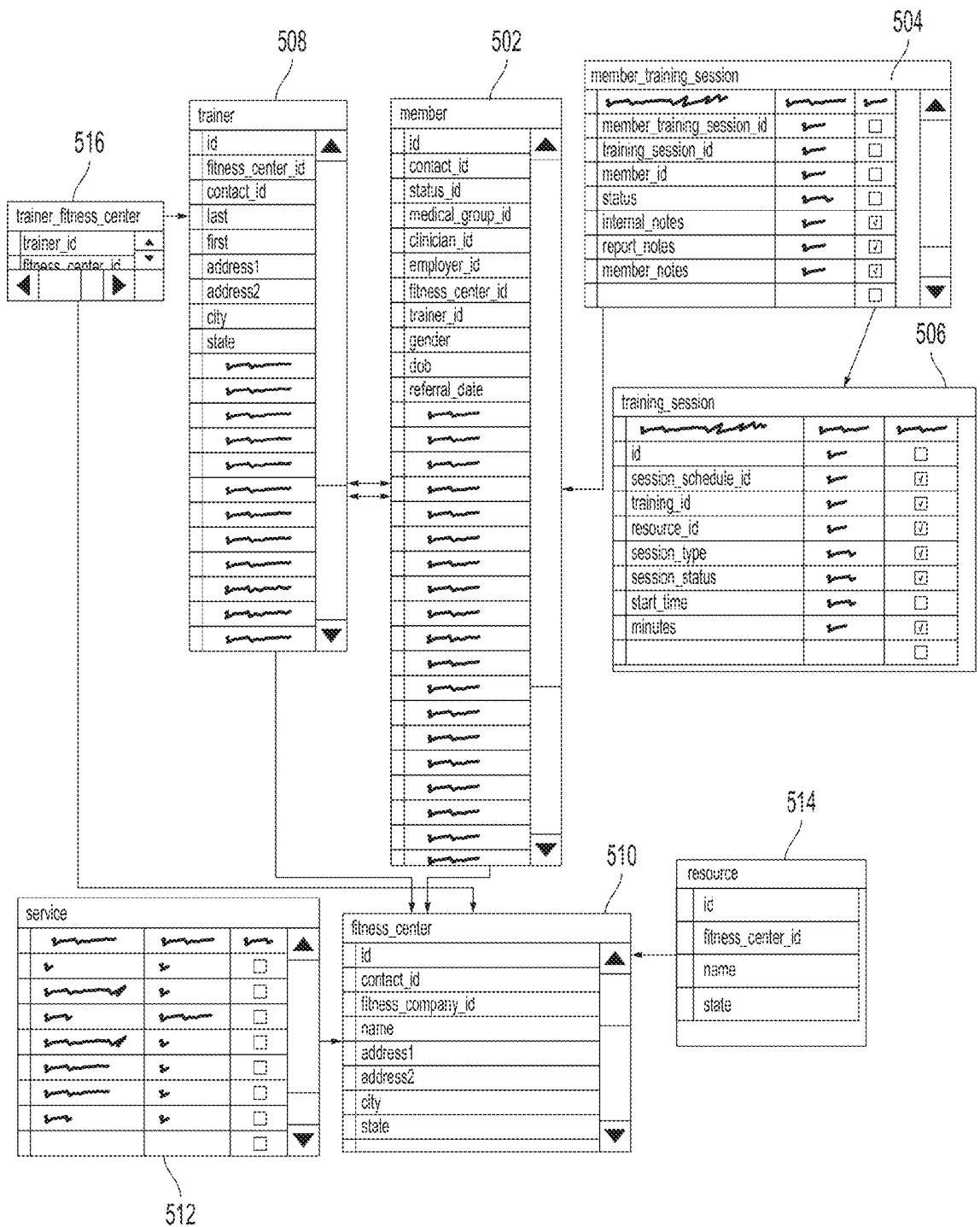
FIG. 5 is a schedule diagram showing tables representing data structures in an example data model.

FIG. 5 is a schedule diagram showing tables representing data structures in an example data model used in a database (e.g., a multi-tier multi-layer database as discussed herein). In the example in FIG. 5, each member in the table "member" 502 may be associated with a training session in the table "member_training_session" 504, where the training session associated with the member may be selected from the list in the table "training_session" 506. Each member may also be associated with one or more trainers in the table "trainer" 508. The trainers and members are each associated with a fitness center in the table "fitness_center" 510 that provides one or more services from the table "service" 512 as well as resources from the table "resource" 514. Additionally, each trainer may be associated with a specific fitness center location, as represented in the table "trainer_fitness_center" 516. In some embodiments, multiple trainers may be associated with a specific fitness center. A trainer may also be associated with multiple fitness center locations. Similarly, multiple users may be associated with a specific trainer and/or fitness center. Therefore, in some embodiments, each one of the tables "trainer" 508, "member" 502 and "fitness_center" 510 may be referenced more than once during each query to the database.

Figure 6:
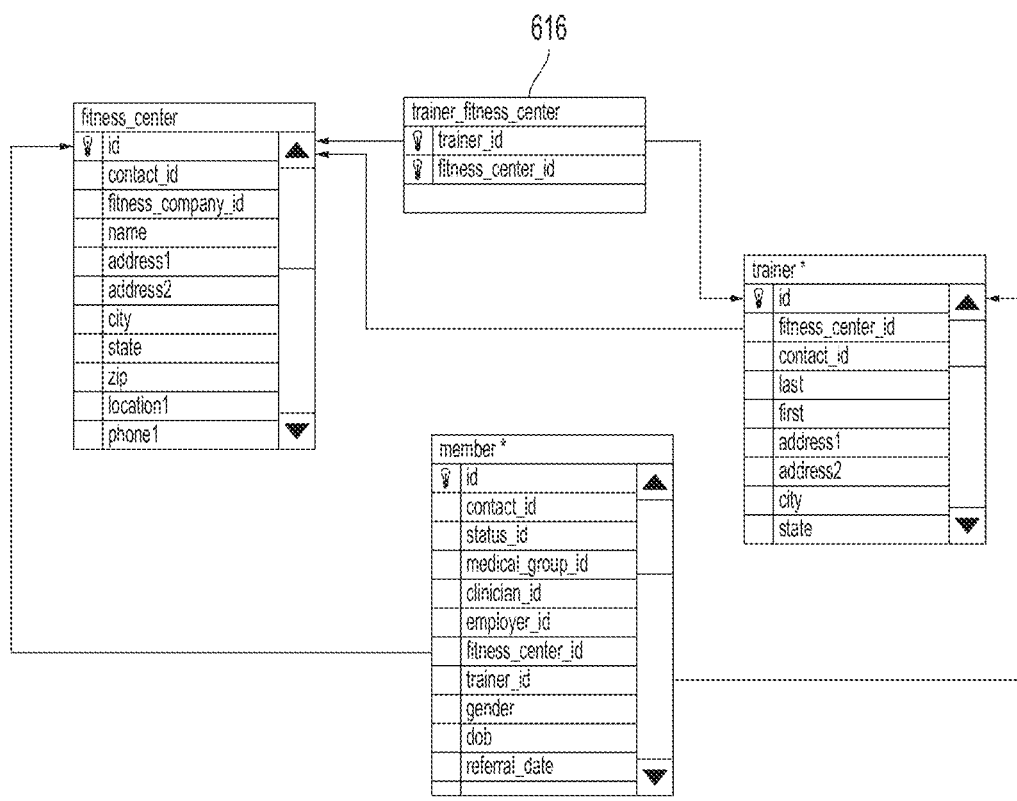
FIG. 6 is a diagram showing an example data model, according to one embodiment.

Aspects of the present application are related to accommodating trainers with multiple fitness centers. In some embodiments, the data model allows a trainer to work in more than one fitness center and manage all his schedules at the separate centers within one platform. Schedules may be viewed independently or in conjunction with other operators within the calendar view. Schedules of all centers are managed by simply selecting the desired fitness center from the drop down in the top right corner that displays all his associated fitness centers as will be discussed in relation with the UI interface below. FIG. 6 is a diagram showing an example data model representing the situation when a trainer may be associated with multiple fitness centers. In the example in FIG. 6, the diagram shows in detail how tables are organized in order to allow trainers to have multiple fitness centers. In some embodiments, the link table called "trainer_fitness_center" 616 allows the association between one trainer and one fitness center. In some embodiments, a trainer could be associated with any number of fitness centers stored in the database. In some embodiments, one "default" fitness center per trainer and one trainer per member may be provided.

Figure 7:
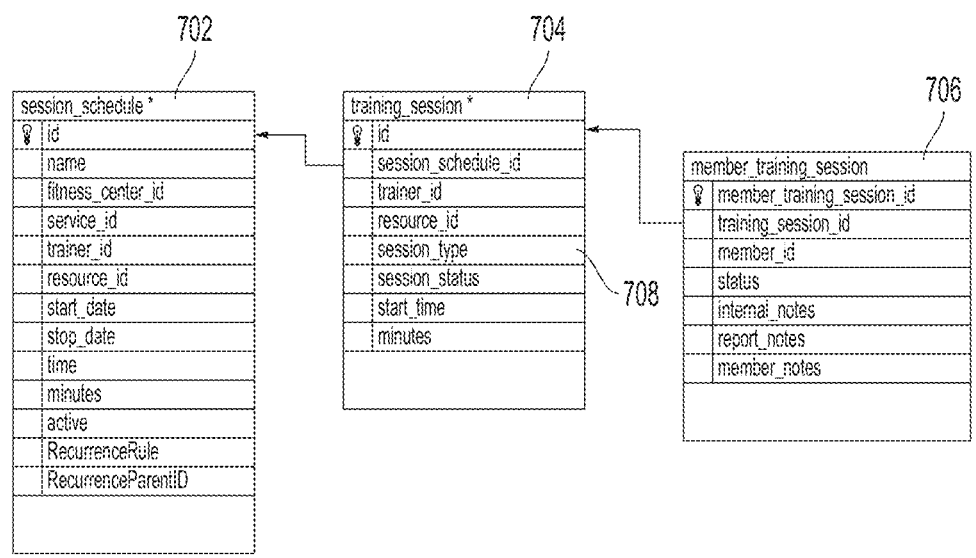
FIG. 7 is a diagram showing tables representing data structures as an illustrative example of a scheduling process, according to one embodiment.

FIG. 7 is a diagram showing tables representing data structures as an illustrative example of a scheduling process. In some embodiments, appointments may be managed by the three tables as shown in FIG. 7. In other examples, fewer or more tables may be implemented, as well as non-relational data structures or dynamic schema data structures. The "session_schedule" table 702 may be responsible for storing all the basic information about the appointment such as name, fitness center, service, trainer, and physical resource where the appointment may take place. It should be appreciated that a variety of basic information related to a training session may be stored, for example, as a line item in the "session_schedule" table 702. In some embodiments, information for recurring appointments may be defined inside the "session_schedule" table 702. A second table, "training_session" 704, may hold information about the type of appointment and status. In some embodiments, "training_session" table 704 may contain cloned information from a master appointment in the case of a recurring appointment, allowing an easier and faster way to manage all appointment types including normal and recurring appointments. The last table, "member_training_session" 706, may hold information about the members that belong to each appointment. In some embodiments, the "member_training_session" table 706 may also hold notes on each member in a specific training session.

In some embodiments, the "session_type" line item 708 in the "training_session" table 704 in FIG. 7 may be used to specify whether a training session is a local training session, where a user and a user's trainer are physically located in a particular local fitness center, or a virtual training session where a user may be physically located in a separate remote location from a trainer. For example, the user may have a virtual training session when he is not able to be present at the local fitness center with the trainer, due to travel or impaired mobility. In one example, the user may conduct a virtual training session by streaming in video and/or audio his activities remotely to a trainer. Having a remote virtual training session provides flexibility for the user to continue training sessions with local trainers without being bound by the need to be present at a local fitness center. In some embodiments, a local trainer may offer virtual training sessions for multiple users located both locally and remotely at substantially the same time, in order to consolidate training schedules and save training resources.

Figure 8A:
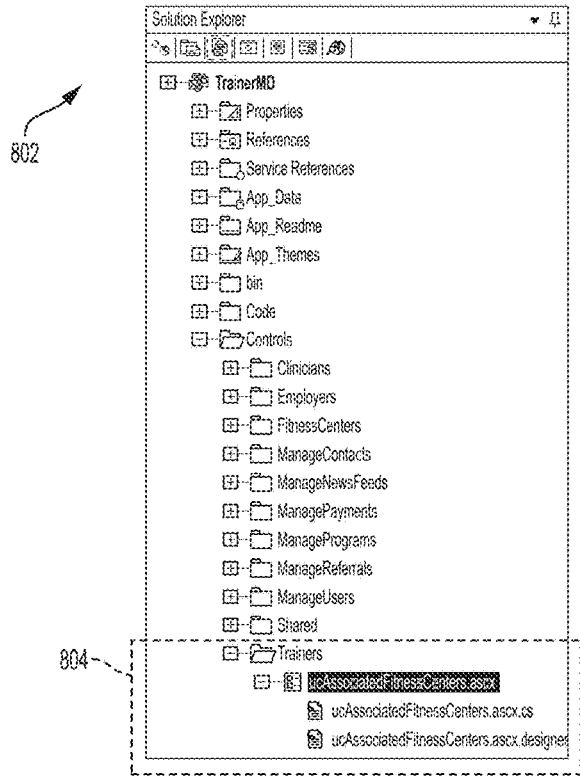
FIG. 8A is a screenshot image showing an illustrative example of a web user control, according to one embodiment.
Figure 8B:
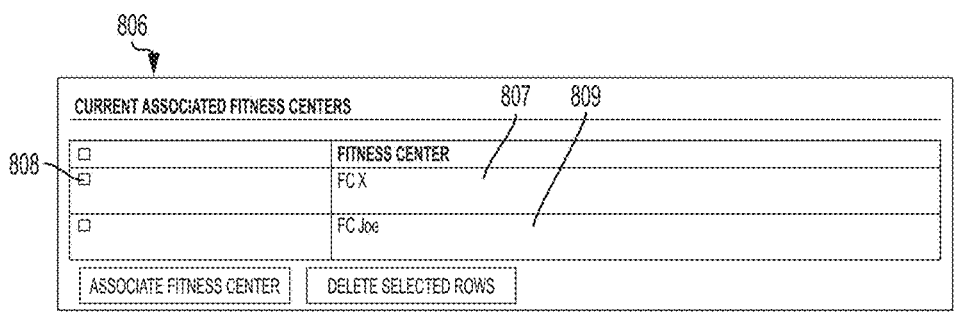
FIG. 8B is a screenshot image showing an example user interface for the web control, according to one embodiment.
Figure 8C:
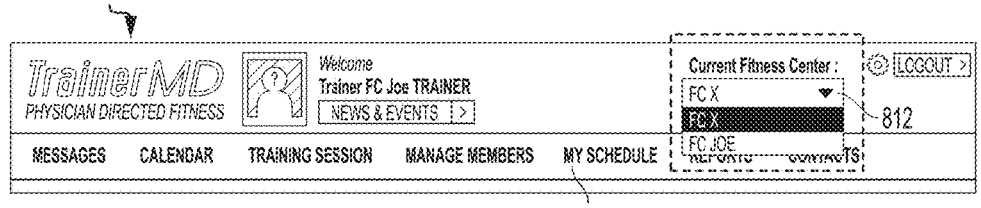
FIG. 8C shows a screenshot of an example user interface, according to one embodiment.

According to some embodiments, a web user control and related interface may be provided to allow administrators to easily manage and associate multiple fitness centers to one trainer. The ability to easily manage and modify associations between trainer and fitness centers allows flexibility in the platform's usage. FIG. 8A is a screenshot image showing an illustrative example of a web user control 802. Specifically, the "ucAssociatedFitnessCenters.ascx" control 804 in FIG. 8A illustrates how a web user control may be implemented according to one example. FIG. 8B is a screenshot image showing an example user interface 806 for the web control. In FIG. 8B, the image shows an example web control interface 806 according to an administrator's view, where the administrator may designate using the check boxes 808 an associated fitness center (FC) between "FC X" 807 and "FC Joe" 809 for a trainer. In some embodiments, the web user control manages the link table between fitness centers and trainers and may check to avoid a user deleting the default association between the trainer and his default fitness center. In some embodiments, trainers may have the option to select the current fitness center they want to work with inside the platform. FIG. 8C shows a screenshot of an example user interface 810, where a drop down menu 812 in the header section 814 of the user interface may be provided that allows trainers to make the choice between "FC X" and "FC Joe". Different architectures and data structures can be implemented in other embodiments.

In some embodiments, user selection of fitness centers may be managed by a login web user control. In one example, the login web user control updates one class that is always present in the background for the entire platform. In some embodiments, requests to the database may send the current fitness center as the parameter and a "MyFitnessCenter" value may be updated accordingly. Users are able to view information from one fitness center to another, in response to changing the selected current fitness center.

Figure 9:
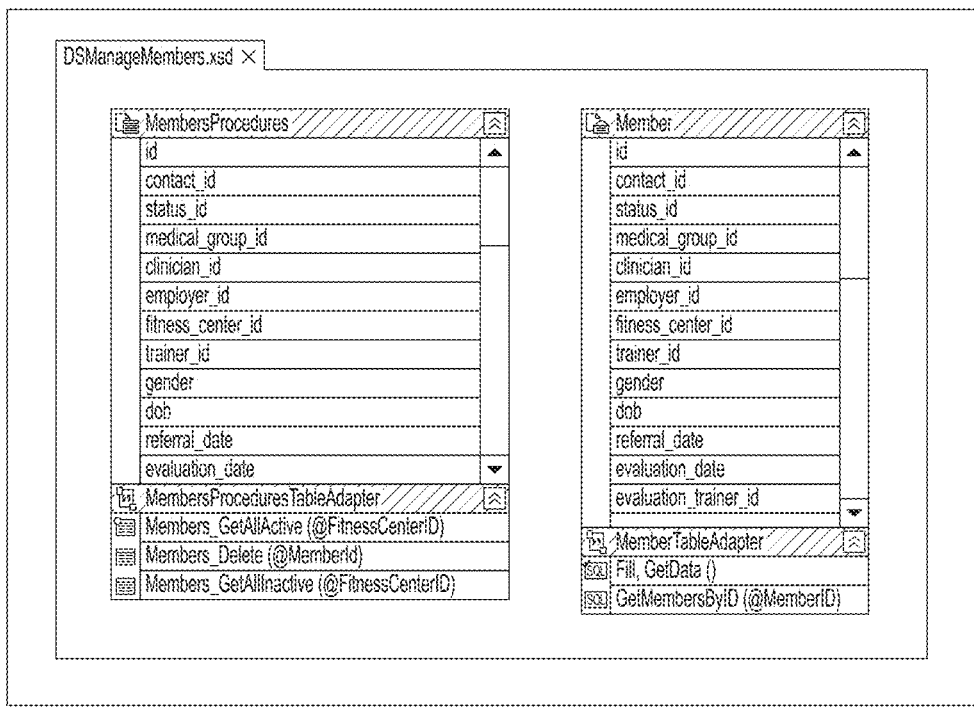
FIG. 9 is a screenshot showing an example data structure, according to one embodiment.

According to aspects of some embodiments, one of the APIs 402 may be a data utility API that connects directly to the database 403 in FIG. 4 in order to serve as a bridge between the website 401 and database 403. FIG. 9 is a screenshot showing an example data structure according to an implementation of the data utility API. In one example, the data utility API may comprise the following components: data sources, entities, providers, services, synchronizer, utilities.

The following description provides several examples of how management functions are implemented and/or visualized for a system administrator.

1. Implementation Overview

Figure 10:
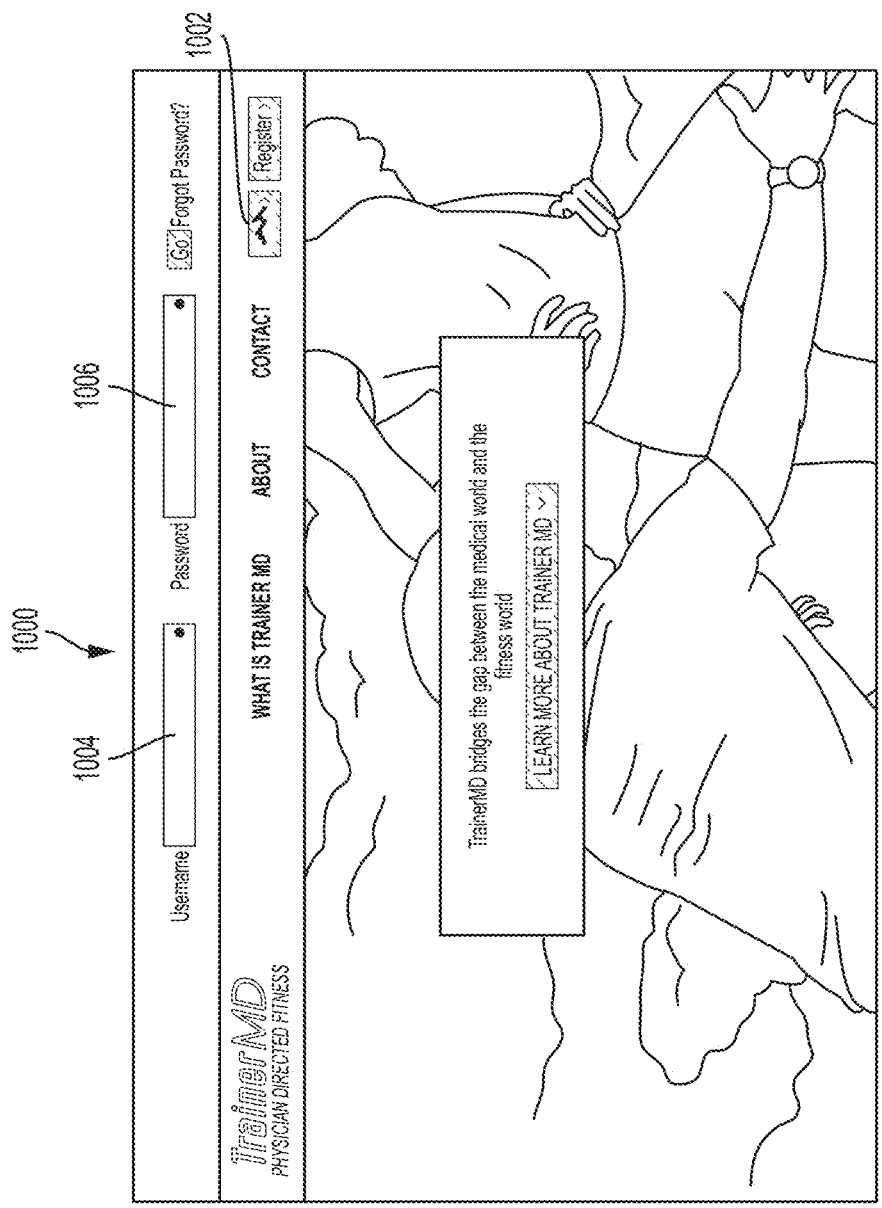
FIG. 10 is a screenshot image showing an illustrative example of a website interface, according to one embodiment.

FIG. 10 is a screenshot image showing an illustrative example of a website interface 1000. According to some embodiments, a user may navigate to the main website and log in with administrator credentials. In FIG. 10, clicking the login button 1002 can display the username and password fields 1004, 1006. In some embodiments, the website may be a mobile website with features optimized for displaying in a mobile device or in an app operating on a mobile device. Further authentication can be executed as described herein (e.g., continued sensor readings from a mobile device or paired health monitoring device, etc.).

2. Dashboard Example

Figure 11:
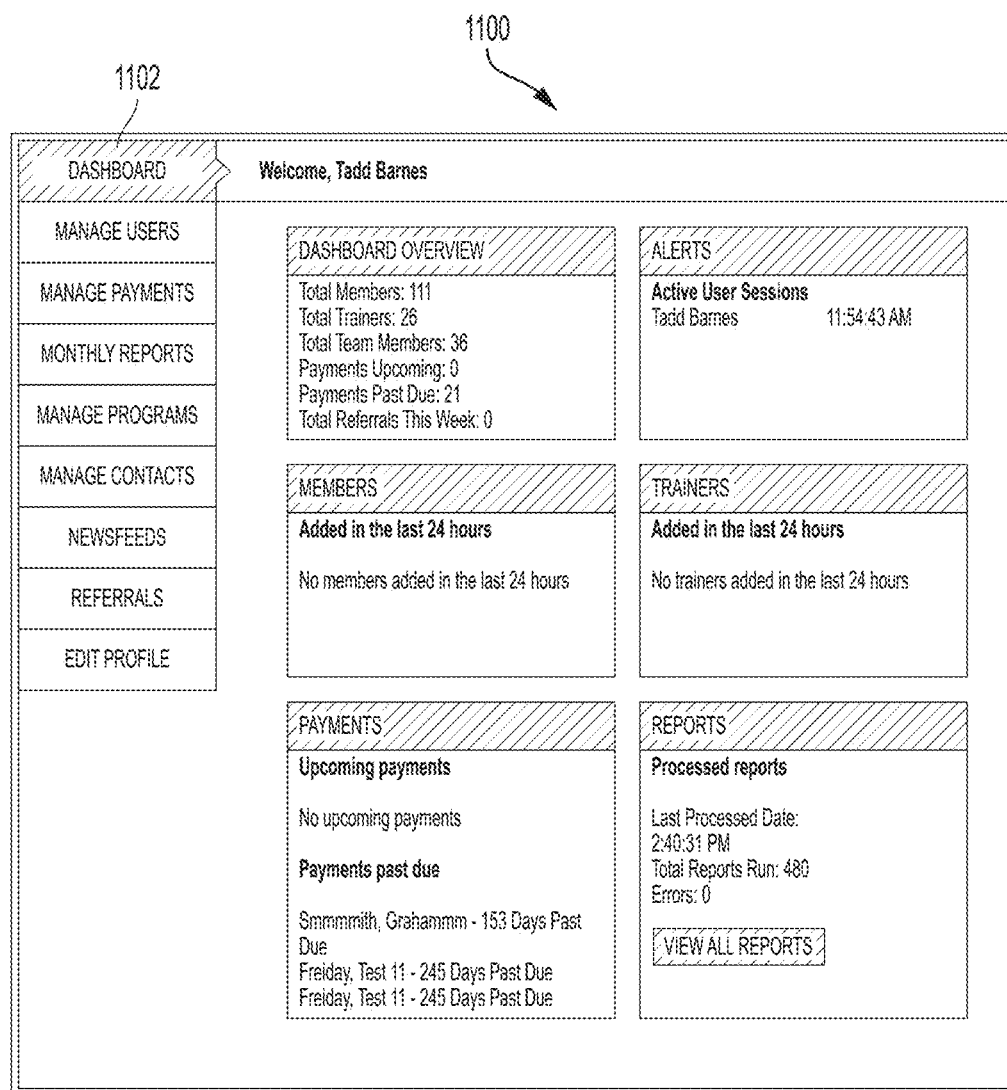
FIG. 11 is a screenshot image showing an illustrative example of a main dashboard interface, according to one embodiment.

FIG. 11 is a screenshot image showing an illustrative example of a main dashboard interface 1100. In some embodiments, the dashboard such as the interface illustrated in FIG. 11 may provide a snapshot to a user of what is going on in the system. The dashboard interface may show an overview of all members and trainers in the system. It may also display alerts such as payments, reports, and referrals.

In some embodiments, a navigation bar 1102 may be included in the dashboard interface 1100. In one example, the navigation bar 1102 may be positioned to the left of the dashboard interface 1100 to provide navigation of the administration functions of the system itself. According to some embodiments, the administration functions of the system may comprise:

Manage Users: This includes managing users such as fitness center members, trainers, and additional fitness centers if available;

Manage Payments: This is a payment-tracking feature presenting for example all the payments made, payments pending, and/or payments that are past due;

Monthly Reports: This feature allows an administrator to generate system reports, as well as create custom reports. Reports may be based on vitals and information added into the system trainers;

Manage Programs: Programs are training programs that may be linked to payments by the user. In one example, the programs are training packages that a fitness center sells to its clients which may be added or managed in this function;

Manage Contacts: Contacts are resources that are connected to members of the fitness center. Contacts may include information such as clinicians, medical groups and employers of fitness center members. This area may also hold information about the fitness center staff;

Newsfeeds: This area is for creating global messages to send to users within the system;

Referrals: This area holds all of the information for users who have signed up on the website for an account;

Edit Profile: This is the area to modify the fitness center profile itself.

3. Manage Users Example

According to aspects of some embodiments, there may be provided a plurality of user types in the TrainerMD system. In one example, 3 types of users are provided: fitness center members, fitness center trainers, and the fitness center itself. Each member type may be managed from the tabs at the top of the screen of a user interface such as a website on a computer browser or on a mobile device.

Figure 12:
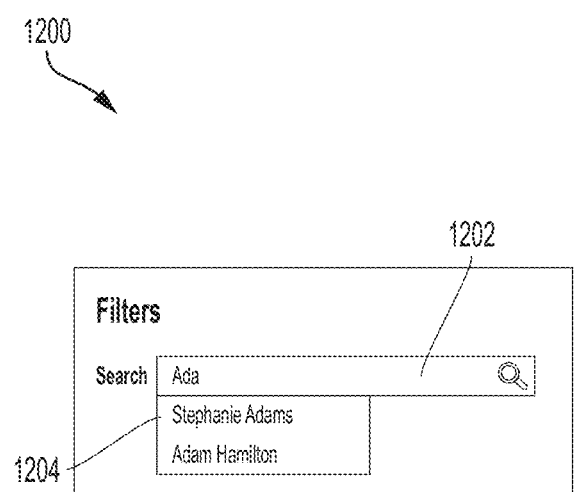
FIG. 12 is a screenshot of an example user interface, according to one embodiment.

In some embodiments, fitness center members are primary users in the TrainerMD platform. These are the paying customers of a fitness center. On a main tab of the members screen of a user interface there may be provided an action panel of buttons, a search filter, and a table displaying all members. FIG. 12 is a screenshot of an example user interface 1200. In the user interface in FIG. 12, a search filter is provided and accessible via a search box 1202 to facilitate locating a specific member quickly on the user interface. As an administrator types the name of a member in the search box 1202, a list 1204 may show suggestions below the search field. Once a specific member is selected from the suggestion list, by clicking on it, the field in the forms or website fields below the search filter may update to show the member.

3.1 Manage Users: Members

Figure 13:
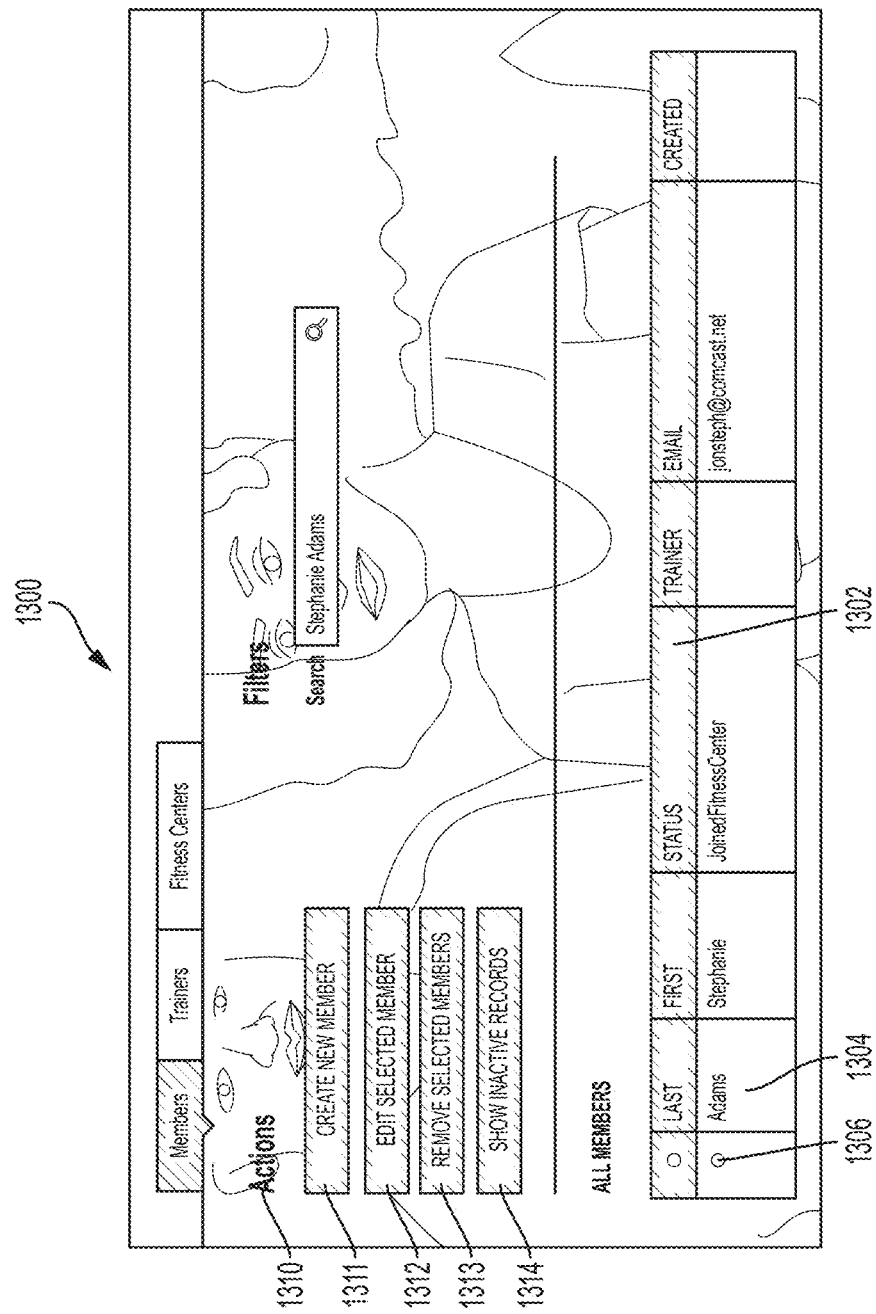
FIG. 13 is a screenshot image showing an example user interface for editing member information, according to one embodiment.

FIG. 13 is a screenshot image showing an example user interface 1300 for editing member information. In one example, to edit member information, a user may double click on the member name 1304 in the table 1302 which can trigger the system to transition the user to the member detail screen. A user may also click the checkbox 1306 next to the member and click the edit selected member button 1312 in the action panel 1310 to effect the same transition.

The actions panel buttons in action panel 1310 in the example in FIG. 13 may interact with the table 1302 below it. Each button represents a function that an administrator can take with members, such as:

Create New Member 1311: Create a new member in the system;

Edit Selected Member 1312: If a member in the table below is checked off in the checkbox, this may take the administrator to the edit member screen. This can also be accomplished by double clicking on the member in the table 1302;

Remove Selected Members 1313: This button allows an administrator to remove a single user or a group of users from the system;

Show Inactive Records 1314: When a member is removed, they are not deleted, they may be flagged as inactive. Inactive members are not be able to access the system, but they can be displayed here for archival purposes. An inactive member may come back to the fitness center and be re-enabled.

In some embodiments, a create new member screen may be provided to show a number of fields that need to be filled out to create a new member in the system. The following is a group of fields that may be shown according to one example:

Personal Information, which may include the following sub-fields of information:
 First: First name;
 Last: Last name;
 Email: Active email address of the user;
 Gender: This is represented in the pull-down with unspecified, male, and female;
 DOB: Date of Birth. This can be entered manually or using the calendar widget to the right of the field;
 Referral Date: The date the member was added to the fitness center. This can be entered manually or using the calendar widget to the right of the field;
 Status: There are multiple statuses in the system, but for this we may list our member as active;
 Active Checkbox: That the member is active in the system.

Assignments: Assignments are certain groups that members can be attached to. In some embodiments, a sub-field may be implemented with a validation logic such that when one or more values input in the sub-fields is determined to fail the validation logic, the system may proactively make selection choices or limit selection choices presented for one or more sub-fields. For example, the validation logic may look up medical plan information in a pre-set table stored in the database based on a given employer name, and proactively select the medical group corresponding to the employer's medical plan, if the selected medical group is among the reimbursable medical groups under medical plans for the given employer. In another example, the validation logic may determine certain medical groups, trainers and/or fitness centers that do not have reimbursement agreement under the given employer's medical plans and gray out or otherwise block out the choices for the ineligible choices for selection by the user, in order to speed up the user input process and reduce mistakes at the user interface. In some embodiments, an alert such a popup message or audible message may be played when a conflict between one or more input values is determined by the validation logic. The following are sub-fields that may be included under assignments:

Medical Group: This is a medical group that is listed in the system. The pull-down may show all medical groups that are associated with a fitness center.

Clinician: This is the clinician that is listed in the system. The pull-down may show all clinicians that are associated with a fitness center.

Employer: This is an employer that is listed in the system. A business may have a group of people attending a fitness center, and each member can be assigned with this employer. The pull-down may show all employers that are associated with a fitness center.

Trainer: This is the trainer that is assigned to this member. The pull-down may show all trainers that are associated with a fitness center.

Address: Physical address of a member.

Phone: phone contact information of a member.

Notes: additional information about a member.

In some embodiments, an add programs screen may be provided after a new member was added, in order to associate the member to one or more programs. In some embodiments, a program in this platform may a package of training that a member can purchase. The following is a group of sub-fields that may be displayed on the add programs screen according to one example:

Program: This pull-down menu shows some of the programs that are currently in the system for the fitness center.

Sales Staff: This is the member of the sales staff that sold the program;

Purchase Date: The date the program was purchased;

Start Date: The date that the program starts for the user;

Price: How much the program costs;

Down Payment: How much the member paid initially for the program;

Initial Sessions: These are the number of total sessions a member can purchase with this program;

Available Sessions: These are the number of sessions available to the member. If this is a new member to the fitness center this should be the same as initial sessions, however if members of the fitness center that have purchased previous sessions before being added to the TrainerMD platform this number can be different;

Payment Day: This is the day payment is due;

Method: The method of payment;

Payment Amount: The amount that a member has paid. Additional payments from a member may be recorded here.

In some embodiments, an edit selected member screen may be provided that allows an administrator to modify details of an existing member in the system. Some of the sub-fields in this screen are the same as those in the create user screen. The following is a group of sub-fields that may be displayed on the edit selected member screen according to one example:

Username and Password: It is here that the member's access to the system is generated. If a member has an account, it can be modified here, such as resetting their password;

Remove Selected Members: If a user needs to be removed from the fitness center, this feature is needed. To do this, simply search for the member one would like to remove, select the checkbox next to that member and click the remove selected member button. In some embodiments, an alert such as a popup message may display for the user to confirm removal of the information from the system.

Show Inactive Records: Inactive records are members who have been removed from the system. Pressing a show inactive records button may update the table below it and show the members who have been flagged as inactive. The button may also update to Show Active Records to go back and show the active records;

3.2 Manage Users: Trainers

Figure 14:
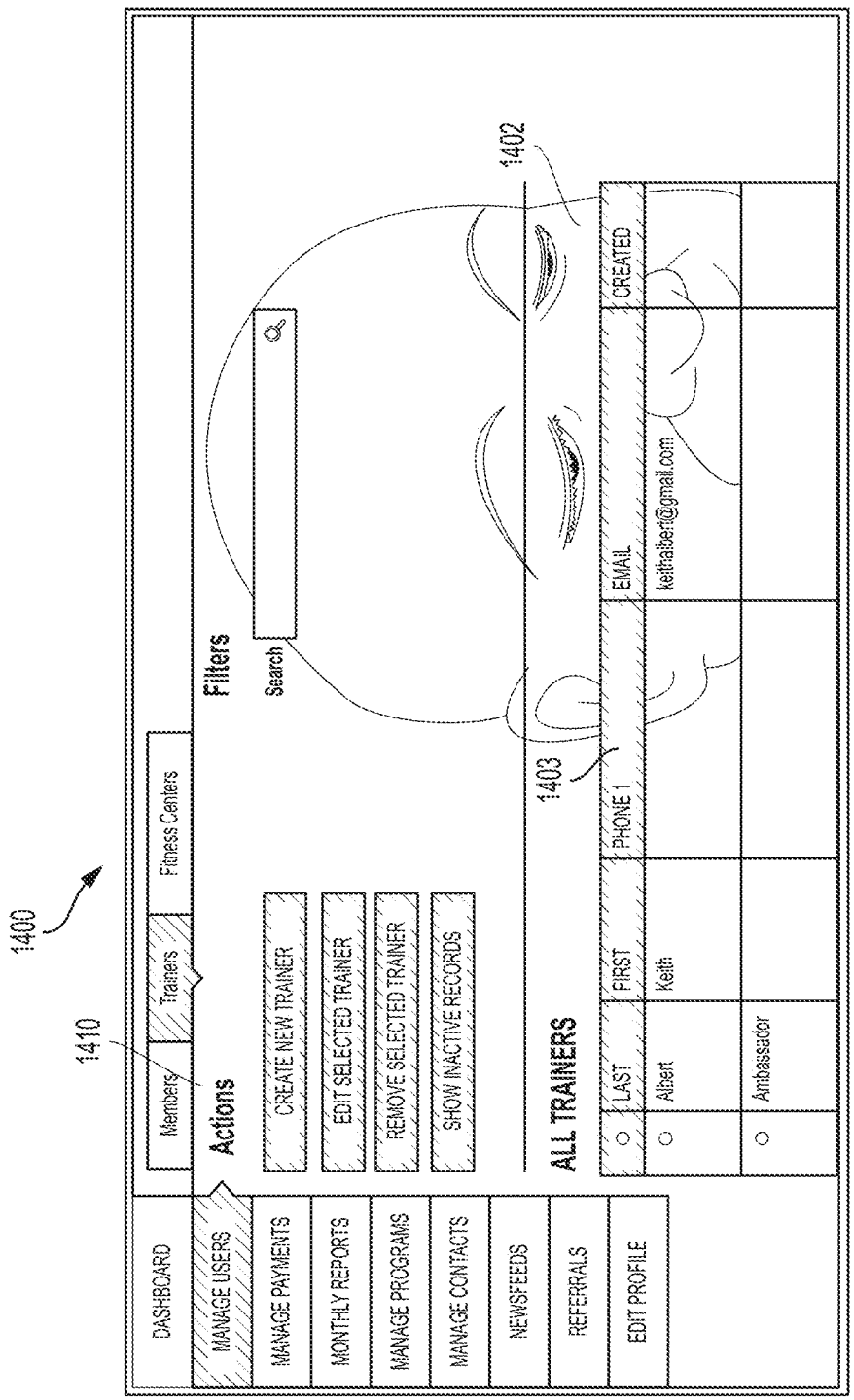
FIG. 14 is a screenshot image showing an example user interface for managing trainers, according to one embodiment.

FIG. 14 is a screenshot image showing an example user interface 1400 for managing trainers. In some embodiments, trainers may be employed by the fitness center. As with members, all trainers in the system may be displayed in the lower table 1402 that is sortable by clicking on the headers 1403. The action buttons allow an administrator to create, edit, or remove trainers from the platform. The actions panel buttons in action panel 1410 in the example in FIG. 14 may interact with the table 1402 below it. Each button represents a function that an administrator can take with trainers, such as:

Create New Trainer: Adds a new trainer in the system;

Edit Selected Trainer: Edit a selected trainer;

Remove Selected Trainers: Removes a trainer from the system;

Show Inactive Records: Display trainers that have been removed from the system.

In some embodiments, one or more fields in the interface 1400 may be used to associate a trainer with medical plans such as medical plans offered by employers of users. For example, a trainer may be indicated as a participating practitioner with a reimbursement agreement with an employer's medical plan such that fitness programs provided by the trainer to users with an eligible medical plan may be reimbursed. In some embodiments, one or more fields in the interface 1400 may include a validation logic to selectively present information related to reimbursement eligibility for a chosen trainer by a user based on pre-set reimbursement agreement data stored in the database.

In some embodiments, a create new trainer screen may be provided which may include the following sections:

Personal Information: These fields outline the basic information of the trainer. In some embodiments, the personal information fields may include an active checkbox to indicate a trainer is active in the system;

Back Up Trainers: If a trainer needs a backup up to a total of 2 can be selected for a specific trainer. This is for incidents such as sick time, personal time, vacation, etc. In some embodiments, the back up trainers fields may include Youngevity ID for the backup trainers if the Yongevity platform is being used;

Address: This is the physical address where the trainer lives;

Phone: This is the phone contact information of a trainer;

Notes: additional items to be added in relation to a trainer;

Bio: a biography for a trainer to be showcased so that members can be guided to connect to his trainer.

In some embodiments, an edit selected trainer screen may be provided to allow an administrator to edit the details of an existing trainer. This may be done by checking the box in the lower table 1402 and clicking the edit selected trainer button, or double clicking on a trainer in the table 1402. In some embodiments, the edit selected trainer screen may include the following sections:

Username and Password. In some embodiments, this section may include an Active Checkbox to indicate if the trainer is active in the system;

Current Associated Fitness Centers: This area shows the fitness centers that are currently associated to a trainer. In some embodiments, one may add new associations between trainers and fitness centers, but one may not be able to remove the default association generated when the trainer profile was created.

Current Available Hours. In some embodiments, a trainer can then add block out time on their own, these are overall hours a trainer is available to be scheduled for training in the system. This section may include:

Day: A pull-down showcasing the day that the trainer is available

Start Time: The time a trainer is first available

End Time: The last time a trainer is available

Current Associated Members: FIG. 15A is a screenshot image showing an illustrative example of the current associated member screen 1501. The table 1502 shows the members that are currently assigned to a trainer. To assign a member one may click the assign members button 1504 at the bottom of the screen in FIG. 15B. The table 1502 can update showing all of the fitness center members. In some embodiments, members can be added in bulk to a trainer in order to save time. FIG. 15B is a screenshot image showing an example screen 1505 for the assign members section. If a trainer needs to have 20 new members assigned to them, they simply can be selected from the table 1506 to the left, and added to the table 1508 in the right in FIG. 15B.

Remove Selected Trainers: to remove a trainer from the system, one may select the trainer from a table and check the box to the left of their name and click the remove selected trainers button. One can remove multiple trainers at one time.

Show Inactive Records: inactive records are trainers in the system that have been removed. If a trainer needs to be activated again administrators need to toggle the Show inactive records button. This may update the table and show all active trainers.

3.3 Manage Users: Fitness Centers

Figure 16:
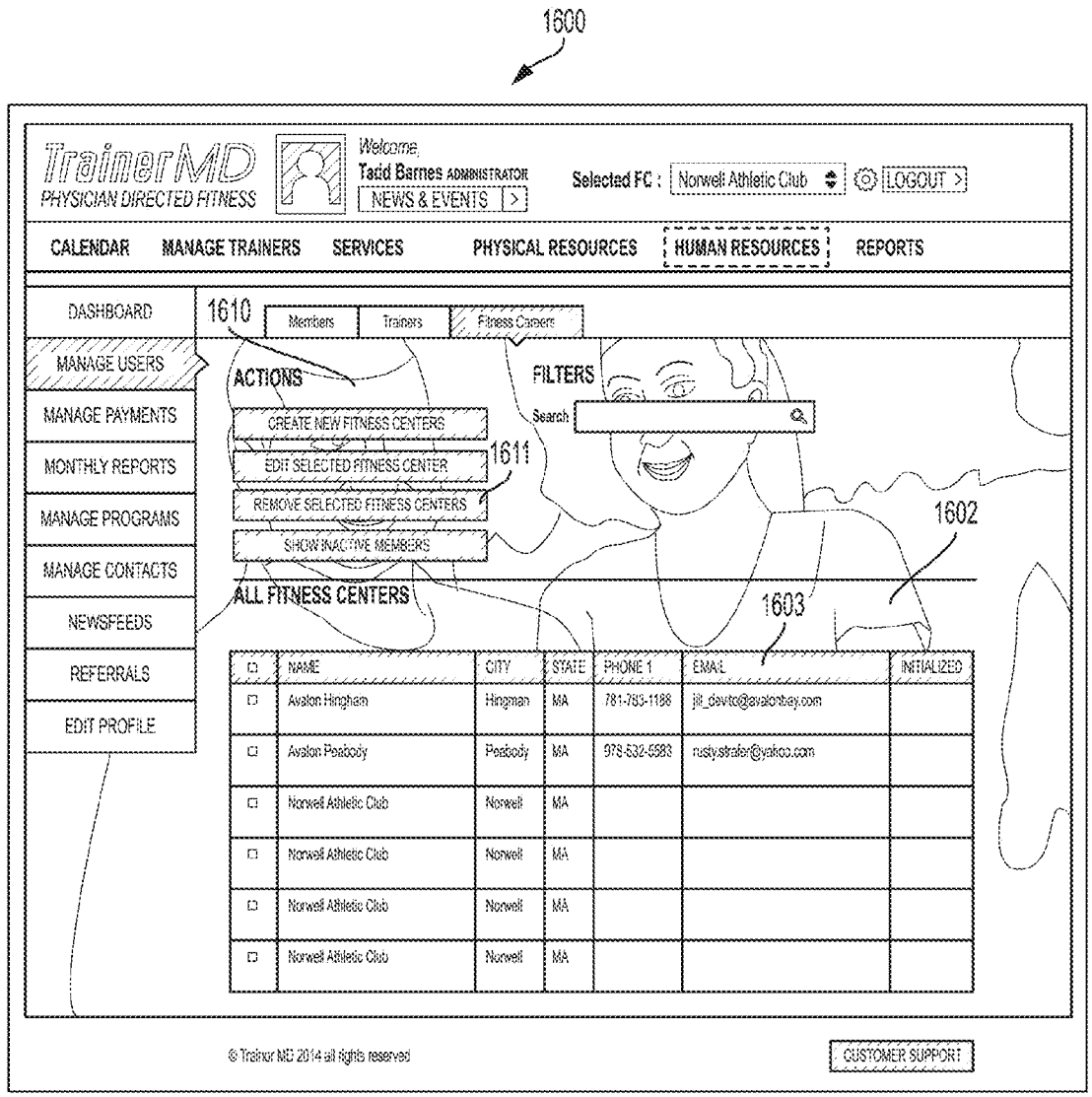
FIG. 16 is a screenshot image showing an example user interface, according to one embodiment.

FIG. 16 is a screenshot image showing an example user interface 1600 for managing fitness centers. In some embodiments, fitness facilities that have multiple fitness center locations, each with their own trainers and members, may be managed on this interface 1600. In some embodiments, as with the examples for members and trainers, all fitness centers in the system may be displayed in the lower table 1602 that is sortable by clicking on the headers 1603. The action buttons allow an administrator to create, edit, or remove fitness centers from the platform. The actions panel buttons 1611 in action panel 1610 in the example in FIG. 16 may interact with the table 1602 below it. Each button represents a function that an administrator can take with fitness centers, such as:

Create New Fitness Center: Adds a new fitness center in the system;

Edit Selected Fitness Center: Edit a selected fitness center;

Remove Selected Fitness Center: Remove a fitness center from the system;

Show Inactive Records: Display fitness centers that have been removed from the system.

In some embodiments, one or more fields in the interface 1600 may be used to associate a fitness center with medical plans such as medical plans offered by employers of users. For example, a fitness center may be indicated as a participating facility with a reimbursement agreement with an employer's medical plan such that fitness programs purchases or subscribed at the fitness center by users with an eligible medical plan may be reimbursed. In some embodiments, one or more fields in the interface 1600 may include a validation logic to selectively present information related to reimbursement eligibility for a chosen program at a fitness center by a user based on pre-set reimbursement agreement data stored in the database.

In some embodiments, a create new fitness center screen may be provided which may include the following sections:

Personal Information: this section may include fields such as name of the fitness center, email for the fitness center and an active checkbox to indicate if the account is active or not. In some embodiments, multiple email addresses as well as website information may be included for a fitness center in this section;

Phone: This is the phone contact information of the fitness center. Since a fitness center can have multiple phones the pull down allows for multiple phone types;

Notes: additional items to be added to a fitness center

In some embodiments, an edit selected fitness center screen may be provided which may include the following sections:

Username and Password: the fitness center's username and password can be entered here. The fields may be broken out as follows:

Login: The login name of the fitness center
Password: The fitness center's password
Name: Name associated with the fitness center user
Email: Email address associated with the fitness center
Active: If the fitness center is active or not Current Available Hours: These are hours and days that a fitness center is open for training. In order to add availability, one may click an add available hours button to update the area with the fitness center's availability. The data fields in this section may include day, start time and end time for when a fitness center is available. In some embodiments, adding availability may be performed for every day the fitness center is open. A fitness center may add block out time on its own.

In some embodiments, a remove selected fitness centers screen may be provided. To remove a fitness center from the system, simply select them from the table 1602 and check the box to the left of the name and click the remove selected fitness centers button. One may remove multiple fitness centers at one time.

In some embodiments, a show inactive records screen may be provided. Inactive records are fitness centers in the system that have been removed. If a fitness center needs to be activated again administrators may toggle the show inactive records button. This can update the table and show all active fitness centers. To reactivate the fitness center, one can toggle the show inactive records.

3.4 Manage Users: Other Users

In other embodiments, addition user roles can be defined an implemented. For example, a physician user role can implemented and managed to control access to patient health information. Physician users can be provided a greater level of access (assuming user permission) than for example, trainers. In some examples, trainer user roles and physician user roles can be defined and implemented separately.

According to another embodiment, processes can be assigned roles in the system to facilitate inheritance/grant of access privileges. For example, scheduler processes need to be able to access integrated systems and associated data to schedule resources at various facilities and/or reserve resources for users (e.g., patients, trainers, etc.).

4 Manage Payments

In some embodiments, a manage payments screen may be provided to show all payments in the system. A landing page may show a table of all the users in the system. It can also tally the total paid into the system, total monthly payments, and the total balance due to the fitness center above the table. Like other tables in some embodiments for the system all of the column headers are sortable, meaning if one click on member, start date, program, price, total paid, balance due, and status, the columns can sort in ascending or descending order. Also, as with other sections, the search field may begin suggesting results as one types into it. The action buttons are broken out as follows:

Enter Payment: Enter a new payment;
Edit Payment: Edit an existing payment.

In some embodiments, an enter payment screen may be provided where new payments are entered for members in the system. The screen may be broken out into the following fields:

Member: A pull-down featuring all members in the system attached to the specific fitness center Date: The date the payment was applied, the calendar widget in the right allows for a visual calendar to pick the date Method: A pull-down featuring the most common payment methods such as cash, credit cards, etc.

Program: A pull-down featuring all of the programs in the system. An admin should select the program the user is paying for here.

Payment Amount: The amount a member has paid with this new payment

Reference: An internal reference number if needed

Sessions: The number of sessions the member has done within that month and what they are paying for Notes: Any specific notes needed for this payment In some embodiments, an edit payment screen may be provided and entered by either double clicking on a payment in the table from the landing view, or checking the box next to a payment a member has previously made and clicking the edit payment button. This can then allow an administrator to make any edits to a previous payment and save it.

In some embodiments, one or more fields in the manage payment interface may be used to indicate reimbursement information associated with reimbursement from medical plans to pay for the programs. In some embodiments, the reimbursement information may include a list of reimbursement-eligible programs under a healthcare medical plan associated with a user or a user's employer for a given fitness center. In one example, the reimbursement information may be a prescribed list of training programs such as therapy programs that are reimbursable under a user's medical plan. In some embodiments, the manage payment interface may further provide a screen with interactive sections that assist a user to submit reimbursement claims for training expenses paid out of pocket. In one example, the interface may include an online-form for users to submit reimbursement requests with supporting documents to healthcare providers or medical plan administrators. In another example, the system according to aspects of the present application may automatically consolidate reimbursement information based on data stored on the database, generate and transmit reimbursement requests to external servers for processing by medical plans, without user input. According to some embodiments, automating reimbursement processing using the synergy afforded by the database (e.g., in the TrainerMD platform) providers time-saving benefits for the user as well as prevent inaccuracies in user-prepared reimbursement requests. Validation controls implemented in the user interface prevent errors in data input and can be further configured to constrain options presented to the user (e.g., limited the data that needs to be rendered in the user interface—correspondingly reducing memory and network bandwidth required to execute a reimbursement request).

In some embodiments, payments may not be limited to expenses related to training programs. In one example, incentive fitness bonuses may be provided as payments after a user completes a prescribed number of training activities, in order to encourage regular and frequent participation of training activities towards a steady and speedy recovery and/or improvement of a user's health. In some embodiments, fitness bonuses may be provided by medical plans in order to promote consistent maintenance of a user's health as a hedge for future medical expenses. In one example, the request and disbursement of incentive fitness bonuses may be automated based on data stored on the database without user input in order to save time and improve data accuracy.

5 Monthly Reports

In some embodiments, monthly reports screens are where all of the monthly reports for the system are accessible and/or maintained on the system. A fitness center may run this report at least once per month. Running the monthly report triggers a request on database to capture all of the data entered by the trainers for the members in the fitness center and generates the responsive data into a single report for each member. Members may then be able to access those reports in the system. If custom reports need to be generated they can be done here as well through the monthly report screens. As with other sections in some embodiments, a lower table can be visualized in the user interface that lists all of the current reports in the system and is sortable using the titles of each column in the table. A click on last name, for example, may cause the table to sort A-Z, but another click may cause it to sort from Z-A. The action buttons in the monthly reports function may be broken out as follows:

Process All Reports: This runs the reports for the system
Generate Custom Reports: This creates a custom report
Delete Reports: If a report needs to be removed due to any issue it can be done with this section.

In addition to action buttons, there are also custom filters for this section:

Month: Filter all reports based on month
Process Date: Filter all reports based on the date that they were processed in the system. Essentially this is a list of all reports made in the system.
Year: Filter all reports based on year
Email: Filter all reports based on an email address In some embodiments, a Process All Reports screen may be provided to run the reports. The fields on this screen may be broken out as follows:

Month: Select the month you want to process
Year: Select the year you want to process
Publish: Indicate whether one wants to publish the report results. In some embodiments, the Publish button can run the reports and generate and attach them to all users in the system. Once finished, all reports may be published in the system.

In some embodiments, a generate custom report screen may be provided to generate custom reports. Custom reports may be member specific. In some embodiments, an individual member, or members, may have the need for a special report over a specified period of time. For example a member may want a single report for their progress over the last 6 months. The fields are broken out as follows:

Select Members: A type ahead field that may suggest members for you as you type
Select Member area: This area shows all members in the left box, and selected members in the right box. An admin needs to find the member and single click on them and then click on the Add arrow to add them to the box. The Add All arrow may add all members in the system to the report.
Range: This is the date range area
Start Date: The starting date you want to run the report from
End Date: The end date of the report In some embodiments, a delete reports button may be provided to remove a selected report from the lower table.

6 Manage Programs

In some embodiments, training programs are packages that members purchase from a fitness center. Programs may first be added to the system (e.g., by a fitness center) before they are then assignable to members. In some embodiments, all program information may be entered before adding members into the system at the beginning so programs can be added as members are added. In some embodiments programs can also be added in bulk.

As with other sections in some embodiments, a lower table may be visualized that lists all of the current programs in the system and is sortable using the titles of each column in the table. A click on description, for example, may cause the table to sort A-Z, but another click may cause it to sort from Z-A. The action buttons are broken out as follows:

New Program: This button adds a new program into the system
Edit Program: This button edits a program that already exists in the system
Delete Program: This button removes a program from the system There may also be a filter panel on this section that is broken out as follows:

Description: This filters based on the description title
Price: This filters based on price
Service: This filters based on the service type, such as private and group training types Monthly: This filters based on this being a monthly program or not Member: A type ahead field that filters based on member name Filters can then be enabled and disabled as needed.

In some embodiments, a new program screen may be provided that allows creation of a new program in the system. The fields are broken out as follows:

Service: The service type of the program. This may display all of the services that are created in the service area of the main navigation. This includes private training and group training options Description: A description field of the service that you are creating Sessions: The total number of sessions a program has Sessions Monthly: The total number of sessions monthly this program may have Months: The total Months a program runs Session Minutes: The total minutes that count for one training session. The system defaults to 30 minutes equaling one training session, however this can be altered to meet each fitness center needs.

Price: The price of the program

Monthly: Is the program a monthly program? If so toggle this

Active: If the program is active. i.e. if the program is running and available

In some embodiments, an edit program screen may be provided to allow an admin to make additional changes to a program as needed. This can include cost changes, description changes, etc. This screen may also allow members to be added in bulk to a program. the edit program screen may include an associated members table with a list of associated members, as will be discussed in detail below.

In some embodiments, associated members are members that are part of a particular program. When a new program is added no members may be associated with it. In order to add members click the add members button. The edit program screen may update to the following fields:

Sales Staff: The staff member that sold this program;

Purchase Date: The date the members purchased the program;

Start Date: The date the program starts;

Price: The price of the package;

Down Payment: The payment a member made, if any, to start the program;

Initial Sessions: The number of initial sessions a member has with this program;

Available Sessions: The total number of sessions available to members;

Payment Day: The day payments are to be made;

Method: The payment method a user makes, such as cash, credit, etc.;

Payment Amount: The amount a member has paid;

Members selection area: This allows an administrator to add members in bulk to this program.

Once members have been added they may then display in the associated members table.

In some embodiments a delete program button may be provided to remove a selected program from the lower table.

7 Manage Contacts

Figure 17:
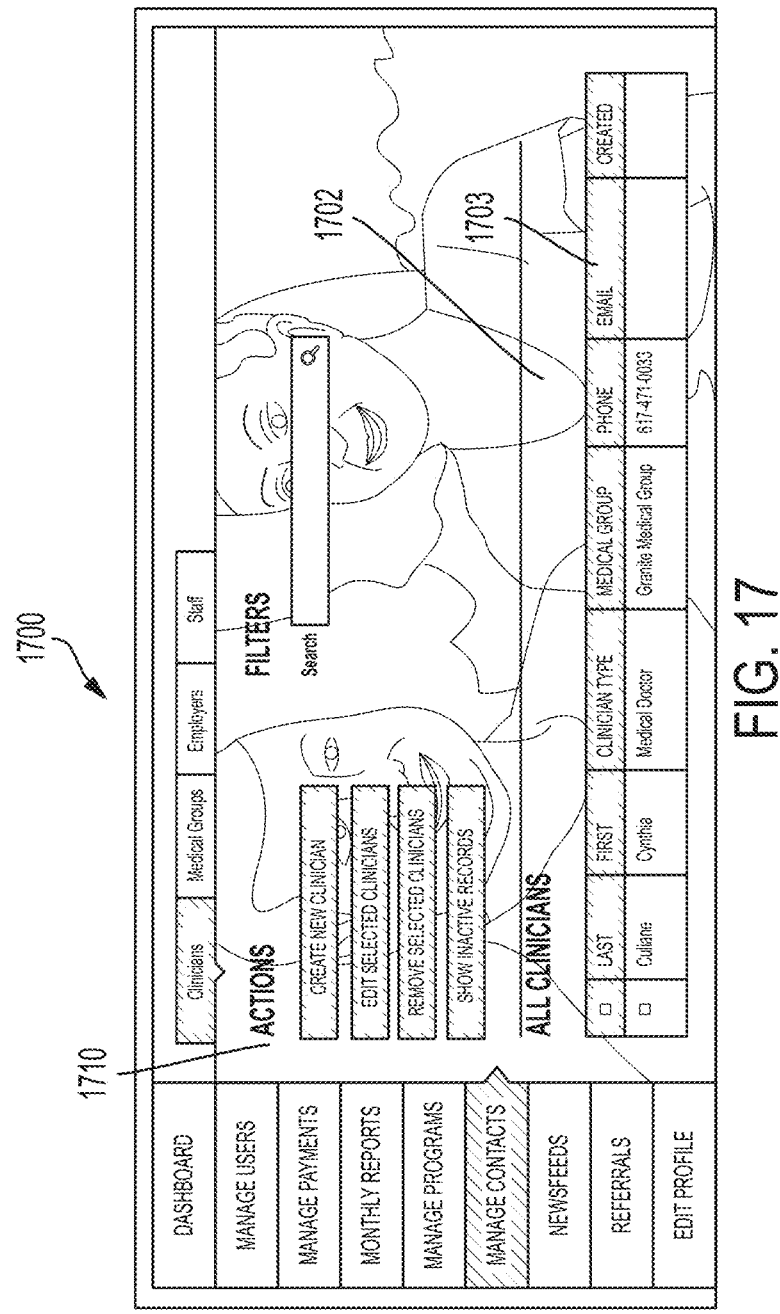
FIG. 17 is a screenshot image showing an example user interface, according to one embodiment.

In some embodiments, contacts are categories or types added to a member. An interface for managing contacts in the system may be provided. FIG. 17 is a screenshot image showing an example user interface 1700 for managing contacts. The user interface 1700 may include the following tabs:

Clinicians: These are health professionals that are connected to members;

Medical Groups: These are groups that the clinicians are part of;

Employers: If a corporation is using a training center, they may be added in this area;

Staff: This is where the sales staff for the fitness center is added.

As with other sections in some embodiments, a lower table 1702 may list all of the contacts in the system and is sortable both ascending and descending using the titles of each column 1703 in the table. A click on Last Name for example, may cause the table to sort A-Z, but another click may cause it to sort from Z-A.

7.1 Manage Contacts: Clinicians

Clinicians are health professionals that can be attached to members. In some embodiments, action buttons 1710 for managing clinicians may be provided as follows:

Create new clinician: This creates a new clinician in the system;

Edit Selected Clinician: This edits an existing clinician in the system. This can also be accomplished by double clicking on the clinician in the lower table;

Remove Selected Clinicians: This removes a clinician from the system;

Show Inactive Records: This displays all removed clinicians from the system;

Search Filter: A type ahead search field that suggests words as a user types them.

In some embodiments, a create new clinician screen may be provided and be broken out into the following sections:

Personal Information: This is where the basic personal information of a clinician is added. The fields are broken out as follows:

Title: The title of the clinician, such as Doctor

First: Clinician's first name

Last: Clinician's last name

Email: Clinician's email address

Medical Group: This is a pull-down that displays all of the medical groups in the system. Medical groups may be added prior to adding a clinician.

Clinician type: This is a pull-down that displays the types of clinicians in the system such as Medical Doctor, Nurse Practitioner, etc.

Active: If the clinician is active in the system or not

Phone: This is the phone contact information of the clinician. Since a clinician can have multiple phones the pull down allows for multiple phone types.

Address: This is the physical address where the clinician resides:

Notes: Notes are additional items to be added to a clinician.

In some embodiments, an edit selected clinician screen may be provided to allow an admin to edit the details of a clinician in the system. In some embodiments, this feature may also allow an admin to associate multiple members to a clinician.

To assign members to a clinician, one may in the edit screen click assign members. If members are already assigned they may appear in the lower table in the edit screen. Once assign members is clicked the area may update to the member selection screen. In some embodiments, all fitness center members are in a left area of the screen, and the selected members for the clinician are in the right area. A member in the left area may be added by selecting using the large window or typing the members name in the search field and clicking the add button. Members can be removed by highlighting them in the right table and clicking the remove button. In some embodiments, all members can be added by clicking an add all members button, and removed by clicking the remove all members button.

In some embodiments, a remove selected clinicians screen may be provided to remove clinicians from the system by clicking the checkbox next to their name in the lower table 1702 and then clicking the remove selected clinicians button.

In some embodiments, a show inactive records screen may be provided to show inactive records. The screen may display all clinicians that have been removed from the system. As with other sections in some embodiments, inactive clinicians may be reactivated by double click on the clinician that should be reactivated, and then toggle the Active checkbox.

7.2 Manage Contacts: Medical Groups

Figure 18:
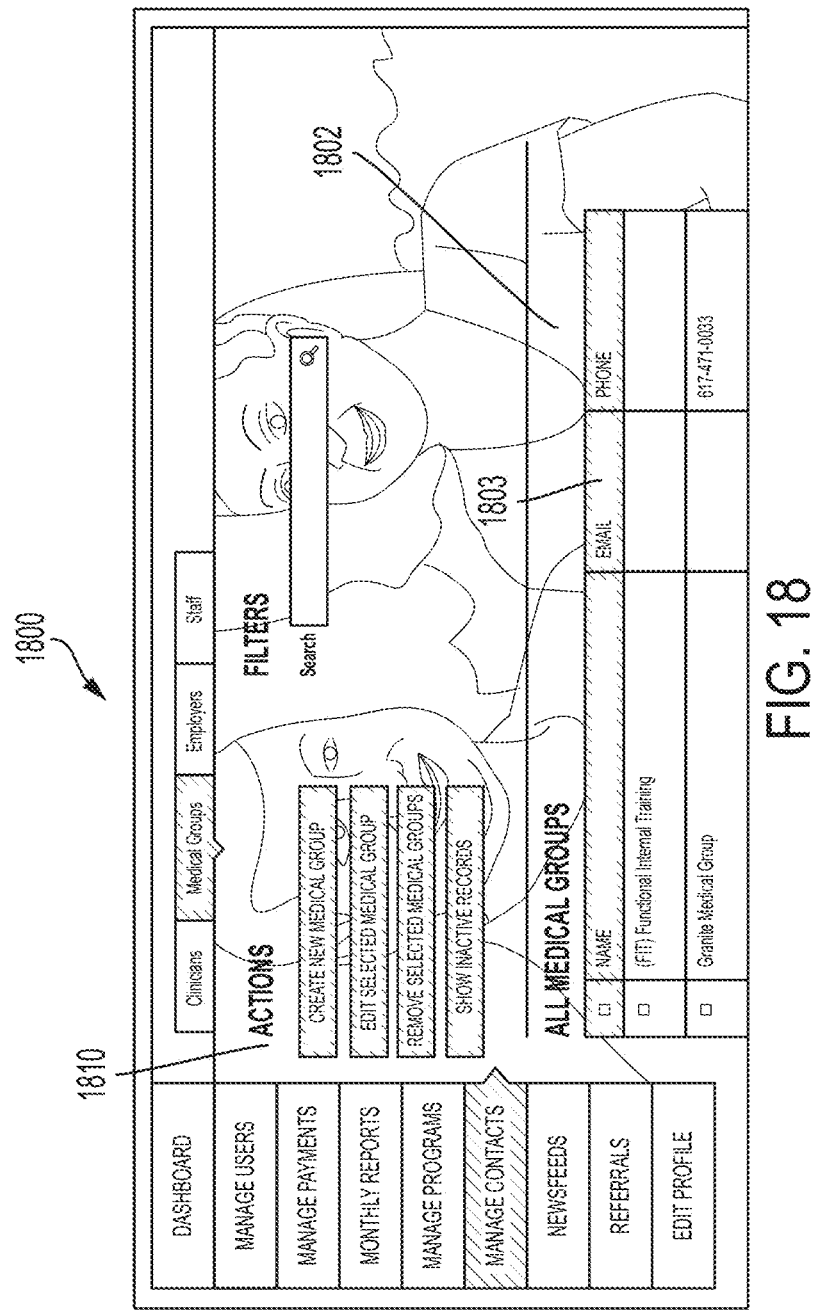
FIG. 18 is a screenshot image showing an example user interface for managing medical groups.

According to one embodiment, medical groups are organizations that groups of clinicians belong to. FIG. 18 is a screenshot image showing an example user interface 1800 for managing medical groups. The user interface 1800 may include action buttons 1810 as follows:

Create New Medical Group: This creates a new medical group in the system;

Edit Selected Medical Group: This edits a selected medical group. This can also be performed by double clicking on a medical group in the lower table;

Remove Selected Medical Groups: This removes medical groups from the system;

Show Inactive Records: This displays medical groups that have been removed;

Search Filter: A type ahead search field that suggests words as a user types them.

As with other sections in some embodiments, a lower table 1802 may list all of the contacts in the system and is sortable both ascending and descending using the titles of each column 1803 in the table.

In some embodiments, a create new medical group screen may be provided to create new medical group or medical groups. The fields in the screen may be broken out into the following sections:

Personal Information: This is the personal information for the medical group

Name: The name of the medical Group

Web Site: A website of a medical group

Email: The email address of a medical group

Address: This is the physical address for the medical group:

Phone: This is the phone contact information of the medical group. In some embodiments, a medical group can have multiple phones and a pull down menu allows for multiple phone types. In some embodiments, a location Pull-Down menu allows input for different type of phone a medical group may have.

Notes: Notes are additional items to be added to a medical group.

In some embodiments, an edit selected medical group screen may be provided to allow an admin to update the details of a specific group. This screen may also display the clinicians associated with this medical group.

In some embodiments, a remove selected medical groups screen may be provided to allow an admin to remove a selected medical group. An admin may toggle the checkbox next to the medical group that is to be removed and click a button to perform the removal.

In some embodiments, a show inactive records screen may be provided to display all medical groups that have been removed from the system. As with other sections in some embodiments, one may double click on the medical group that should be reactivated, and then toggle the active checkbox.

7.3 Manage Contacts: Employers

Figure 19:
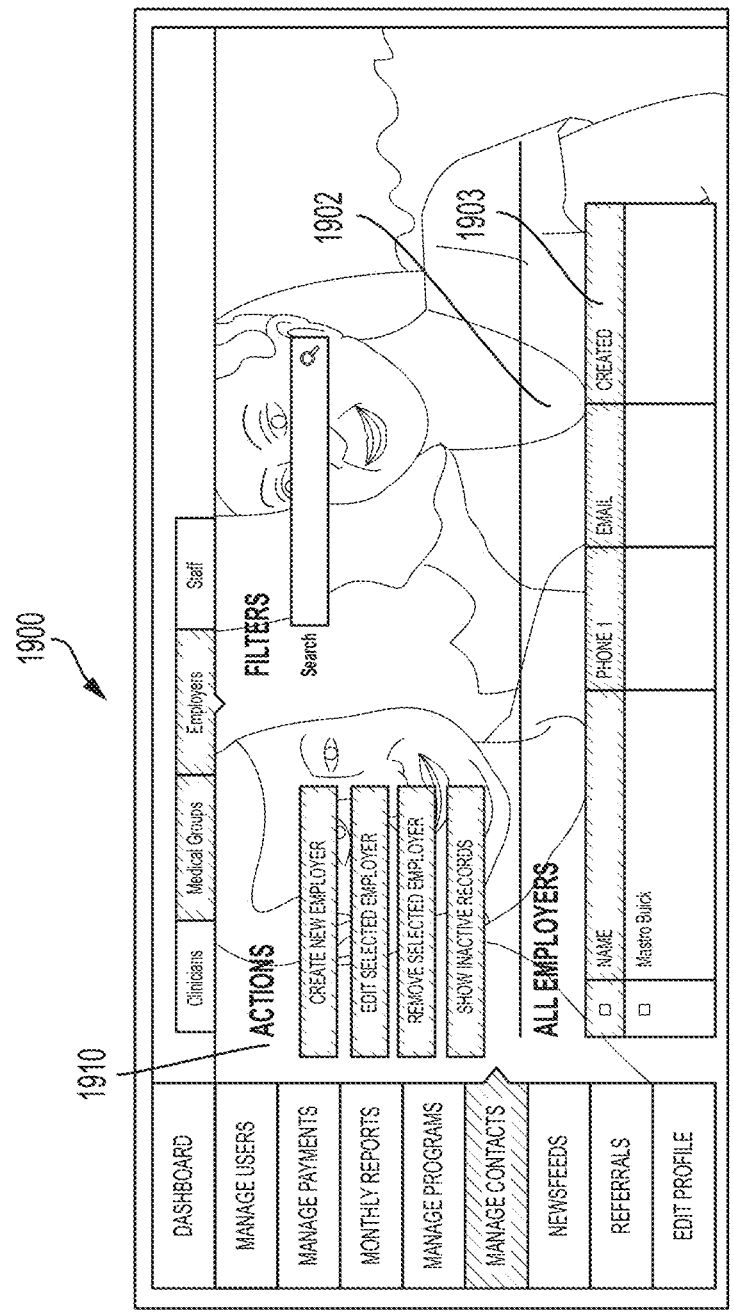
FIG. 19 is a screenshot image showing an example user interface, according to one embodiment.

According to one embodiment, employers are groups that members belong to. In some embodiments, the employers section is provided such that corporations that have a wellness program that employees can join may manage their associations with the members and other aspects of the platform. FIG. 19 is a screenshot image showing an example user interface 1900 for managing employers. The user interface 1900 may include action buttons 1910 as follows:

Create New Employer: This creates a new employer in the system;

Edit Selected Employer: This edits a selected employer. This can also be performed by double clicking on an employer in the lower table;

Remove Selected Employer: This removes employers from the system;

Show Inactive Records: This displays employers that have been removed;

Search Filter: A type ahead search field that suggests words as a user types them.

As with other sections in some embodiments, a lower table 1902 may list all of the contacts in the system and is sortable both ascending and descending using the titles of each column 1903 in the table.

In some embodiments, a create new employer screen may be provided and may be broken out into the following sections:

Personal Information: This is the personal information for the employer which may include name, web site address and email of an employer;

Address: This is the physical address where the employer resides

Phone: This is the phone contact information of the employer. In some embodiments, since an employer can have multiple phones a pull down menu allows for multiple phone types.

Notes: Notes are additional items to be added to an employer.

In some embodiments, an edit selected employer screen may be provided that allows an admin to update the details of a specific group. This screen may also displays the members associated with this employer.

In some embodiments, a current associated members screen may be provided that shows the members that are associated with this employer. Members can be assigned from the member creation screen listed above, or in bulk from this screen. In some embodiments, all fitness center members may be in the left area of the screen, and the selected members for the employer are in the right area. One may select a member in the left area by using the large window or typing the members name in the search field and clicking the add button. Members can be removed by highlighting them in the right table and clicking the remove button. All members can be added by clicking the add all members button and removed by clicking the remove all members button.

In some embodiments, a remove selected employers screen may be provided that allows an admin to remove a selected employer. An administrator may toggle a checkbox next to the employer that is to be removed and click a button.

In some embodiments, a show inactive records screen may be provided to display all employers that have been removed from the system. As with other sections in some embodiments, one may double click on the employer that should be reactivated, and then toggle the active checkbox to reactivate an employer.

7.4 Manage Contacts: Staff

According to one embodiment, staff are employees of the fitness center that aren't trainers or administrators. The action buttons for an interface for managing Staff may be broken out as follows:

Create New Staff: This creates a new staff member in the system;

Edit Selected Staff: This edits a selected staff member. This can also be performed by double clicking on a staff member in the lower table;

Remove Selected Staff: This removes staff members from the system;

Show Inactive Records: This displays staff members that have been removed;

Search Filter: A type ahead search field that suggests words as a user types them.

In some embodiments, a create new staff member screen may be provided with fields as follows:

Name: Staff member's name;

Position: A pull-down displaying various position types such as sales, front desk, etc.;

Email: Email address of the staff member;

Start Date: The date a staff member has started;

Active Checkbox: If the staff member is active in the system or not;

Phone: The staff member's phone number.

In some embodiments, an edit selected staff screen may be provided that allows an admin to update the details of a specific staff member.

In some embodiments, a remove selected staff screen may be provided that allows an admin to remove a selected staff member. An admin may toggle the checkbox next to the staff member that is to be removed and click this button.

In some embodiments, a Show Inactive Records screen may be provided to display all staff members that have been removed from the system.

8 Manage Newsfeeds

In some embodiments, news feeds are blocks of content that appear on the dashboards for all members in the system. As with other sections in some embodiments, a lower table can be visualized on an interface and may list all of the news feed items in the system, and is sortable both ascending and descending using the titles of each column in the table. The interface may include action buttons such as the following:

Create New News Feed Item: Creates a new news feed post;

Edit News Feed Item: Edits an existing news feed post;

Delete News Feed Item: This deletes a news feed item.

There may also be a series of filters for news feed items. Those filters are broken out as follows:

Audience Type: There are various audiences that a news post can be displayed for;

Expiration Date: Display only news items with a specific expiration date;

Created: Display news items based on a creation date;

Title: Display news items based on the title;

In some embodiments, a create new news feed item screen may be provided with elements outlined below:

News Feed: which may include sub-fields such as the following:

Title: This is the title of the news feed item

Created: The creation date of the news feed item. The calendar widget allows for a visual date picker.

Expires: The expiration date of the news feed item. The calendar widget allows for a visual date picker.

Active: If the news feed item is active and live on the site

Audience: This displays the audiences within the system that may see the news post. The system defaults to global but can be customized.

Audience Type: A pull-down that selects the various audience types in the system. Examples include, fitness company, trainer, employer, etc.;

Fitness Company: If fitness company is selected in audience type, the company itself can be selected here;

Fitness Center: if fitness center is selected in the audience type, the fitness center can be selected here;

Trainer: If Trainer is selected in the audience type, the trainer is selected here;

Employer: If employer is selected in the audience type, the employer is selected here;

Medical Group: If medical group is selected in the audience type, the medical group is selected here;

Clinician: If clinician is selected in the audience type, the clinician is selected here.

Message: The message post is added in this area.

In some embodiments, an edit news feed item screen may be provided that allows an admin to edit the content or audience of an existing news feed item. This can also be accomplished by double clicking on a news feed item in the lower table.

In some embodiments, a delete news feed item screen may be provided that allows an admin to remove a news feed item from the system.

9 Manage Referrals

According to one embodiment, referrals are users who have either signed up for the service using the form on the main website or entered in the system by an admin. In some embodiments, an interface may be provided with a lower table that lists all of the referrals in the system, and is sortable both ascending and descending using the titles of each column in the table. The interface may comprise action buttons such as:

Create New Referral: Creates a new referral in the system;

Edit Referral: Edits an existing referral;

Deleted Referral: This deletes a referral.

In some embodiments, a create new referral screen may be provided which may include the following sections:

Personal Information

Assignments

Health Club: The health club that referred this member

Employer: The employer of the referral

Physician: The physician of the referral

Location Information

Message: If a referral fills out the form on the main website the message they left may appear in this field.

In some embodiments, an edit referral screen may be provided that allows an admin to edit the details of a referral in the system. This can also be accomplished by double clicking on a referral listed in the lower table.

In some embodiments, a delete referral screen may be provided that allows an admin to delete a referral in the system. Deleting unwanted or outdated referrals or other associated information may help reduce the storage footprint of the system and reduce the amount of bandwidth wasted on messages from unsolicited and/or unwanted sources such as spam messages.

10 Edit Profile

In some embodiments, an edit profile screen may be provided for one or more admin user to modify their name, email address, authentication credential or any other associated values.

Various implementations include combinations of the following elements: (1) Online Virtual Patient Center (VPC) HIPAA Compliant Preventive Health Management Platform; (2) Onsite Testing and Best Practice Lifestyle Education, Training and Support Service Model; and (3) Medical, Fitness and Wellness Provider Network. The various embodiments prevent care gaps by providing physicians with health performance data streams and feedback to help them make better decisions as they direct patients towards preventive health programs.

For example, the platform facilitates: physicians engaging patients in high quality affordable preventative health education and training programs; guiding patients towards approaches tailored to their individual needs; motivating patients to achieve goals and maintain their results; collect, track, manage and document results and feedback to share with health care providers; protect patient privacy with enhanced security; develop preventive health programs and update machine learning approaches; and enable partners (e.g., integrated systems to continually focus on enhancing the patient experience to drive engagement and results).

In some examples, the system automates interactions with user to automatically present and develop the following targets: generate physician directed fitness referral; complimentary patient consultation with physician; readiness assessment (e.g., includes health history capture, brief workout and fitness test directed by automated/virtual trainer); fitness and nutrition education overview via integrated systems; develop phased timeline for health goals; program discussion and trainer recommendations (e.g., live trainer and/or virtual trainer recommendations); communicate lifestyle education & support workshops; automated meal planning, food journaling via voice commands with nutrition support; execute fitness testing, vitals collection, personalized performance reports, feedback and results; which can all be made available and/or executed through a virtual patient center (VPC}—which provide patients and physicians access under rigid security.

API integration preserves security and at the same time facilitates a single point of entry interface to a variety of third party systems. For example, online meal planning, nutrition tools, goal tracking and health management with accountability built in are made accessible via the VPC; automated appointment and secure communication system for online booking and 24/7 convenience that can even execute automatic scheduling on behalf of the user; device pairing enables patients to customize monitoring multiple medical devices in one place, receive reports and have a physician review and analyze their health data; and device pairing also enable patients to customize multiple online services via the secure VPC.

Various embodiments are configured to enable physicians, patients, trainers and administrators, rigid security, flexibility, transparency, and accountability. The system embodiments manage human resources, physical resources, visits, multiple users, remote devices, and services linked to users and data at multiple-facilities.

In other examples, patient data is collected and entered into the VPC. The patient data can includes body fat percentages, muscle quality, CNS responses, body measurements, weight, strength changes, flexibility changes, cardiovascular changes and more. Patients can complete monthly fit tests, that are automatically tracked and securely stored on the system. Monthly reports can be automatically generated that include professionals notes related to patient progress or concerns. Each month a personal patient report is automatically generated on the patient/member home page and made accessible through the VPC.

The VPC platform can integrate and manage medical devices and/or sports devices securely from the user home page or via a secure application installed on a user device. Multiple devices are configured to communicate with the system for secure downloading, managing and documenting of the information collected by the device. The pairing through the VPC gives physicians, trainers, coaches and others access to data with the flexibility to access the data securely anywhere where they have a web connection. So long as the patient has granted access.

Figure 20:
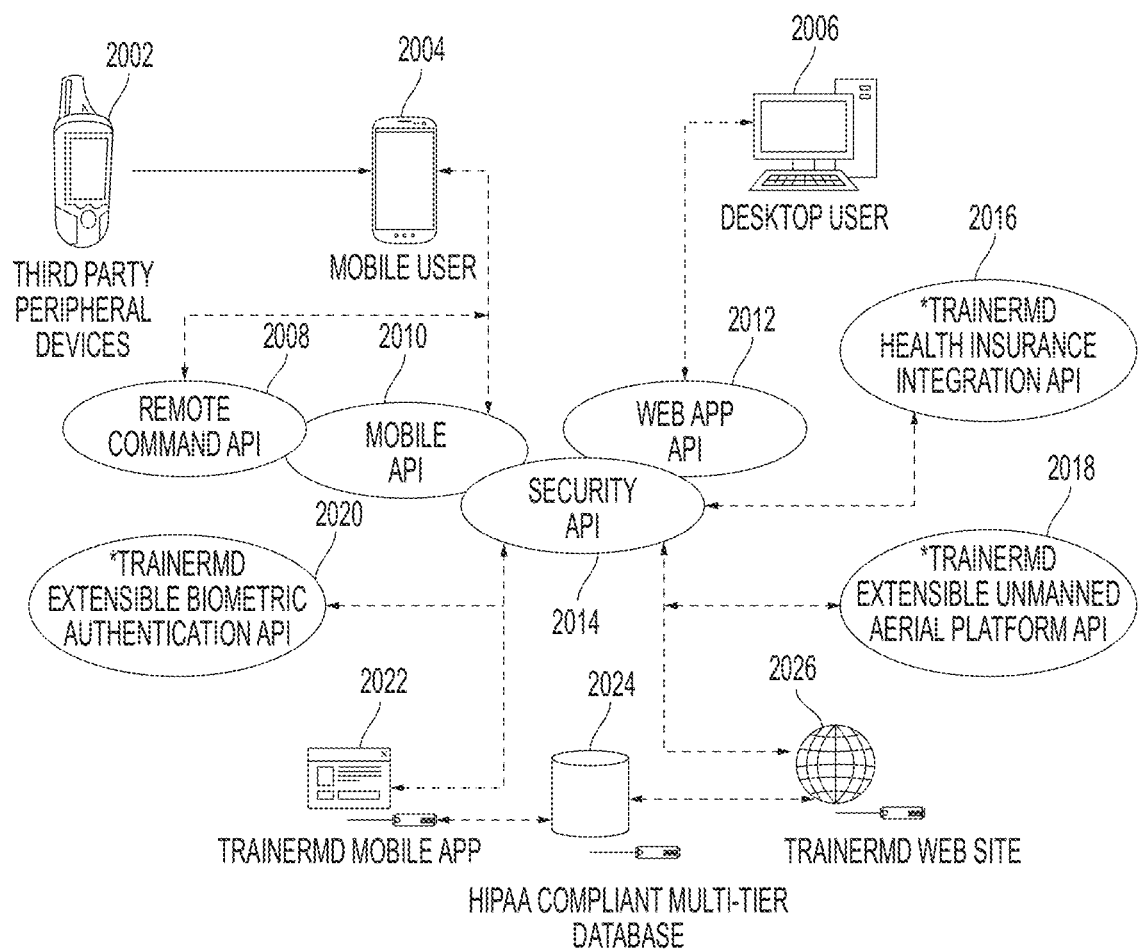
FIG. 20 is an example of a health integration platform and database system for executing multi-tier data and multi-platform data access requests.

FIG. 20 illustrates an example implementation of a health integration platform and database system for executing multi-tier data and multi-platform data access requests. Shown is a TrainerMD platform that can incorporate any of the features discussed herein. Some example features are described, but various embodiments of the TrainerMD platform can incorporate any of the functions discussed herein. Shown in FIG. 20 is a health monitoring device and/or peripheral devices (e.g., 2002) that can communicate with the system. Mobile users 2004 can access the system via a downloaded application (e.g., TrainerMD mobile app 2022 and mobile app API 2010) or via a desktop (e.g., 2006) and website (e.g., TrainerMD website 2026 and web app API 2012). User can also interact with the system via a remote command API 2008 which can be configure to handle verbal commands issue by the user via peripheral devices 2002 and/or a mobile device. Regardless of the vehicle for accessing the system, authentication is controlled, for example, by a security API 2014 configured to manage system access and authenticate any access, for example to the HIPAA compliant multi-tier database 2024. The security API 2014 can handle user access as well as manage access by or through integrated system (e.g., third party integration systems: health insurance API 2016 integrates insurer platforms and can manage reimbursement requests, unmanned aerial platform integration (i.e., drone)) via API 2018). In some embodiments, the security API 2014 can also be configured for enhanced authentication, for example, using biologic patterns to authenticate users (e.g., matching a user's heart rate pattern over time). In further examples, the security API 2014 can interact with a biometric authentication API (e.g., 2020) to perform some enhanced authentications. For example, biologic data pattern matching can be implemented via API 2020 and/or via API 2014.

According to one embodiment, a physician can access the system to prescribe or order a fitness program (e.g., a TrainerMD Program) for a patient, the system provides user interfaces to enter the request. For example, the system can receive the physician request via entry of patient into database as a TrainerMD preventive health referral. This can also occur as a patient or user requests to join the system (e.g., TrainerMD system "TMD") by registering on an associated website (e.g., the TrainerMD website). Once received, the system schedules trainers or other TMD preventive health provider resources (or requests trainers or other providers respond), schedules facilitate resources, and the session is initiated. In some examples, the system can automatically schedule and/or reserve the appropriate personnel and resources.

During execution of the session the user's biologic data and/or any other sensor data is communicated from the user' devices and associated with access tiers in the database. Physician are permitted to access to the system to review the results. Trainers can also accesses the system to view the results and tailor a next session.

In some embodiments, the system's (e.g., the TrainerMD) solution begins when a user is either referred by a physician, in which case a user account is either provisioned or a referral code is created to supply at time of registration, or when a user self-enrolls through an associated website (e.g., the TrainerMD website) or downloaded application. Once enrolled and active, a user profile is established and complete, the system is configured to activate the user's ability to modify data, use the secure communication system, set goals, interact with third party solutions including nutrition apps (and for example more systems), use the scheduling system (e.g., TrainerMD scheduling system), and manage payments.

If the user is utilizing, for example, the TrainerMD solution in conjunction with an approved and integrated device such as an approved blue tooth headset with a heart rate monitor (e.g., paired with a mobile application), then the user will be allowed to access and execute respective functions through a Remote Command Center API (e.g., including a verbal command interface) while logged in and authenticated. In some embodiments, a new measure of biometric authentication can be executed through a custom security API—the security API can use a server side algorithm to identify and authenticate a user to the platform using their historically recorded and known resting heart rate as an additional multi-factor authentication service or security control to protect the compromise of their HIPAA protected information.

In another embodiment, if a user schedules a session, the system provides a form for a user to complete and submit to the website or via downloaded mobile applications which are configured to forward the data to the system (and, for example, a TrainerMD Data API) which is configured to process the request for security and check for availability of the resources requested, facility, and provider(s). If the system determines that these conditions are met, then the session is scheduled, for example, in the TrainerMD multi-tier database. A confirmation can then be sent to the user, facility hosting the space and resources, and/or the providers involved. In some embodiments, the system is configured to identify a closest fit solution for allocating resources, facilities, trainers, and timing—and present the options for acceptance to the user.

In further embodiments, if the services requested require payment, then an invoice can be generated to the user account and stored securely within the system (and e.g., a TrainerMD multi-tier database). Users can access feedback reports generated automatically and communicated to them on periodic and manual intervals. The reports enable the user to track progress and performance. These patient reports can be access through a patient home page in the user interface. The system is also configure to provide hard copy of the reports, for example, by a print request in the interface executed by the patient. Patient reports may be accessible to medical physicians at the patient/members request, in addition to other respective providers such as trainers and coaches, etc. (again by patient request or authorization grant).

This process will enable providers to better tailor fitness and wellness efforts to improve the quality of life for the user and such communications can be accomplished by means of the TrainerMD solution's secure communications channels.

The system (e.g., a TrainerMD solution) is configured with embedded procedures to provide automated outputs to better enhance the effectiveness of the platform, increase user satisfaction, and provide automated exploratory functions to discover new capabilities. By utilizing data gained from user input, provider input, third party equipment such as monitoring and exercise devices, and the system (e.g., TrainerMD system) can implement an educational curriculum, and predictions can be derived. Examples of predictions include patterns of exercise and lifestyle behaviors between groups and individuals—which may include predictions on diet and rest based on matching patterns. Furthermore, additional concepts can be mined to include the production of an algorithm which could best determine relocation options for a trainer geographically based on the link analysis of many different dimensions for multi-tier relational sets (e.g., linking past client performance improvements vs. client satisfaction rating vs. trainer availability ratio vs. trainer educational level, among other examples). Additionally, predictive analytic algorithms are implemented to process out-of-focus data such as relations between different user organizations, marketing trends, and system performance statistics, for example, to better align business strategies which might supplement the experience of users. (e.g., partnering with medical device companies after discovering a trend of users reporting that they use blue tooth headsets with heart rate monitoring devices in feedback).

Various embodiments, implement any one or more algorithms for pattern detection, pattern matching, relationship fitting, etc. One example algorithm includes determining a Comprehensive Workplace Wellness Readiness Factor (CWWRF): (this example algorithm is executed to produce a relative index on how prepared the geographic area is to engage in workplace wellness activities). In one implementation CWWRF is calculated as follows: Number of Trainers in Geographic Area (NumT)*Number of Providers (NumP)*Number of Facilties (NumF)*Number of Hours of Coverage (NumC)/Number of Members (NumM)=CWWRF. As discussed, various embodiments implement predictive analytics to develop fitness programs.

Example System Enhancements

In some embodiments, access to user's biologic data over time enables the system to build unique mappings or patterns of biologic data to the user who is being monitored. With such unique data (e.g., patterns of biologic information), the system can use the patterns and/or biologic signatures for the user (e.g., any one or more or any combination of pulse, respiration, CNS activity, etc.) captured over time. The unique signatures can be used as means of authenticating particular users. For example, to authenticate a captured pattern must match historic patterns in order to authenticate the user. In another example, a biologic pattern can be used as a seed to an encryption algorithm.

Further extension exists that use specific ones of sensor readings being obtained either by a user's mobile device or a health monitoring device. Voice patterns and other biologic data can be matched to a user's mood. Periods of happiness, stress, anger, duress, etc. can be tracked and used to facilitate mental health analysis (e.g., by a physician or via automated analysis and recommendation).

In another embodiment, the central system can be configured to automatically control remote devices associated with the user and/or user's mobile device. In one example, a user can pair a drone (e.g., remote control or semi-automated flying vehicles) with the secure application. The central system can automatically operate the drone and any attached camera to capture, for example, exercise activity done by the user. In one example, the user can select a follow me options, and the central system can control the drone automatically. In one example, the central system executed commands on the drone via the secure application. In another example, the secure application can track a user's (or device's) current position using GPS and issue commands to the drone to stay in proximity and/or record the user's positions. In yet other implementations, the central system itself can include drone distribution nodes, and a user can request a drone follower. The system can automatically pair the user device and drone to enable video capture and a follow mode (e.g., follow me on my run route). In some settings, this feature can be implemented as an emergency response feature. For example, in response to a 911 indication via the secure application the system can call emergency services and dispatch a drone to capture video at the emergency location. In other examples, if the system detects an injury event (e.g., rapid deceleration) via sensor data, the system can be configured triggered a visual and/or audio prompt to the user's device—and in the absence of a response dispatch a drone or if the user indicates that they are injured dispatch a drone and trigger and emergency response (e.g., via 911 e911).

Various aspects and functions described herein may be implemented as specialized hardware or software components executing in one or more specialized computer systems. There are many examples of computer systems that are currently in use that could be specially programmed or specially configured. These examples include, among others, network appliances, personal computers, workstations, mainframes, networked clients, servers, media servers, application servers, database servers, and web servers. Other examples of computer systems may include mobile computing devices (e.g., smart phones, tablet computers, and personal digital assistants) and network equipment (e.g., load balancers, routers, and switches). Examples of particular models of mobile computing devices include iPhones, iPads, and iPod Touches running iOS operating systems available from Apple, Android devices like Samsung Galaxy Series, LG Nexus, and Motorola Droid X, Blackberry devices available from Blackberry Limited, and Windows Phone devices. Further, aspects may be located on a single computer system or may be distributed among a plurality of computer systems connected to one or more communications networks.

Figure 3:
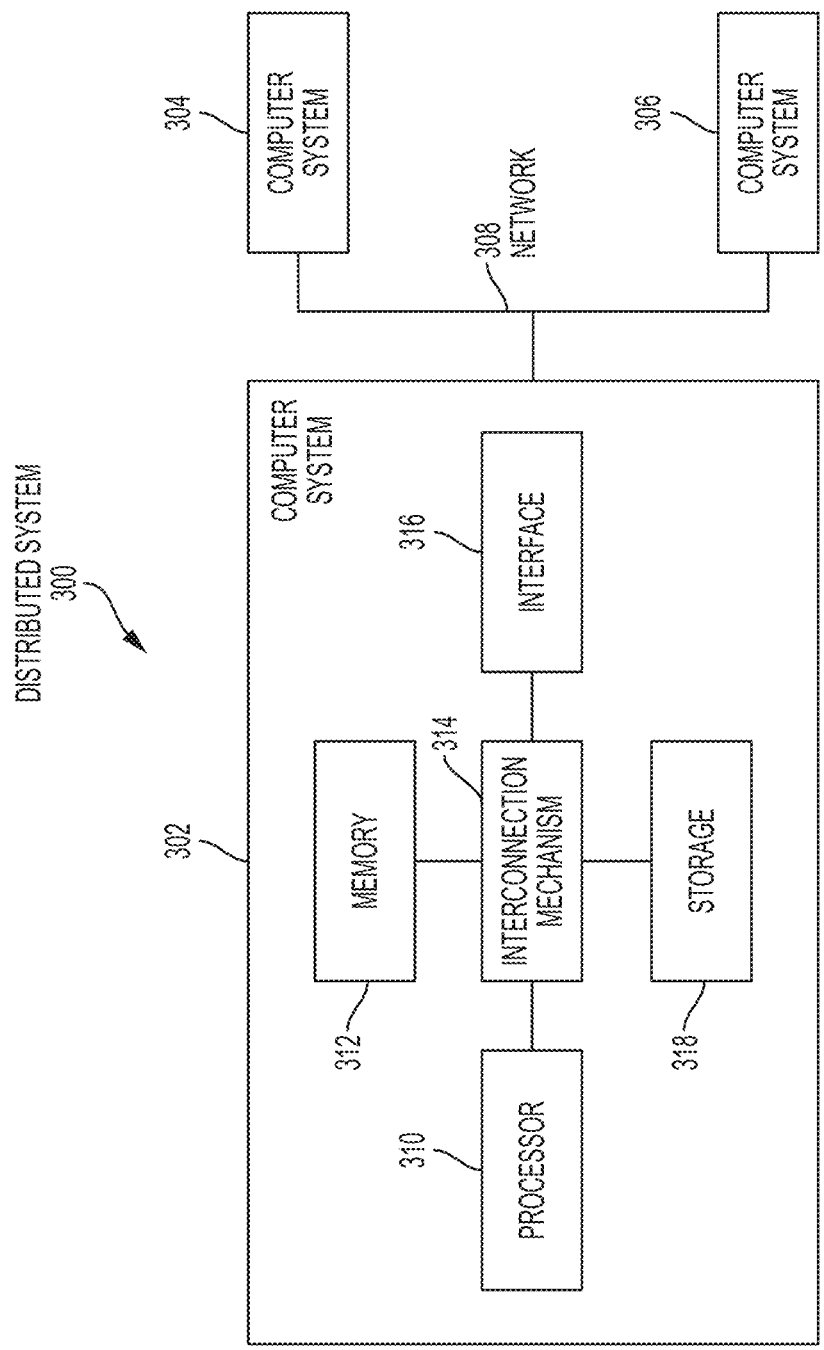
FIG. 3 is an example specialized computer system, according to one embodiment.

For example, various aspects, functions, and processes may be distributed among one or more computer systems configured to provide a service to one or more client computers, or to perform an overall task as part of a distributed system, such as the distributed computer system 300 shown in FIG. 3. Additionally, aspects may be performed on a client-server or multi-tier system that includes components distributed among one or more server systems that perform various functions. Consequently, embodiments are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Referring to FIG. 3, there is illustrated a block diagram of a distributed computer system 300, in which various aspects and functions are practiced. As shown, the distributed computer system 300 includes one or more computer systems that exchange information. More specifically, the distributed computer system 300 includes computer systems 302, 304, and 306. As shown, the computer systems 302, 304, and 306 are interconnected by, and may exchange data through, a communication network 308. The network 308 may include any communication network through which computer systems may exchange data. To exchange data using the network 308, the computer systems 302, 304, and 306 and the network 308 may use various methods, protocols and standards, including, among others, Fiber Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST, and Web Services. To ensure data transfer is secure, the computer systems 302, 304, and 306 may transmit data via the network 308 using a variety of security measures including, for example, SSL or VPN technologies. While the distributed computer system 300 illustrates three networked computer systems, the distributed computer system 300 is not so limited and may include any number of computer systems and computing devices, networked using any medium and communication protocol.

As illustrated in FIG. 3, the computer system 302 includes a processor 310, a memory 312, an interconnection element 314, an interface 316 and data storage element 318. To implement at least some of the aspects, functions, and processes disclosed herein, the processor 310 performs a series of instructions that result in manipulated data. The processor 310 may be any type of processor, multiprocessor or controller. Example processors may include a commercially available processor such as an Intel Xeon, Itanium, Core, Celeron, or Pentium processor; an AMD Opteron processor; an Apple A4 or A5 processor; a Sun UltraSPARC processor; an IBM Power5+ processor; an IBM mainframe chip; or a quantum computer. The processor 310 is connected to other system components, including one or more memory devices 312, by the interconnection element 314.

The memory 312 stores programs (e.g., sequences of instructions coded to be executable by the processor 310) and data during operation of the computer system 302. Thus, the memory 312 may be a relatively high performance, volatile, random access memory such as a dynamic random access memory ("DRAM") or static memory ("SRAM"). However, the memory 312 may include any device for storing data, such as a disk drive or other nonvolatile storage device. Various examples may organize the memory 312 into particularized and, in some cases, unique structures to perform the functions disclosed herein. These data structures may be sized and organized to store values for particular data and types of data.

Components of the computer system 302 are coupled by an interconnection element such as the interconnection element 314. The interconnection element 314 may include any communication coupling between system components such as one or more physical busses in conformance with specialized or standard computing bus technologies such as IDE, SCSI, PCI and InfiniBand. The interconnection element 314 enables communications, including instructions and data, to be exchanged between system components of the computer system 302.

The computer system 302 also includes one or more interface devices 316 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 302 to exchange information and to communicate with external entities, such as users and other systems.

The data storage element 318 includes a computer readable and writeable nonvolatile, or non-transitory, data storage medium in which instructions are stored that define a program or other object that is executed by the processor 310. The data storage element 318 also may include information that is recorded, on or in, the medium, and that is processed by the processor 310 during execution of the program. More specifically, the information may be stored in one or more data structures specifically configured to conserve storage space or increase data exchange performance. The instructions may be persistently stored as encoded signals, and the instructions may cause the processor 310 to perform any of the functions described herein. The medium may, for example, be optical disk, magnetic disk or flash memory, among others. In operation, the processor 310 or some other controller causes data to be read from the nonvolatile recording medium into another memory, such as the memory 312, that allows for faster access to the information by the processor 310 than does the storage medium included in the data storage element 318. The memory may be located in the data storage element 318 or in the memory 312, however, the processor 310 manipulates the data within the memory, and then copies the data to the storage medium associated with the data storage element 318 after processing is completed. A variety of components may manage data movement between the storage medium and other memory elements and examples are not limited to particular data management components. Further, examples are not limited to a particular memory system or data storage system.

Although the computer system 302 is shown by way of example as one type of computer system upon which various aspects and functions may be practiced, aspects and functions are not limited to being implemented on the computer system 302 as shown in FIG. 3. Various aspects and functions may be practiced on one or more computers having a different architectures or components than that shown in FIG. 3. For instance, the computer system 302 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 302 may be a computer system including an operating system that manages at least a portion of the hardware elements included in the computer system 302. In some examples, a processor or controller, such as the processor 310, executes an operating system. Examples of a particular operating system that may be executed include a Windows-based operating system, such as, Windows NT, Windows 2000 (Windows ME), Windows XP, Windows Vista or Windows 7 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Oracle Corporation, or a UNIX operating systems available from various sources. Many other operating systems may be used, and examples are not limited to any particular operating system.

The processor 310 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C# (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user space application) or in a commonly shared data structure (such as an application registry that is defined by an operating system). In addition, some examples provide for both system and user interfaces that allow external entities to modify the parameters and thereby configure the behavior of the components.

Based on the foregoing disclosure, it should be apparent to one of ordinary skill in the art that the embodiments disclosed herein are not limited to a particular computer system platform, processor, operating system, network, or communication protocol. Also, it should be apparent that the embodiments disclosed herein are not limited to a specific architecture or programming language.

Having now described some illustrative aspects of some embodiments, it should be apparent to those skilled in the art that the foregoing is merely illustrative and not limiting, having been presented by way of example only. While the bulk of this disclosure is focused on embodiments directed to business management, aspects of the embodiments disclosed herein may be applied to other information domains. Similarly, aspects of the embodiments disclosed herein may be used to achieve other. Numerous modifications and other illustrative embodiments are within the scope of one of ordinary skill in the art and are contemplated as falling within the scope of the embodiments disclosed herein. In particular, although many of the examples presented herein involve specific combinations of method acts or system elements, it should be understood that those acts and those elements may be combined in other ways to accomplish the same objectives.

Use of at least one of and a list of elements (e.g., A, B, C) is intended to cover one selection from A, B, C (e.g., A), two selections from A, B, C (e.g., A and B), three selections (e.g., A, B, C), and multiples of each selection. Use of ordinal terms such as "first", "second", "third", "a", "b" "c" etc., in the claims to modify or otherwise identify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A database system for executing multi-tier data and multi-platform data access requests, the system comprising:
at least one processor operatively connected to a memory, the at least one processor when executing configured to:
integrate with a first user device operatively paired with a second user device associated with a first user, wherein the first user device is configured to receive verbal commands from the first user and communicate verbal commands to the second user device;
receive verbal command data from the second user device via a secure application executing on the second user device;
authenticate the first user responsive to authentication input received as verbal commands received by the first user device or as input at the second user device through the secure application;
prevent acceptance of authentication information until identification of either one or both of the first or second user device as registered user devices, wherein identification is based, at least in part, on a unique registration number or digital fingerprint associated with the first and second user devices;
change execution parameters of the first device or the second device responsive to verbal command data received from the second user device via the secure application;
wherein changing the execution parameters of the first device includes at least one of: activating one or more sensors on the first device, deactivating one or more sensors of the first device, changing a data capture rate for the one or more sensors, or changing a data communication rate associated with the one or more sensors;
access a database having an associated plurality of access tiers, the plurality of access tiers including at least a first access tier including the first user, a second access tier including additional users granted electronic permission by the first user on the system to access data associated with the first user, and an access tier for administrative functions executed by the system;
determine an activity executed by the first user based on at least one of scheduling information stored in the database, resource allocations associated with the first user, personnel allocations associated with the first user, or facility associations associated with the first user made accessible through the access tier for administrative functions; and
tailor audio prompts to the first user responsive to the determined user activity.

2. The database system of claim 1, wherein the at least one processor is further configured to:
interpret verbal command data responsive to the determined user activity to disambiguate the verbal command data; and
execute the interpreted verbal command data according to parameters of the interpreted command.

3. The database system of claim 1, wherein the at least one processor is further configured to tailor audio prompts to the first user responsive to resource allocations associated with the first user, personnel allocations associated with the first user, or facility associations associated with the first user.

4. The database system of claim 1, wherein a first API is configured to received verbal command data and translate the verbal command data into executable commands for a nutrition planning service.

5. The database system of claim 4, wherein the first API is configured to translate requests for input or prompts for input into audio based requests communicated to either of the first user device or the second user device.

6. The database system of claim 1, wherein the at least one processor is further configured to:
match a current user activity to a set of sensors of at least the first and second user device;
activate the set of matching sensors; or
match a current user activity to set of sensors associated with at least one scheduled resource, the first device, or second device; and
trigger activation of the set of sensors associated with at least one scheduled resource, the first device, or the second device responsive to a verbal command at the first user device.

7. The database system of claim 1, further comprising at least a second API configured to access fitness regimen and translate a selected fitness regime into audio instructions for completing the fitness regimen.

8. The database system of claim 1, wherein the at least one processor is further configured to verbalize instructions from a virtual trainer instructing on a system generated fitness program.

9. The database system of claim 8, wherein the verbalized instructions from the virtual trainer are selected from sets of automatically generated fitness instructions, wherein selection is performed automatically by the system responsive to biologic data captured by the first user device.

10. The database system of claim 1, wherein the at least one processor is further configured to:
require continued authentication from the first user device or second user device;
monitor biologic data being received to permit continued authentication, and
absent communication of biologic data terminate an authentication session.

11. The database system of claim 1, wherein the second device establishes a secure connection to the first device such that biologic data collection and communication is encrypted between the first device, the second user device, and a database for storing the biologic data.

12. The database system of claim 11, wherein the second user device establishes a secure connection to the database through the secure application such that any data communicated is encrypted between the second device and the database system.

13. The database system of claim 1, wherein the first user device collects biologic data and the second user device communicates the biologic data to the at least one processor; and the at least one processor is further configured to:

store biologic data from the first user as a time series indexed with a known or inferred activity of the user;

associate the biologic data to a plurality of access tiers including at least a first access tier with the first user, a second access tier for additional users granted electronic permission on the system to access the biologic data by a user associated with the biologic data, and an access tier from administrative functions executed by the system or components;

limiting within each access tier access by the additional users to only the data associated with respective users having given permission on the system.

14. The database system of claim 1, wherein the at least one processor is further configured to capture sensor data on the first user including biologic data and associate the biologic data to a plurality of access tiers in the database, the plurality of access tiers including at least a first access tier including the first user, a second access tier including additional users granted electronic permission on the system to access the biologic data by a user associated with the biologic data.

15. The database system of claim 14, wherein the at least one processor is further configured to:
    display an interface for the additional users to remotely access the system, request services for the first user, receive reports on the first user's biologic data, and access the biologic data associated with the first user within the interface; and
    generate an interface for the first user to remotely access the system.

16. The database system of claim 1, wherein the at least one processor is further configured to receive sensor data from at least the first and second device and store the sensor data in records associated with the first user.

17. The database system of claim 16, wherein the at least one processor is further configured to store the sensor data with associations to any biologic data received on the first user.

18. A database system for executing multi-tier data and multi-platform data access requests, the system comprising:
    at least one processor operatively connected to a memory, the at least one processor when executing configured to:
    integrate with a first user device operatively paired with a second user device associated with a first user, wherein the first user device is configured to receive verbal commands from the first user and communicate verbal commands to the second user device;
    receive verbal command data from the second user device via a secure application executing on the second user device;
    authenticate the first user responsive to authentication input received as verbal commands received by the first user device or as input at the second user device through the secure application;
    prevent acceptance of authentication information until identification of either one or both of the first or second user device as registered user devices, wherein identification is based, at least in part, on a unique registration number or digital fingerprint associated with the first and second user devices;
    change execution parameters of the first device or the second device responsive to verbal command data received from the second user device via the secure application;
    wherein changing the execution parameters of the first device includes at least one of: activating one or more sensors on the first device, deactivating one or more sensors of the first device, changing a data capture rate for the one or more sensors, or changing a data communication rate associated with the one or more sensors;
    access a database having an associated plurality of access tiers, the plurality of access tiers including at least a first access tier including the first user, a second access tier including additional users granted electronic permission by the first user on the system to access data associated with the first user, and an access tier for administrative functions executed by the system;
    determine an activity executed by the first user based on at least one of scheduling information stored in the database, resource allocations associated with the first user, personnel allocations associated with the first user, or facility associations associated with the first user made accessible through the access tier for administrative functions;
    interpret verbal command data responsive to the determined user activity to disambiguate the verbal command data; and
    execute the interpreted verbal command data according to parameters of the interpreted command.

19. The database system of claim 18, wherein the at least one processor is further configured to tailor audio prompts to the first user responsive to the determined user activity.

20. The database system of claim 19, wherein the at least one processor is further configured to tailor audio prompts to the first user responsive to resource allocations associated with the first user, personnel allocations associated with the first user, or facility associations associated with the first user.

* * * * *